US008486865B2

(12) United States Patent
Weissman et al.

(10) Patent No.: US 8,486,865 B2
(45) Date of Patent: Jul. 16, 2013

(54) METHODS FOR DETECTING MODIFICATION RESISTANT NUCLEIC ACIDS

(75) Inventors: Jonathan Weissman, San Francisco, CA (US); Nicholas Ingolia, San Francisco, CA (US); Sina Ghaemmaghami, San Francisco, CA (US); John Newman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 622 days.

(21) Appl. No.: 12/611,817

(22) Filed: Nov. 3, 2009

(65) Prior Publication Data

US 2010/0120625 A1 May 13, 2010

Related U.S. Application Data

(60) Provisional application No. 61/110,921, filed on Nov. 3, 2008.

(51) Int. Cl.
*C12Q 1/68* (2006.01)
*C40B 30/00* (2006.01)

(52) U.S. Cl.
USPC ................................................ 506/7; 435/6.1

(58) Field of Classification Search
None
See application file for complete search history.

(56) References Cited

U.S. PATENT DOCUMENTS

| | | | |
|---|---|---|---|
| 6,172,218 B1 | 1/2001 | Brenner | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,306,597 B1 | 10/2001 | Macevicz | |
| 6,969,488 B2 | 11/2005 | Bridgham et al. | |
| 7,057,026 B2 | 6/2006 | Barnes et al. | |
| 7,115,400 B1 | 10/2006 | Adessi et al. | |
| 7,181,122 B1 | 2/2007 | Levene et al. | |
| 7,211,414 B2 | 5/2007 | Hardin et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,414,163 B1 | 8/2008 | Boldingh et al. | |
| 7,427,673 B2 | 9/2008 | Balasubramanian et al. | |
| 2003/0166054 A1* | 9/2003 | Lee et al. ..................... | 435/69.1 |
| 2005/0010145 A1 | 1/2005 | Fenkett | |
| 2005/0042648 A1 | 2/2005 | Griffiths et al. | |
| 2005/0059048 A1 | 3/2005 | Gunderson et al. | |
| 2005/0079510 A1 | 4/2005 | Berka et al. | |
| 2005/0100900 A1 | 5/2005 | Kawashima et al. | |
| 2005/0130173 A1 | 6/2005 | Leamon et al. | |
| 2006/0188901 A1 | 8/2006 | Barnes et al. | |
| 2006/0228721 A1 | 10/2006 | Leamon et al. | |
| 2006/0240439 A1 | 10/2006 | Smith et al. | |
| 2006/0281109 A1 | 12/2006 | Barr Ost et al. | |
| 2007/0166705 A1 | 7/2007 | Milton et al. | |
| 2008/0076121 A1 | 3/2008 | Wolber | |
| 2008/0108082 A1 | 5/2008 | Rank et al. | |

FOREIGN PATENT DOCUMENTS

| | | |
|---|---|---|
| WO | WO 91/06678 A1 | 5/1991 |
| WO | WO 98/44151 A1 | 10/1998 |
| WO | WO 00/18957 A1 | 4/2000 |
| WO | WO 02/46456 A1 | 6/2002 |
| WO | WO 2005/010145 A2 | 2/2005 |
| WO | WO 2005/065814 A1 | 7/2005 |
| WO | WO 2006/064199 A1 | 6/2006 |
| WO | WO 2007/010251 A2 | 1/2007 |
| WO | WO 2007/123744 A2 | 11/2007 |

OTHER PUBLICATIONS

Adilakshmi et al. (Nucleic Acids Research, 2006, 34(8):e64:1-7).*
Schena et al. (Science, 1995, vol. 270, p. 467-470).*
Seo et al. (PNAS, 2005, 102(17)5926-5931).*
Huttenhoffer et al. (EMBO Journal, 1994, 13(16):3892-3901, IDS reference).*
Kolupaeva, et al. Journal Biological Chemistry, 1998, 29(17):18599-18604.*
Vytvytska, et al., Genes Dev., 2000, 14:1109-1118.*
Wolin, Sandra L. et al., "Ribosome pausing and stacking during translation of a eukaryotic mRNA." The EMBO Journal, Nov. 1988, 7(11):3559-69.
Extended European Search Report dated Nov. 11, 2011 for EP Application No. 09829688.2, 5 pages.
Ingolia, Nicholas T. et al., "Genome-wide analysis in vivo of translation with nucleotide resolution using ribosome profiling", Apr. 10, 2009, Science 324:218-223.
International Preliminary Report on Patentability and Written Opinion dated May 3, 2011 for International PCT Application No. PCT/US2009/063165, 7 pages.
Sachs, Matthew S. et al., "Toeprint analysis of the positioning of translation apparatus components at initiation and termination codons of fungal mRNAs", 2002, Methods 26:105-114.
U.S. Appl. No. 12/295,337, filed Dec. 17, 2009, Saibal Banerjee.
Alexeeva, Ekaterina V. et al., "Interaction of mRNA with the *Escherichia coli* ribosome: accessibility of phosphorothioate-containing mRNA bound to ribosomes for iodine cleavage", Nucleic Acids Research 1996, 24(12):2228-35.
Bentley, David R. et al., "Accurate whole human genome sequencing using reversible terminator chemistry", Nature Nov. 6, 2008, 456(6):53-9.
Harris, Timothy D. et al., "Single Molecule DNA Sequencing of a viral Genome", Science Apr. 4, 2008, 320:106-9.
Holstege, Frank C.P. et al., "Dissecting the regulatory circuitry of a eukaryotic genome", Cell Nov. 25, 1998, 95: 717-28.
Huttenhofer, Alexander et al., "Footprinting mRNA-ribosome complexes with chemical probes", The EMBO Journal 1994, 13(16):3892-901.

(Continued)

*Primary Examiner* — Stephanie K Mummert
(74) *Attorney, Agent, or Firm* — Kilpatrick Townsend & Stockton LLP

(57) ABSTRACT

Methods are provided for, inter alia, detecting nucleic acid molecules resistant to degradation, such as a plurality of RNA molecules bound to a ribosome, using various technologies including deep sequencing.

28 Claims, 32 Drawing Sheets

OTHER PUBLICATIONS

Konevega, Andrey L. et al., "Spontaneous reverse movement of mRNA-bound tRNA through the ribosome", Nature Structural & Molecular Biology, Apr. 2007, 14(4):318-24.

Korlach, Jonas et al., "Long, processive enzymatic DNA synthesis using 100% dye-labeled terminal phosphate-linked nucleotides", Nucleosides, Nucleotides and Nucleic Acids 2008, 27:1072-83.

Metzker, Michael L., "Emerging technologies in DNA sequencing", Genome Res. 2005, 15:1767-76.

Morin, Ryan D. et al., "Profiling the HeLa S3 transcriptome using randomly primed cDNA and massively parallel short-read sequencing", BioTechniques 2008, 45(1):81-94.

Morris, David R., "Ribosomal footprints on a transriptome landscape", Genome Biology Apr. 28, 2009, 10(4):215.1-215.3.

Mortazavi, Ali et al., "Mapping and quantifying mammalian transcriptomes by RNA-seq", Nature Methods, Jul. 2008, 5(7):621-8.

Nagalakshmi, Ugrappa et al., "The transcriptional landscape of the yeast genome defined by RNA sequencing", Science, Jun. 6, 2008, 320:1344-9.

Reinartz, Jeanette et al., "Massively parallel signature sequencing (MPSS) as a tool for in-depth quantitative gene expression profiling in all organisms", Briefings in Functional Genomics and Proteomics, Feb. 2002, 1(1):95-104.

Rothberg, Jonathan M. et al., "The development and impact of 454 sequencing", Nature Biotechnology, Oct. 2008, 26(10): 1117-24.

Ruparel, Hameer et al., "Design and synthesis of a 3'—O-allyl photocleavable fluorescent nucleotide as a reversible terminator for DNA sequencing by synthesis", PNAS, Apr. 26, 2005, 102(17): 5932-7.

Wang, Yulei et al., "Precision and functional specificity in mRNA decay" PNAS, Apr. 30, 2002, 99(9):5860-5.

International Search Report for International Application No. PCT/US2009/063165 dated Jul. 14, 2010, 6 pages.

Steitz, Joan A., "Polypeptide Chain Initiation: Nucleotide Sequences of the Three Ribosomal Binding Sites in Bacteriophage R17 RNA", Nature, Dec. 6, 1969, 224:957-964.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: t modified by 5' biotin

<400> SEQUENCE: 1
tggcgccaga agcgagagcc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: a modified by 5' biotin

<400> SEQUENCE: 2
agacaggcgt agccccggga                                              20

<210> SEQ ID NO 3
<211> LENGTH: 24
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: g modified by 5' biotin

<400> SEQUENCE: 3
gatcagaagg acttgggccc ccca                                         24

<210> SEQ ID NO 4
<211> LENGTH: 30
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: c modified by 5' biotin
```

-continued

```
<400> SEQUENCE: 4
cgatcggccc gaggttatct agagtcacca                                           30

<210> SEQ ID NO 5
<211> LENGTH: 30
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: t modified by 5' biotin

<400> SEQUENCE: 5
tccattattc ctagctgcgg tatccaggcg                                           30

<210> SEQ ID NO 6
<211> LENGTH: 19
<212> TYPE: DNA
<213> ORGANISM: Artificial Sequence
<220> FEATURE:
<223> OTHER INFORMATION: Synthetic subtraction antisense, biotinylated
      DNA
<220> FEATURE:
<221> NAME/KEY: modified_base
<222> LOCATION: (1)..(1)
<223> OTHER INFORMATION: c modified by 5' biotin

<400> SEQUENCE: 6
ccgagaggca aggggcggg                                                      19
```

METHODS FOR DETECTING MODIFICATION RESISTANT NUCLEIC ACIDS

CROSS-REFERENCE TO RELATED APPLICATIONS

This application claims the benefit of U.S. Provisional Application No. 61/110,921, filed Nov. 3, 2008, which is incorporated herein by reference in its entirety and for all purposes.

STATEMENT AS TO RIGHTS TO INVENTIONS MADE UNDER FEDERALLY SPONSORED RESEARCH OR DEVELOPMENT

This invention was made with government support under grant numbers F32 GM080853, F32 GM067512, P01 AG10770 and T32 AG000278 awarded by the National Institutes of Health. The Government has certain rights in the invention.

BACKGROUND OF THE INVENTION

Gene expression reflects many important aspects of cellular physiology, including changes during development as well as disease states. Microarrays provide quantitative, genome-wide measurements of expression by monitoring mRNA abundance. Deep sequencing has recently emerged as an alternative to microarrays that promises some advantages in characterizing and quantifying the full pool of cellular mRNA. However, mRNA abundance is an imperfect proxy for protein production, which is the ultimate molecular expression of a protein-coding gene. Quantifying the translation of mRNA into protein is thus of very general interest in biology. For instance, microRNAs can repress target genes translationally, and so their direct effects may only be visible to measures of translation as opposed to mRNA abundance. Translational regulation also plays an important role in development and in learning and memory. Measuring translation, especially on a genome-wide scale, has proven to be more technically challenging than measuring mRNA abundance. Typically, transcripts are fractionated based on ribosome occupancy, and different fractions are then analyzed by microarray to determine the translational status of different messages. However, this approach requires the analysis of many fractions in parallel, and even then achieves only limited quantitative resolution. Furthermore, polysome fractionation gives no information about the position of the ribosome on the mRNA. While conceptual translation typically identifies the correct protein-coding sequence, there are exceptions such as programmed ribosomal frameshifting. Upstream open reading frames (uORFs), short translated sequences in the 5' UTR of many genes, pose a particularly prominent difficulty. There are a few well-studied instances where these uORFs are clearly translated, often with consequences for the translation of the downstream protein-coding gene, and many more are highly conserved. However, it is challenging to directly demonstrate uORF translation, and polysome profiling cannot distinguish whether ribosomes are occupying the uORF or the CDS on a transcript.

Translating ribosomes occupy a discrete footprint on their mRNA template. Steitz first demonstrated the ribosomal footprint in vitro using nuclease digestion to remove unprotected mRNA, leaving behind a ribosome-protected fragment. However, the technology available to characterize these RNA fragments has been quite limited. The accumulation of ribosome footprints derived from a specific position in an mRNA can reveal ribosomal pausing during in vitro eukaryotic translation. However, until now techniques have not been available to quantify translation by combining the historical observation of ribosome footprinting with new advances in deep sequencing.

Embodiments of the present disclosure are based, at least in part, on the surprising observation that capturing and characterizing the footprints from in vivo ribosomes can reveal the full translational profile of the cell. The eukaryotic ribosome protects roughly 30 nucleotides of mRNA from digestion, a length which corresponds well to the sequence reads of the highest-capacity deep sequencing platforms. The sequence of a ribosome footprint identifies its source, and thus the position of one ribosome, and deep sequencing can analyze tens of millions of reads in parallel. In a particular embodiment, quantitative and highly reproducible measurements of translation can be obtained for budding yeast by counting ribosome footprint sequences. Because ribosome footprints show the exact location of the ribosome, not just which mRNA it is translating, variations in ribosome occupancy within genes can be determined as can the presence of ribosomes on upstream open reading frames (uORFs) as opposed to coding sequences.

BRIEF SUMMARY OF THE INVENTION

In a first aspect, there is provided a method for detecting a plurality of RNA molecules bound to at least one ribosome. The method includes the step of contacting the plurality of RNA molecules with an enzymatic degradant or a chemical degradant thereby forming a plurality of RNA fragments, wherein each RNA fragment comprises an RNA portion protected from the enzymatic degradant or the chemical degradant by a ribosome to which the RNA portion is bound. The method further includes amplifying the RNA fragments to form a detectable number of amplified nucleic acid fragments. The method further includes detecting the detectable number of amplified nucleic acid fragments, thereby detecting the plurality of RNA molecules bound to at least one ribosome.

In another aspect, there is provided a method for detecting a nucleic acid comprising a nucleic acid portion resistant to enzymatic modification or chemical modification. The method includes the step of contacting the nucleic acid with an enzymatic modifying agent or chemical modifying agent thereby forming a nucleic acid fragment which includes the nucleic acid portion. The method further includes amplifying the nucleic acid fragment to form a detectable number of amplified nucleic acid fragments. The method further includes sequencing the detectable number of amplified nucleic acid fragments, thereby detecting the nucleic acid.

In yet another aspect, there is provided a method for detecting an RNA bound to at least one ribosome. The method includes the step of contacting the RNA bound to at least one ribosome with an enzymatic degradant or chemical degradant thereby forming an RNA fragment, wherein the RNA fragment includes an RNA portion protected from the enzymatic degradant or the chemical degradant by a ribosome to which the RNA portion is bound. The method further includes contacting the RNA fragment with a DNA polymerase and a DNA polymerase primer thereby forming a linear DNA. The method further includes contacting the linear DNA with a ligase thereby forming a circularized DNA. The method further includes amplifying the circularized DNA thereby forming a detectable number of amplified DNA molecules. The method further includes detecting the detectable number of amplified DNA molecules, thereby detecting the RNA bound to at least one ribosome.

In still another aspect, there is provided a method for detecting a relative amount of translation of an RNA sequence. The method includes the step of contacting a plurality of RNA molecules with an enzymatic modifying agent or chemical modifying agent, wherein each of the plurality of RNA molecules comprises an identical base sequence and is bound to a different ribosome, thereby forming a plurality of partially degraded RNA molecules. The method further includes contacting the plurality of partially degraded RNA molecules with a DNA polymerase and a DNA polymerase primer thereby forming a plurality of linear DNA molecules. The method further includes contacting the plurality of linear DNA molecules with a ligase thereby forming a plurality of circularized DNA molecules. The method further includes amplifying the plurality of circularized DNA molecules thereby forming a detectable number of amplified DNA molecules. The method further includes detecting and quantifying the detectable number of amplified DNA molecules thereby detecting the amount of amplified DNA molecules.

In another aspect, there is provided a method for detecting a relative amount of translation of an RNA sequence. The method includes contacting a plurality of RNA molecules with an enzymatic modifying agent or chemical modifying agent, wherein each of the plurality of RNA molecules comprises an identical base sequence and is bound to a different ribosome, thereby forming a plurality of partially degraded RNA molecules. The method further includes contacting the plurality of partially degraded RNA molecules with a DNA polymerase and a DNA polymerase primer thereby forming a plurality of linear DNA molecules. The method further includes contacting the plurality of linear DNA molecules with a ligase thereby forming a plurality of circularized DNA molecules. The method further includes amplifying the plurality of circularized DNA molecules thereby forming a detectable number of amplified DNA molecules. The method further includes detecting and quantifying the detectable number of amplified DNA molecules thereby detecting the amount of amplified DNA molecules. The method further includes comparing the amount of amplified DNA molecules to a standard control, thereby detecting the relative amount of translation of the RNA sequence.

In yet another aspect, there is provided a method for determining translation activity for a plurality of RNA molecules. The method includes treating a plurality of RNA-ribosome complexes, wherein each RNA-ribosome complex includes an RNA molecule having an RNA portion that is bound to a ribosome, under conditions sufficient to produce a plurality of RNA fragments, wherein each RNA fragment includes an RNA portion and wherein each RNA fragment includes a nucleotide sequence that is longer than the nucleotide sequence of the RNA portion. The method further includes sequencing the plurality of RNA fragments to determine the nucleotide sequences of the RNA portions. The method further includes comparing the nucleotide sequences of the plurality of RNA portions to the nucleotide sequences of the RNA molecules, thereby determining translation activity for the plurality of RNA molecules.

BRIEF DESCRIPTION OF THE DRAWINGS

(FIG. 1A) Exemplary protocol for converting ribosome footprints or randomly-fragmented mRNA into a deep sequencing library. (FIG. 1B) Technical reproducibility of mRNA abundance measurements. The error estimate is based on the $\chi^2$ statistic, as known in the art. (FIG. 1C) Reproducibility of mRNA abundance measurements between two full biological replicates. Genes with at least 128 total reads counted should have low relative error from counting statistics. (Inset) Histogram of $\log_2$ ratios between replicates for genes with at least 128 reads, along with the normal error curve (mean=0.076, std dev=0.252 in $\log_2$ units).

(FIG. 2A) Total ribosome footprints falling near the beginning or end of coding sequences. The offset between the start of the footprint and the P- and A-site codons can be calibrated from the onset of footprints at the edges of the coding sequence. Reads from the fragmented mRNA control extends beyond the coding sequence and lacks a strong triplet code periodicity. (FIG. 2B) Position of ribosome footprints relative to the reading frame. The 28 nt ribosome footprints typically start at the first nucleotide of a codon, while the 29 nucleotide ribosome footprints may be extended by 1 nucleotide on either side. Random mRNA fragments show no strong reading frame bias.

(FIG. 3A) Reproducibility of ribosome footprint density between two complete biological replicates. Genes with at least 128 total reads counted (2878 of 5295) should have low relative error from counting statistics. (Inset) Histogram of $\log_2$ of ratios between replicates for genes with at least 128 reads, along with the normal error curve (mean=0.084, std dev=0.291 in log 2 units). (FIG. 3B) Histogram of ratio of ribosome footprint density to mRNA density. The ratio is normalized to the average ratio for all genes. The error shows actual inter-replicate ratios between biological replicates, which are roughly normally distributed (std dev=0.367 in log 2 units). (FIG. 3C) Translation density as a function of length. Genes were binned based on length, and the median of the ribosome to mRNA ratio was found for each length class and normalized against the 1 kb length class. (FIG. 3D) Read density as a function of position. Read counts were independently normalized for each well-expressed gene, and genes were then averaged with equal weight.

(FIG. 4A) Density of mRNA and ribosome reads on non-protein-coding sequences, relative to the associated gene. (FIG. 4B) Histogram of ribosome to mRNA ratios for different classes of sequences. The ratio is normalized to the median ratio for CDSes. Introns and 3' UTRs are uniformly poorly translated, while 5' UTRs span a very broad range. (FIG. 4C) Ribosome and mRNA density showing the uORF in the ICY1 5' UTR. The ATG and stop codons for the uORF, as well as the ATG codon for the main ORF, are shown. (FIG. 4D) Translational status of uORFs. Upstream ATGs were taken from annotated 5' UTRs with high mRNA abundance. The predicted uORFs were classified based on the presence of ribosome footprints. Three categories were established for strong evidence of translation, weak or ambiguous evidence, and evidence against translation. (FIG. 4E) Classification of translation in 5' UTRs Annotated 5' UTRs were classified based on whether there were significant (>1 rpM) ribosome footprints, and whether at least half of those footprints could be attributed to an ATG uORF or a predicted non-ATG uORF. (FIG. 4F, FIG. 4G) Ribosome and mRNA density showing non-ATG uORFs in PRE2 and PDR5. The proposed AAATTG translational initiation site, along with the subsequent reading frame and stop codon, are shown for the non-ATG uORF.

(FIG. 5A) Changes in mRNA abundance and translation in response to starvation. For 3769 genes where reliable measurements were possible, the fold change in the ratio of ribosome to mRNA density upon starvation, as a measure of translation, is plotted against the fold change in mRNA abundance. The translationally induced gene GCN4 is indicated, as are the subset of genes involved in ribosome biogenesis. (FIG. 5B) Distribution of translational changes. The cumulative distribution of ratios of translation in starvation versus log-phase growth shows the extent and magnitude of translational regulation. The cumulative distribution of ratios between biological replicates is shown as well, demonstrating that the translational changes are much larger than expected by chance.

(FIG. 6A) Ribosome and mRNA densities in the GCN4 5' UTR in repressive and inducing conditions. The four known uORFs are indicated, along with the proposed initiation sites for upstream translation. (FIG. 6B) Non-ATG uORF upstream of GCN4. An enlargement of (FIG. 6A), as shown with the grey box, focusing on the region of unanticipated translation. (FIG. 6C) Ribosome occupancy of non-coding sequences. The number of ribosome footprints for 5' UTR regions, 3' UTR regions, and introns relative to the number of CDS reads, as well as the number of ribosome footprints for annotated transposon protein-coding genes for comparison. (FIG. 6D) Translation of 5' UTR sequences. The ratio of ribosome footprints to mRNA fragments is normalized against the overall CDS total. Good initiation context was calculated by the model of Miyasaka, with a threshold of >0.001 for ATG uORFs and >0.01 for non-ATG uORFs. GCN4 uORF 1 accounts for 68% (log-phase) or 44% (starvation) of ribosome footprints on ATG uORFs in favorable initiation contexts. The number of 5' UTRs with ribosome-occupied uORFs during log-phase growth is indicated for each class.

(FIG. 8A, FIG. 8B) Read coverage of two well-expressed yeast genes. The UTR boundaries are taken from a large-scale full-length cDNA analysis (Miura F et al., *Proc. Natl. Acad. Sci. USA* 103:17846 (2006)). Coverage shows only a 3- to 4-fold variability within coding sequences and is clearly much lower in the RPL39 intron. (FIG. 8C, FIG. 8D) Histogram of read starts at specific nucleotides. The poly-(A) polymerase sample was generated using our standard approach (FIG. 1A). The T4 Rnl1 sample used T4 Rnl1 to ligate an oligonucleotide linker that served as a primer site for reverse transcription and was otherwise the same. We counted read starts at each position in the PGK1 coding sequence. Read starts are more variable than read coverage, which averages over 25-30 individual read starts. The distribution in read starts is broader for the T4 Rnl1 site, leading to higher variability in coverage. (FIG. 8E) Lorenz curve of read starts. This curve shows the fraction of total reads accounted for by a given fraction of positions in the gene, ordered by coverage. Perfectly even coverage would give a diagonal line. The consistent shift of the T4 Rnl1 sample to the right of the poly-(A) polymerase sample indicates that a smaller number of sites accounts for a larger number of reads in the T4 Rnl1 sample.

(FIG. 9A) Comparison between our mRNA abundance measurements and microarray data. Our measurement of mRNA abundance correlates well with the Holstege et al. data set which used single-channel microarrays normalized against genomic DNA to compare abundance between different mRNAs. (FIG. 9B) Comparison between our mRNA abundance measurement and an alternate transcriptome sequencing approach. The Nagalakshmi et al. data set used deep sequencing of unfragmented mRNAs and quantified only reads in a 30 by window upstream of the stop codon. (FIG. 9C) Comparison between the two previous whole-genome measurements.

(FIG. 10A) Sucrose density gradient analysis of nuclease-digested extracts. Digestion with RNase I collapses nearly all polysomes to monosomes. The solid boxes indicate the fractions pooled for the monosome sample. (FIG. 10B) Nuclease protection assay showing ribosome-protected mRNA fragments. The probe is antisense to the 5'-most 500 nt of TDH2. The monosome fraction of digested extracts contains a mRNA fragment that is roughly 30 nt long. In contrast, total RNA contains much longer fragments, and the message is virtually absent from the undigested monosome fraction. (FIG. 10C) Length distribution of ribosome footprint sequences. Ribosome footprints have a distinctive length which is different from that of other captured RNAs and which corresponds to the size of the fragments seen in (B). Only reads whose length was unambiguous, based on a terminal genome-encoded non-A nucleotide in the read sequence followed by an A not present in the genomic alignment, were included. The rRNA fragments are the nuclease-generated rRNA contamination in the ribosome footprint sample. The mRNA fragments are from a randomly-fragmented sample that was size-selected and prepared in parallel to the footprint sample.

(FIG. 11A, FIG. 11B) Protein abundance by mass spectrometry versus mRNA and ribosome density. Protein abundance correlates better with ribosome density than mRNA abundance. Furthermore, many outliers are ribosomal proteins, including the single-copy Rpl29p, that are likely to be high-abundance proteins and thus represent errors in the mass spectrometry data. Protein abundance was derived from summed ion intensity in haploid samples from de Godoy et al. (FIG. 11C, FIG. 11D) As FIG. 11A and FIG. 11B, using protein abundance from Western blotting against TAP-tagged proteins from Ghaemmaghami et al.

(FIG. 12A) Ribosome footprint abundance correlates well, but not perfectly, with mRNA abundance. Genes with more abundant mRNA are also translated more highly. The average ratio of footprint density to mRNA fragment density was computed from genes with at least 128 total reads. (FIG. 12B) Ribosome occupancies of genes classified by whole-genome polysome profiling. A previous study quantified relative mRNA abundance in eight polysome fractions and found a distinct peak of mRNA abundance for each of 2128 genes. Ribosome occupancy was estimated for genes peaking in each of these fractions by scaling total ribosome counts by mRNA fragment density. Genes peaking in heavier polysome fractions tend to have higher ribosome occupancy. A five-number summary (minimum, lower quartile, median, upper quartile, and maximum) along with outliers were plotted for each peak fraction.

(FIG. 13A) Read density as a function of position relative to the end of the coding sequence. Ribosome occupancy appears to be uniform at the end of the gene, then stops abruptly at the stop codon. Only genes that are at least 500 codons long were included in the average to avoid any effect of the start of the gene on the window examined. Read counts were independently normalized for each well-expressed gene, and genes were then averaged with equal weight. (FIG. 13B) Comparison of short (500-1000 bp) and long (>2000 bp) genes. (FIG. 13C) Comparison of moderately-expressed (100 to 167 rpkM ribosome footprint density) and highly-expressed (>333 rpkM ribosome footprint density) genes. (FIG. 13D) Comparison of genes with and without predicted N-terminal signal sequences. The overall three-phase trend in ribosome density appears to be independent of length, expression level, and the presence of a signal sequence.

(FIG. 16A) Polysome profiles from a culture split in half, with one half transferred to minimal media without amino acids for 20 min. There is a substantial loss of polysomal ribosomes, with a corresponding increase in monosomal ribosomes, consistent with previous reports. (FIG. 16B) Reproducibility of mRNA abundance measurements following starvation. Histogram of $\log_2$ ratios between replicates for genes with at least 128 reads, along with the normal error curve (mean=0.021, std dev=0.332 in log 2 units). (FIG. 16C) Reproducibility of ribosome footprint density following starvation. Histogram of $\log_2$ ratios between replicates for genes with at least 128 reads, along with the normal error curve (mean=−0.092, std dev=0.326 in $\log_2$ units).

(FIG. 19A) Starvation increases ribosome density on the first 30 codons. Ribosome density as a function of position was plotted during starvation versus log-phase growth, as in FIG. 3. Starvation substantially increases ribosome density in the first 30 codons, but the subsequent slow relaxation to a constant density is unchanged from log-phase growth. (FIG. 19B) Increased 5' UTR occupancy during starvation. Histogram of ribosome to mRNA ratio for different classes of sequence under starvation conditions, similar to FIG. 4B.

DETAILED DESCRIPTION OF THE INVENTION

I. Definitions

Figure 1A:
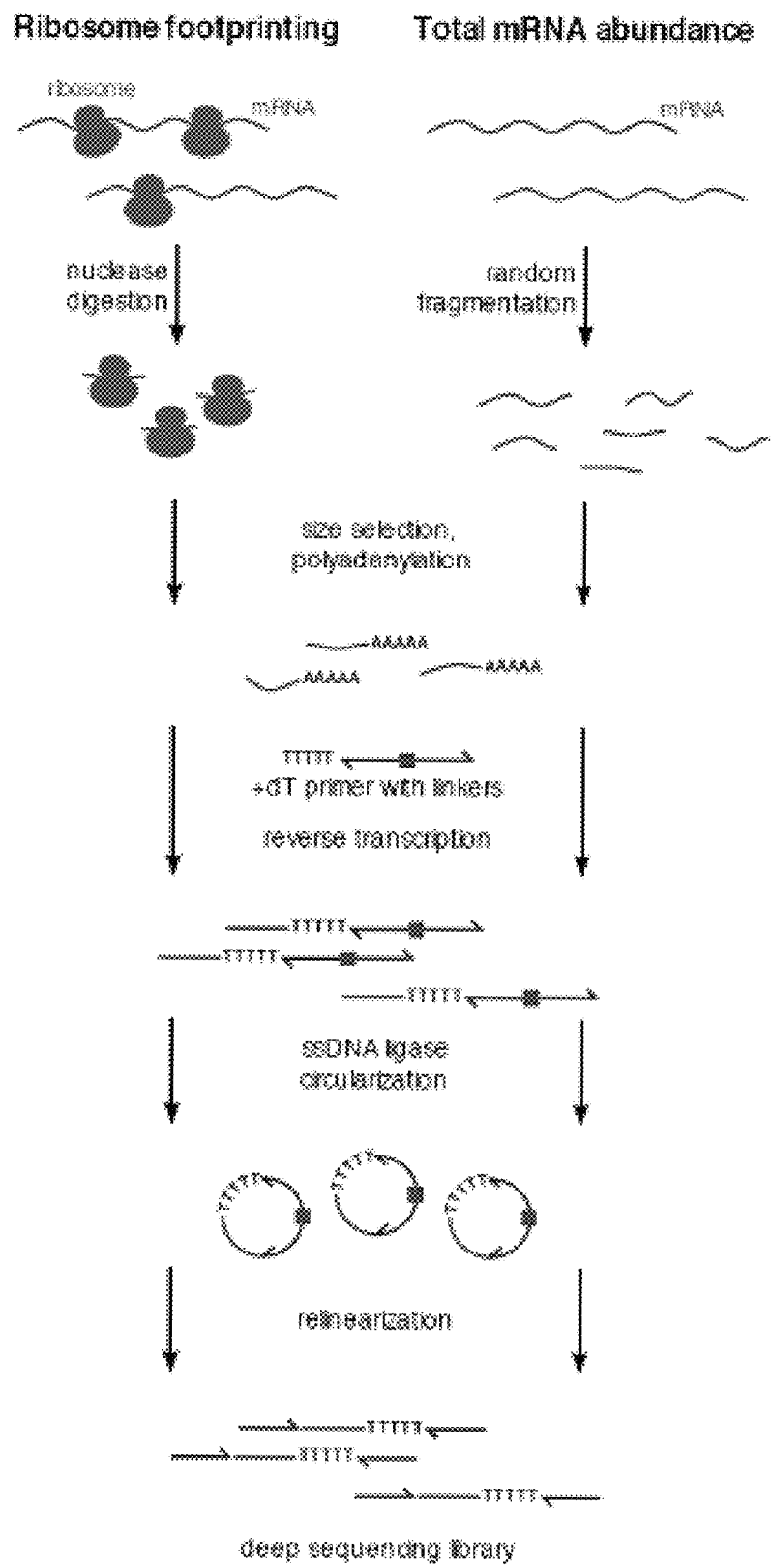
FIGS. 1A-C. Quantifying mRNA abundance and ribosome footprints by deep sequencing.

As used herein, "nucleic acid" means DNA, RNA and derivatives thereof. In some embodiments, the nucleic acid is single stranded. Modifications include, but are not limited to, those which provide other chemical groups that incorporate additional charge, polarizability, hydrogen bonding, electrostatic interaction, and functionality to the nucleic acid ligand bases or to the nucleic acid ligand as a whole. Such modifications include, but are not limited to, phosphodiester group modifications (e.g., phosphorothioates, phosphorodithioates, boranophosphonates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping moieties. A 2' deoxy nucleic acid linker is a divalent nucleic acid compound of any appropriate length and/or internucleotide linkage wherein the nucleotides are 2' deoxy nucleotides.

The terms "DNA" and "RNA" refer to deoxyribonucleic acid and ribonucleic acid, respectively.

"Translatable RNA," as used herein, refers to RNA that is capable of being translated into a peptide, polypeptide or protein in a cell, in situ, or in vivo. Examples of translatable RNA include, but are not limited to, mRNA and RNA containing one or more open reading frames.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

"Complementary," as used herein, refers to the capacity for precise pairing of two nucleobases (e.g., A to T (or U), and G to C) regardless of where in the nucleic acid the two are located. For example, if a nucleobase at a certain position of one nucleic acid is capable of hydrogen bonding with a nucleobase at a certain position of another nucleic acid, then the position of hydrogen bonding between the two nucleic acids is considered to be a complementary position. Nucleic acids are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acids. The phrase "substantially complementary" thus means that there may be one or more mismatches between the nucleic acids when they are aligned, provided that stable and specific binding occurs. The term "mismatch" refers to a site at which a nucleobase in one nucleic acid and a nucleobase in another nucleic acid with which it is aligned are not complementary. The nucleic acids are "perfectly complementary" to each other when they are fully complementary across their entire length.

The phrase "amino acid" as used herein refers to any of the twenty naturally occurring amino acids as well as any modified amino acids. Modifications can include natural processes such as posttranslational processing, or chemical modifications which are known in the art. Modifications include, but are not limited to, phosphorylation, ubiquitination, acetylation, amidation, glycosylation, covalent attachment of flavin, ADP-ribosylation, cross linking, iodination, methylation, and the like.

The words "protein", "peptide", and "polypeptide" are used interchangeably to denote an amino acid polymer or a set of two or more interacting or bound amino acid polymers.

The term "deep sequencing" refers to a method of sequencing a plurality of nucleic acids in parallel. See e.g., Bentley et al., *Nature* 2008, 456:53-59. In a typical deep sequencing protocol, nucleic acids (e.g. DNA fragments) are attached to the surface of a reaction platform (e.g., flow cell, microarray, and the like). The attached DNA molecules may be amplified in situ and used as templates for synthetic sequencing (i.e., sequencing by synthesis) using a detectable label (e.g. fluorescent reversible terminator deoxyribonucleotide). Representative reversible terminator deoxyribonucleotides may include 3'-O-azidomethyl-2'-deoxynucleoside triphosphates of adenine, cytosine, guanine and thymine, each labeled with a different recognizable and removable fluorophore, optionally attached via a linker. Where fluorescent tags are employed, after each cycle of incorporation, the identity of the inserted based may be determined by excitation (e.g., laser-induced excitation) of the fluorophores and imaging of the resulting immobilized growing duplex nucleic acid. The fluorophore, and optionally linker, may be removed by methods known in the art, thereby regenerating a 3' hydroxyl group ready for the next cycle of nucleotide addition.

II. Methods and Kits

In one aspect, a method is provided for detecting a nucleic acid including a nucleic acid portion resistant to enzymatic modification or chemical modification. The method includes contacting the nucleic acid with an enzymatic modifying agent or chemical modifying agent thereby forming a modified nucleic acid including the nucleic acid portion. The modified nucleic acid is amplified to form a detectable number of amplified modified nucleic acid molecules. The detectable number of amplified modified nucleic acid molecules are detected thereby detecting the nucleic acid.

In some embodiments, the nucleic acid is a DNA molecule. In other embodiments, the nucleic acid is an RNA molecule.

As described above, the nucleic acid includes a nucleic acid portion resistant to enzymatic modification or chemical modification. The nucleic acid portion may be an RNA portion or a DNA portion. Where a nucleic acid portion is resistant to enzymatic modification or chemical modification, the nucleic acid portion tends to be modified less than the remainder of the nucleic acid upon exposure to an enzymatic or chemical modifying agent. In some embodiments, the nucleic acid portion is protected (i.e. fully or partially protected) from enzymatic or chemical modification. For instance, the nucleic acid portion may be resistant to enzymatic modification or chemical modification due to, for example, being bound to a molecule or compound that protects the nucleic acid portion from an enzymatic modification or a chemical modification or forming part of an intramolecular tertiary structure that limits exposure to the enzymatic or chemical modifying agent. In some embodiments, the nucleic acid portion is bound to, or encompassed by, a protein (e.g. a ribosome) or another nucleic acid molecule (e.g., a nucleic acid having sufficient sequence complementarity to hybridize to the nucleic acid portion). The nucleic acid portion may be any appropriate length including, for example, a length of 2, 5, 10, 20, 30, 40, 50, 60, 70, 80, 90, 100, 250, 500, 1000 or more nucleotides in length.

The term "ribosome," as used herein, refers to one or more proteins typically forming at least part of a ribosomal complex of proteins involved in translational protein (or peptide) synthesis. Thus, where a method is provided for detecting an RNA molecule bound to at least one ribosome, the at least one ribosome may be at least one protein (ribosomal protein) associated with a ribosomal complex or at least one ribosomal complex.

The term "enzymatic modification," as used herein, refers to modification using an enzymatic modifying agent. An "enzymatic modifying agent" refers to an enzyme capable of catalyzing a change in the chemical structure of a nucleic acid or other reagent. Enzymatic modifying agents include, for example, kinases (e.g., polynucleotide kinase), phosphatases (e.g., alkaline phosphatase), phosphodiesterases (e.g., endonucleases and exonucleases), methyltransferases, and ligases.

In some embodiments, the enzymatic modifying agent is an enzymatic degradant. An "enzymatic degradant," as used herein, refers to an enzyme (i.e., a biomolecule such as a protein or nucleic acid that catalyzes a chemical reaction) capable of modifying a nucleic acid such that nucleic acid is shortened in length. In some embodiments, the enzymatic degradant is a phosphodiesterases such as an endonucleases or exonucleases. Where the nucleic acid is a deoxyribonucleic acid, the enzymatic degradant may be a deoxyribonuclease (DNase). Likewise, where the nucleic acid is a ribonucleic acid, the enzymatic degradant may be a ribonuclease (RNase). Numerous types of DNase and RNase may be employed depending upon the desired characteristic such as substrate specificity and cofactor requirements. In some embodiments, the DNase is DNase I and the RNase is RNase I (e.g., *E. coli* RNase I). Other useful enzymatic degradants include Exonuclease III, Mung Bean Nuclease, Nuclease BAL 31, Nuclease S1, Ribonuclease A (RNase A), Ribonuclease T1 (RNase T1) or combinations thereof (e.g., RNase A and RNase T1).

The term "chemical modification," as used herein, refers to modification using a chemical modifying agent. A "chemical modifying agent" refers to a compound or chemical, that is not an enzyme, capable of chemically reacting with a nucleic acid thereby changing the chemical structure of the nucleic acid. Chemical modifying agents include, for example reactive oxidative species, alkylating reagents, thiol cleavage reagents (e.g., Cu(II) with a thiol), N-phosphoryl histidine, diazonium salts, and the like. In some embodiments, the chemical modifying agent is a chemical degradant. A "chemical degradant," as used herein, refers to a non-enzyme chemical or compound capable of modifying a nucleic acid such that nucleic acid is shortened in length. Useful chemical degradants include, for example, thiol cleavage reagents (e.g., Cu(II) with a thiol), N-phosphoryl histidine, diazonium salts, Zn(II), hydroxide ion (under alkaline conditions) and the like. In some embodiments, the chemical modifying agent is methylsulfinylmethane, N-methylisatoic anhydride and derivatives thereof.

In some embodiments, detection of the amplified nucleic acid molecules includes sequencing. In some embodiments, the sequencing includes immobilizing the nucleic acid on a flow cell surface. Where applicable, the methods may include the sequencing methods described herein, including but not limited to, sequencing by synthesis. Thus, in some embodiments the nucleic acid is immobilized on a flow cell or microarray and subjected to the procedures described herein or known in the art for sequencing. Bridge amplification may occur within a flow cell having immobilized nucleic acids thereon, or within a microarray. In some embodiments, the microarray includes a plurality of assay wells having a population of microbeads randomly distributed thereon. In some embodiments, the nucleic acid is immobilized on the microbeads, which in turn are affixed to the microarray.

In some embodiments, the sequencing is accomplished using a sequencing-by-synthesis technique. The term "sequencing by synthesis" refers to the sequencing of a nucleic acid sequence by synthesis of the complementary strand, as known in the art and described herein. The sequence by synthesis technique may be selected from the group consisting of pyrosequencing, sequencing by ligation and sequencing by extension. The term "pyrosequencing," as known in the art, refers to a method of sequencing by synthesis which relies on detection of pyrophosphate release on nucleotide incorporation. See e.g., Ronaghi et al., *Science* 1998, 281:363; Ronaghi et al., *Anal. Biochem.* 242:84; Nyren et al., *Methods Mol. Biology.*, 2007, 373:1-14. The term "sequencing by ligation" refers to a DNA sequencing method that uses DNA ligase, as known in the art, to identify the nucleotide present at a given position in a DNA sequence. The term "sequencing by extension" refers to a DNA sequencing method wherein a primer is extended with a known or detectable nucleotide, as known in the art.

As described herein, the present methods can be used in conjunction with a variety of sequencing techniques. In some embodiments, the process to determine the nucleotide sequence of a target nucleic acid can be an automated process.

Templates (e.g., nucleic acids and fragments thereof) may be amplified on beads, for example using emulsion PCR methods. In order to use emulsion based amplification techniques with a single template per emulsion bubble, a single primer is attached to the bead, and a single primer is in solution, thereby amplifying the templates such that one end of the duplex is attached to the bead. The hybridized strand can be removed by denaturing the duplex, thereby leaving the immobilized single strand on the bead. The single stranded templates can be captured onto a surface via primers complementary to the templates. Exemplary emulsion-based amplification techniques that can be used in a method of the invention are described in US 2005/0042648; US 2005/0079510; US 2005/0130173 and WO 05/010145, each of which is incorporated herein by reference in its entirety and for all purposes.

Templates can be amplified on a surface using bridge amplification to form nucleic acid clusters. Bridge amplification gives a double stranded template where both ends are immobilized. Methods of generating nucleic acid clusters for use in high-throughput nucleic acid technologies have been described, as noted above. See, for example, U.S. Pat. No. 7,115,400, U.S. Patent Application Publication Nos. 2005/0100900 and 2005/0059048, and PCT Publication Nos. WO 98/44151, WO 00/18957, WO 02/46456, WO 06/064199, and WO 07/010,251, each of which is incorporated by reference herein in its entirety and for all purposes.

Some embodiments include sequencing by synthesis (SBS) techniques. SBS techniques generally involve the enzymatic extension of a nascent nucleic acid strand through the iterative addition of nucleotides or oligonucleotides against a template strand. In traditional methods of SBS, a single nucleotide monomer may be provided to a target nucleotide in the presence of a polymerase in each delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other. For example, the different nucleotides present in a sequencing reagent can have different labels and they can be distinguished using appropriate optics as exemplified by the sequencing methods developed by Solexa (now Illumina, Inc.).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1):84-9; Ronaghi, M. (2001) "Pyrosequencing sheds light on DNA sequencing." *Genome Res.* 11(1):3-11; Ronaghi, M., Uhlen, M. and Nyren, P. (1998) "A sequencing method based on real-time pyrophosphate." *Science* 281(5375):363; U.S. Pat. Nos. 6,210,891; 6,258,568 and 6,274,320, the disclosures of which are incorporated herein by reference in their entireties and for all purposes). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. Nos. 7,427,67, 7,414,163 and 7,057,026, the disclosures of which are incorporated herein by reference and for all purposes. This approach is being commercialized by Solexa (now Illumina Inc.), and is also described in WO 91/06678 and WO 07/123,744 (filed in the United States patent and trademark Office as U.S. Ser. No. 12/295,337), each of which is incorporated herein by reference in their entireties and for all purposes. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In particular embodiments some or all of the nucleotide monomers can include reversible terminators. In such embodiments, reversible terminators/cleavable fluors can include fluor linked to the ribose moiety via a 3' ester linkage (Metzker, *Genome Res.* 15:1767-1776 (2005), which is incorporated herein by reference and for all purposes). Other approaches have separated the terminator chemistry from the cleavage of the fluorescence label (Ruparel et al., *Proc Natl Acad Sci USA* 102: 5932-7 (2005), which is incorporated herein by reference in its entirety and for all purposes). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties and for all purposes.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010,251, the disclosures of which are incorporated herein by reference in their entireties and for all purposes.

Some embodiments can utilize sequencing by ligation techniques. Such techniques utilize DNA ligase to incorporate nucleotides and identify the incorporation of such nucleotides. Example ligation-based systems and methods which can be utilized with the methods and systems described herein are described in U.S. Pat. Nos. 6,969,488, 6,172,218, and 6,306,597, the disclosures of which are incorporated herein by reference in their entireties and for all purposes.

Some embodiments can utilize nanopore sequencing (Deamer, D. W. & Akeson, M. "Nanopores and nucleic acids: prospects for ultrarapid sequencing." *Trends Biotechnol.* 18:147-151 (2000); Deamer, D. and D. Branton, "Characterization of nucleic acids by nanopore analysis". *Acc. Chem. Res.* 35:817-825 (2002); Li, J., M. Gershow, D. Stein, E.

Brandin, and J. A. Golovchenko, "DNA molecules and configurations in a solid-state nanopore microscope" *Nat. Mater.* 2:611-615 (2003), the disclosures of which are incorporated herein by reference in their entireties and for all purposes). In such embodiments, the target nucleic acid or nucleotides released from the target nucleic acid pass through a nanopore. The nanopore can be a synthetic pore or biological membrane protein, such as α-hemolysin. As the target nucleic acid or nucleotides pass through the nanopore, each base-pair (or base) can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53:1996-2001 (2007); Healy, K. "Nanopore-based single-molecule DNA analysis." *Nanomed.* 2:459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130:818-820 (2008), the disclosures of which are incorporated herein by reference in their entireties and for all purposes).

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference in their entireties and for all purposes) or nucleotide incorporations can be detected with zero-mode waveguides as described, for example, in U.S. Pat. No. 7,315,019 (which is incorporated herein by reference in its entirety and for all purposes) and using fluorescent nucleotide analogs and engineered polymerases as described, for example, in U.S. Pat. No. 7,405,281 and U.S. Patent Application Publication No. 2008/0108082 (each of which is incorporated herein by reference in their entireties and for all purposes). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299:682-686 (2003); Lundquist, P. M. et al. "Parallel confocal detection of single molecules in real time." *Opt. Lett.* 33:1026-1028 (2008); Korlach, J. et al. "Selective aluminum passivation for targeted immobilization of single DNA polymerase molecules in zero-mode waveguide nanostructures." *Proc. Natl. Acad. Sci. USA* 105:1176-1181 (2008), the disclosures of which are incorporated herein by reference in their entireties and for all purposes). In one example single molecule, real-time (SMRT) DNA sequencing technology provided by Pacific Biosciences Inc. can be utilized with the methods described herein. In some embodiments, a SMRT chip or the like may be utilized (U.S. Pat. Nos. 7,181,122, 7,302,146, 7,313,308, incorporated by reference in their entireties and for all purposes). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about $1 \times 10^{-21}$ L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J. et al., "Long, processive enzymatic DNA synthesis using 100% dye-labeled terminal phosphate-linked nucleotides." *Nucleosides, Nucleotides and Nucleic Acids,* 27:1072-1083, 2008; incorporated by reference in its entirety and for all purposes). The label is cleaved from the nucleotide monomer on incorporation of the nucleotide into the polynucleotide. Accordingly, the label is not incorporated into the polynucleotide, increasing the signal:background ratio. Moreover, the need for conditions to cleave a label from a labeled nucleotide monomers is reduced.

An additional example of a sequencing platform that may be used in association with some of the embodiments described herein is provided by Helicos Biosciences Corp. In some embodiments, TRUE SINGLE MOLECULE SEQUENCING (tSMS)™ can be utilized (Harris T. D. et al., "Single Molecule DNA Sequencing of a viral Genome" *Science* 320:106-109 (2008), incorporated by reference in its entirety and for all purposes). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomer, namely, A, C, G, or T, are delivered one at a time to the target nucleic acid in the presence DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

An additional example of a sequencing platform that can be used in association with the methods described herein is provided by Complete Genomics Inc. Libraries of target nucleic acids can be prepared where target nucleic acid sequences are interspersed approximately every 20 by with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is delivered to the target nucleic acid in the presence of ligase.

The sequencing methods described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

In some embodiments, the sequencing further includes bridge amplification. The term "bridge amplification" refers to a solid phase replication method in which primers are bound to a solid phase, e.g., flow cell, microarray, and the like. The term "bridge" in this context refers to the fact that during the annealing step, the extension product from one bound primer forms a bridge to the other bound primer. All amplified products are covalently bound to the surface, and can be detected and quantified without electrophoresis. Sequencing by synthesis methods may be employed with any appropriate amplification method, including for example PCR. In some embodiments, the sequencing is accomplished using deep sequencing.

As described above, a modified nucleic acid is a nucleic acid whose chemical structure has been modified by an enzymatic or chemical modifying agent. The modified nucleic acid may be the product of enzymatic or chemical degradation. Thus, in some embodiments, the modified nucleic acid is a nucleic acid fragment of the nucleic acid molecule exposed or contacted with the enzymatic or chemical degradant. The nucleic acid fragment may include the nucleic acid portion or may itself be the nucleic acid portion resistant to enzymatic degradant or chemical degradant.

Methods for amplification of nucleic acids are well known in the art. Any appropriate method of amplification may be used in conjunction with the methods disclosed herein. For example, a useful amplification technique is PCR (polymerase chain reaction). Methods of PCR include basic PCR (Saiki et al., Science 1985, 230:1350-1354), real-time PCR (RT-PCR) (Nanashima et al., *J. Biol. Chem.* 2008, 283: 16868-16875), hot-start PCR (Carothers et al., *Biotechniques* 1989, 7:494-9 1989; Krishnan et al. *Nucl. Acids Res.* 1991, 19:1153; Clark, *Nucl. Acids Res.* 1988, 16:9677-86; Lin & Jayasena, *J. Mol. Biol.* 1997, 271:100-11; Dang & Jayasena, *J. Mol. Biol.* 1996, 264:268-78; Scalice et al. *J. Immunol. Methods,* 1994, 172:147-63; Sharkey et al., *Biotechnology* 1994, 12:506-9; Moretti, T. et al., *BioTechniques* 1998, 25:716-22), long PCR (Barnes, *Proc. Natl. Acad. Sci. USA* 1994, 91:2216-20), quantitative endpoint PCR (Gaudette & Crain, *Nucl. Acids Res.* 1991, 19:1879-84; Murphy et al., *Biochemistry* 1990, 29:10351-10356), quantitative real-time PCR (Lee et al., *Nucl. Acids Res.* 1993, 21:3761-3766; Bernard et al., *Anal. Biochem.* 1998, 255:101-107; Sherrill et al., *J. Am. Chem. Soc.* 2004, 126:4550-4556; Frackman et al., *Promega Notes* 2006, 92:10-13); rapid amplified polymorphic DNA analysis (McClelland & Welsh, *PCR Methods Appl.* 1994, 4:S59-65; Power, *J. Hosp. Infect.* 1996, 34:247-265; Black, 1993), rapid amplification of cDNA ends (Troutt et al., *Proc. Natl. Acad. Sci. USA* 1992, 89:9823-9825; Edwards et al., *Methods in Molecular Biology* (Vol. 15), White, B. A., ed., Humana Press, Totowa, N.J., 1991; Liu & Gorovsky, *Nucl. Acids Res.* 1993, 21:4954-60; Fromont-Racine et al., *Nucl. Acids Res.* 1993, 21:1683-1684), differential display PCR (Liang & Pardee, *Science* 1992, 257:967-71), in situ PCR (Haase et al., *Proc. Natl. Acad. Sci. USA* 1990, 87:4971-4975), and high fidelity PCR (Cline et al., *Nucl. Acids Res.* 1996, 24:3546-3551).

As described herein, nucleic acid molecules can be amplified on beads, for example using emulsion PCR methods. Exemplary emulsion-based amplification techniques that can be used in a method disclosed herein are described in US 2005/0042648; US 2005/0079510; US 2005/0130173 and WO 05/010145, each of which is incorporated herein by reference in its entirety and for all purposes. As further described herein, nucleic acid molecules can be amplified on a surface using bridge amplification to form nucleic acid clusters. Exemplary methods of generating nucleic acid clusters for use in high-throughput nucleic acid technologies have been described. See, for example, U.S. Pat. No. 7,115,400, U.S. Patent Application Publication Nos. 2005/0100900 and 2005/0059048, and PCT Publication Nos. WO 98/44151, WO 00/18957, WO 02/46456, WO 06/064199, and WO 07/010,251, each of which is incorporated by reference herein in its entirety and for all purposes.

In some embodiments, a method for detecting an RNA molecule bound to at least one ribosome is provided. The method includes contacting the RNA molecule with an enzymatic degradant or chemical degradant thereby forming an RNA fragment. The RNA fragment includes an RNA portion protected from the enzymatic degradant or the chemical degradant by a ribosome to which the RNA portion is bound. The RNA fragment is contacted with a DNA polymerase and a DNA polymerase primer thereby forming a linear DNA. The linear DNA is contacted with a ligase thereby forming a circularized DNA. The circularized DNA is amplified thereby forming a detectable number of amplified DNA molecules. The detectable number of amplified DNA molecules is detected thereby detecting the RNA bound to at least one ribosome.

In some embodiments, the at least one ribosome is a plurality of ribosomes. In some embodiments, the plurality of ribosomes is two or more proteins associated with a single ribosomal complex. In other embodiments, the plurality of ribosomes may be a plurality proteins associated with a plurality of different ribosomal complexes. In other embodiments, the at least one ribosome is at least one protein associated with a ribosomal complex. In other embodiments, the at least one ribosome is at least one ribosomal complex.

In some embodiments of the methods provided herein, where a method includes contacting an RNA molecule (e.g. an RNA fragment) with a DNA polymerase, the method further includes treating the RNA molecule (e.g. an RNA fragment) thereby providing a binding site for the DNA polymerase primer. For example, an RNA is extended thereby providing a site for hybridization (either full or partial hybridization) of the DNA polymerase primer. In some embodiments, the RNA molecule (e.g. an RNA fragment) is extended using a polymerase (e.g. a poly(A)-polymerase) thereby providing a binding site for the DNA polymerase primer.

In other embodiments, a method is provided for detecting a plurality of RNA molecules bound to at least one ribosome. The method includes contacting the plurality of RNA molecules with an enzymatic degradant or a chemical degradant thereby forming a plurality of RNA fragments. Each RNA fragment includes an RNA portion protected from the enzymatic degradant or the chemical degradant by a ribosome to which the RNA portion is bound. The RNA fragments are amplified to form a detectable number of amplified nucleic acid fragment. The detectable number of amplified nucleic acid fragments are detected thereby detecting said plurality of RNA molecules bound to at least one ribosome. As described above, the RNA fragment may include the RNA portion or may be the RNA portion (i.e. the RNA fragment is co-extensive with the RNA portion). In some embodiments, each of the RNA molecules has an identical base sequence. In some embodiments, the at least one ribosome is a plurality of ribosomes. In some embodiments, the plurality of ribosomes is two or more proteins associated with a single ribosomal complex. In other embodiments, the plurality of ribosomes may be a plurality proteins associated with a plurality of different ribosomal complexes.

In some embodiments, the methods provided herein may be performed using nucleic acid derived from a cell. The cell may be any appropriate cell, include a bacterial cell or a eukaryotic cell and including, but not limited to, animal cells, fungal cells and plant cells. In some embodiments, the cell is a mammalian cell, such as a human cell or a cell from a domesticated animal (e.g. dog, cat, horse etc.) or a livestock animal (e.g., pig, cow etc.). In some embodiments, the cell forms part of an organ or an organism. The cell may also be obtained from an organism that is diseased to assess characteristics of a disease state. Thus, in some embodiments, the cell is or has been infected with a virus. In other embodiments, the cell is derived from an organism with a disease (e.g., diabetes, heart disease, Alzheimer's disease, etc.).

The nucleic acid may be obtained from a cell using techniques known in the art. Typically, the cell is lysed and the nucleic acid is recovered using known nucleic acid purification techniques. As described herein, in some embodiments, the nucleic acid is a plurality of nucleic acids, such as a plurality of RNA molecules. Thus, in some embodiments, the nucleic acid detected (e.g., RNA molecules) form part of a cell. Thus, a method set forth herein may further include lysing the cell, thereby providing the plurality of nucleic acids (e.g., RNA molecules).

In some embodiments, the methods provided herein further include, as appropriate, isolating nucleic acid (e.g., RNA) molecules from a cell. The plurality of RNA molecules may include at least, for example 10%, 25%, 50%, 70%, 75%, 80%, 85%, 90%, 95%, 99%, or even more of the mRNA sequence species from the cell. Thus, in some embodiments, the method further includes isolating the plurality of RNA molecules from a cell. And in some embodiments of the methods provided herein, the plurality of RNA molecules comprise at least 1,000, for example, 10,000; 50,000; 100,000, 200,000; 300,000 or more, different sequence species.

In some embodiments as appropriate, the methods provided herein further include determining the amount of each nucleic acid fragment (e.g., RNA fragment), thereby determining the amount of each nucleic acid portion (e.g., RNA portion). The amount of each nucleic acid fragment (e.g., RNA fragment) can be an absolute amount or a relative amount such as an amount relative to a control (e.g., a known amount of RNA in a cell or in vitro, such as an RNA coding for a housekeeping protein). Typically, where the amount is compared to or is relative to a control, the amount of a control is determined prior to performing the methods described herein using known techniques in the art. Accordingly, in some embodiments the amount of each RNA fragment is determined relative to the amount of a control.

In some embodiments as appropriate, the methods provided herein further include contacting the plurality of nucleic acid (e.g., RNA) molecules with a phosphatase prior to contacting with an enzymatic degradant or a chemical degradant, thereby forming a free 3'-hydroxyl terminus. In some embodiments, the method further includes extending the 3' end of the plurality of nucleic acid molecules (e.g., RNA molecules) after formation of the free 3' hydroxyl terminus. In some embodiments, the extending of the nucleic acid (e.g., RNA) includes polyadenylation. In some embodiments, the polyadenylation employs E. coli poly-(A) polymerase.

In some embodiments as appropriate, the methods provided herein further include quantifying the amount of two or more of the nucleic acid (e.g., RNA) portions. The quantification can be absolute, wherein the absolute amount of the two or more nucleic acid (e.g., RNA) portions is determined. Alternatively, the quantification can be relative, wherein the amount of the one or more nucleic acid (e.g., RNA portions) is determined relative to the amount of another nucleic acid (e.g., RNA) portion such as a control amount. In some embodiments, the two or more nucleic acid (e.g., RNA) portions is at least 10, 100, 1000, 10,000, 50,000, 100,000, 500,000 or 1,000,000 different nucleic acid (e.g., RNA) portions. In other embodiments, the two or more nucleic acid (e.g., RNA) portions is 10, 100, 1000, 10,000, 50,000, 100,000, 500,000 or 1,000,000 different nucleic acid (e.g., RNA) portions.

In some embodiments, where the nucleic acid molecule detected is an RNA molecule, the amount of two or more RNA portions are correlated to an amount of ribosomal activity or translation activity on one or more RNA molecules. In some embodiments, the amount of two or more RNA portions are correlated to an amount of protein synthesis from one or more RNA molecules. In some embodiments, the amount of two or more RNA portions are correlated to a rate of translation of one or more RNA molecules. In some embodiments, the amount of two or more RNA portions are correlated to locations for boundaries of translated sequences. In some embodiments, the locations for boundaries of translated sequences include the boundaries of coding sequences at sub-codon precision. The term "sub-codon precision" refers to sequence data having sufficient precision to determine the sequence thereof. For example, sub-codon precision can include identification of a location in a sequence at a resolution of one or two nucleotide positions in the sequence. In some embodiments, the amount of two or more RNA portions are correlated to reading frame translation. Where applicable, in some embodiments relating to quantifying the amount of two or more of the RNA portions, the methods include the detection and quantitation methods described herein and known in the art.

In some embodiments, the method of detecting is sequencing. In some embodiments, the sequencing includes immobilizing the nucleic acid on a flow cell surface. In some embodiments, the sequencing further includes bridge amplification. Applicable sequencing methods are described above and are equally applicable, where appropriate, to all the methods described herein.

In some embodiments as appropriate, the methods provided herein further include contacting the plurality of RNA fragments with a DNA polymerase and a DNA polymerase primer thereby forming a plurality of linear DNA molecules. The plurality of linear DNA molecules is contacted with a ligase thereby forming a plurality of circularized DNA molecules. The plurality of circularized DNA molecules are amplified thereby forming a detectable number of amplified DNA molecules. The detectable number of amplified DNA molecules are detected thereby detecting the plurality of RNA molecules (e.g., RNA molecules bound to at least one ribosome). In some embodiments, the primer includes a DNA linker attached to the 3' end of the primer.

Amplification techniques are described above and are equally applicable, as appropriate, to any of a variety of the methods provided herein. Thus, in some embodiments, the amplifying step performed in the methods provided herein is a polymerase chain reaction. In some embodiments, the detecting step performed in the methods provided herein includes contacting the amplified nucleic acid fragments with a microarray. In some embodiments of the methods provided herein, the microarray is an optical fiber microarray or a silicon wafer microarray. In some embodiments of the methods provided herein, the microarray is an optical fiber microarray. In some embodiments of the methods provided herein, the microarray is a silicon wafer microarray. In some embodiments of the methods provided herein, the microarray includes a plurality of assay wells having a population of microbeads randomly distributed thereon.

In some embodiments of the methods provided herein, the amplified nucleic acid fragments include a detectable label. The detectable label may be a fluorophoric dye. In some embodiments of the methods provided herein, the detecting further includes allowing a fluorophoric dye labeled duplex to form, and detecting the fluorophoric dye labeled duplex.

In some embodiments, the microarray employed in the methods provided herein includes a nucleic acid having at least 70%, 75%, 80%, 85%, 90%, 95%, 99% or even higher complementary to at least one of the amplified nucleic acid (e.g., DNA) molecules. In some embodiments, the nucleic acid is at least 90% or 95% complementary to at least one of the amplified nucleic acid (e.g. DNA) molecules.

As described above, the methods provided herein may use an enzymatic degradant. The enzymatic degradants described above are equally applicable, as appropriate, to all of the methods provided herein. Thus, in some embodiments, the enzymatic degradant is an RNase.

In some embodiments of the methods provided herein, the RNA portion is bound to the ribosome by a chemical cross-linking agent. Methods and reagents for cross-linking RNA to ribosomes are well known in the art. Thus, any applicable cross-linking reagent known to be useful for cross-linking ribosomes to RNA may be used in the methods provided herein as appropriate.

In other embodiments of the methods provided herein, the RNA portion is bound to the ribosome wherein the ribosome has been immobilized (i.e., the translational function of the ribosome has been stopped or significantly decreased) by a translational immobilization reagent (i.e., a reagent that halts or significantly decreases protein biosynthesis). Any appropriate translational immobilization reagent may be employed, including but not limited to cycloheximide.

In some embodiments of the methods provided herein, each of the nucleic acid (e.g., RNA) fragments are at least partially sequenced using a sequencing by synthesis technique to determine the nucleotide sequences of the nucleic acid (e.g., RNA) portions. Sequencing by synthesis techniques are described above and are equally applicable to all of the methods provided herein as appropriate. In some embodiments, the sequencing by synthesis technique is selected from the group consisting of pyrosequencing, sequencing by ligation and sequencing by extension.

In another aspect, there is provided a method for detecting a relative amount of translation of an RNA sequence. A plurality of RNA molecules is contacted with an enzymatic modifying agent or chemical modifying agent. Each of the plurality of RNA molecules includes an identical base sequence and is bound to a different ribosome, thereby forming a plurality of partially degraded RNA molecules. The plurality of partially degraded RNA molecules is contacted with a DNA polymerase and a DNA polymerase primer thereby forming a plurality of linear DNA molecules. The plurality of linear DNA molecules is contacted with a ligase thereby forming a plurality of circularized DNA molecules. The plurality of circularized DNA molecules is amplified thereby forming a detectable number of amplified DNA molecules. The detectable number of amplified DNA molecules is detected and quantified thereby detecting the amount of amplified DNA molecules. The amount of amplified DNA molecules is compared to a standard control, thereby detecting the relative amount of translation of said RNA sequence. As discussed above, in some embodiments, the method further includes treating the RNA fragment thereby providing a binding site for the DNA polymerase primer (e.g., the RNA fragment is extended using a polymerase (e.g., a poly(A)-polymerase) thereby providing a binding site for the DNA polymerase primer. In some embodiments, the different ribosomes are proteins forming parts or all of different ribosomal complexes.

In some embodiments, there is provided a method for determining translation activity for a plurality of RNA molecules. A plurality of RNA-ribosome complexes is treated, wherein each RNA-ribosome complex includes an RNA molecule having an RNA portion that is bound to a ribosome, under conditions sufficient produce a plurality of RNA fragments. Each RNA fragment includes an RNA portion. Each RNA fragment also includes a nucleotide sequence that is longer than the nucleotide sequence of the RNA portion. The plurality of RNA fragments is sequenced to determine the nucleotide sequences of the RNA portions. The nucleotide sequences of the plurality of RNA portions are then compared with the nucleotide sequences of the RNA molecules, thereby determining translation activity for the plurality of RNA molecules. An RNA-ribosome complex is an RNA that is bound to one or more proteins that forms at least part of a ribosomal complex.

The embodiments described above are equally applicable to the methods for determining translation set forth in the preceding two paragraphs as appropriate. For example, in some embodiments, the plurality of RNA-ribosome complexes is isolated from a cell and includes at least 10%, for example, 10%, 25%, 50%, 75%, 90%, 95%, 99% or even more, of the mRNA species from the cell. In some embodiments, the method further includes isolating the RNA molecules from a cell. The method may further include isolating the RNA-ribosome complexes from a cell. In some embodiments, the plurality of RNAs comprises at least 1,000 different sequence species, for example, at least 10,000; 50,000; 100,000, 200,000; 300,000, or even more. The RNA portion may be bound to the ribosome by a chemical cross-linking agent. The method may further include quantifying the relative amounts of two or more of the RNA portions in the RNA-ribosome complexes. In some embodiments, each of the RNA fragments are partially sequenced using a sequencing-by-synthesis technique to determine the nucleotide sequences of the RNA portions.

In some embodiments, the translation activity is a rate of translation for one or more RNA in the plurality of RNA-ribosome complexes. The translation activity may include the locations for boundaries of translated sequences. In some embodiments, the locations for boundaries of translated sequences is the boundaries of coding sequences at sub-codon precision. In some embodiments, the translation activity is the translation of the reading frame. In some embodiments, the primer includes a DNA linker attached to the 3' end of the primer. In some embodiments, detection is accomplished using deep sequencing. In some embodiments, detection includes contacting the amplified DNA molecules with a microarray. In some embodiments, detection further includes contacting the amplified DNA molecules with a microarray.

In one aspect, there is provided a method for detecting a relative amount of translation of an RNA sequence. A plurality of RNA molecules is contacted with an enzymatic modifying agent or chemical modifying agent, wherein each of the plurality of RNA molecules includes an identical base sequence and is bound to a different ribosome, thereby forming a plurality of partially degraded RNA molecules. The plurality of partially degraded RNA molecules is contacted with a DNA polymerase and a DNA polymerase primer thereby forming a plurality of linear DNA molecules. The plurality of linear DNA molecules is contacted with a ligase thereby forming a plurality of circularized DNA molecules. The plurality of circularized DNA molecules is amplified thereby forming a detectable number of amplified DNA molecules. The detectable number of amplified DNA molecules is detected and quantified thereby detecting the amount of amplified DNA molecules. As discussed above, in some embodiments, the method further includes treating the RNA fragment thereby providing a binding site for the DNA polymerase primer (e.g., the RNA fragment is extended using a polymerase (e.g., a poly(A)-polymerase) thereby providing a binding site for the DNA polymerase primer. In some embodiments, the different ribosomes are proteins forming parts or all of different ribosomal complexes.

Also provided herein are kits including components useful in practicing the methods disclosed herein. In some embodiments, the kit includes a DNA polymerase, a DNA polymerase primer (e.g., including a DNA linker attached to the 3' end of the primer), a ligase, and a phosphodiesterase. The kit may also include a chemical or enzymatic degradant. In some embodiments, the kit further includes instructions setting forth the steps recited in the methods disclosed herein.

The elements of one particular method disclosed herein are equally applicable, where appropriate, to the other disclosed methods and/or the kits provided herein. Further details regarding certain embodiments of the methods and kits described herein are set forth below.

Concomitant with the development of ribosome profiling for mammalian cells, simplified and optimized protocols have been developed. Such protocols are useful for smaller sized samples. In some embodiments, after nuclease digestion, ribosomes can be purified by sucrose density gradient fractionation. In some embodiments, ultracentrifugation to pellet ribosomes in a sucrose cushion can be employed. In some embodiments, filtration can also be used to recover ribosomes.

In some embodiments, a protocol (i.e., subtractive hybridization of contamination RNAs) can be employed to eliminate unwanted contaminating RNA sequences with minimal effects on the yield or the coverage of desired ribosome footprints. In some embodiments, a large fraction of the sample can consist of contaminating fragments of ribosomal RNA (rRNA). In some embodiments, complementary DNA oligonucleotides can be employed that can hybridize with these specific contaminating sequences. The targeting oligos can be biotinylated such that the hybridized contaminants can be removed with streptavidin-coated beads without affecting the rest of the sample. Using this procedure, thousands-fold depletion of specific targeted contamination sequences can be achieved that produces a substantial depletion of overall contamination, resulting in e.g., >50% footprint sequences.

In some embodiments, the drugs harringtonine (a cephalotaxine) and the like can be used to identify sites of translation initiation. This class of drug specifically immobilizes ribosomes that are initiating translation. In some embodiments which employ harringtonine, only footprints from translation start sites can be determined, as opposed to all regions of active translation. This method can be useful for detecting upstream open reading frames and annotating complex mammalian transcriptomes.

III. Examples

The following examples are meant to illustrate certain embodiments of the invention, and not to limit the scope of the inventions disclosed herein.

Experimental Methods

Extract and Total RNA Preparation 750 ml cultures were grown in YEPD to mid-log phase (OD600 of 0.6). Cycloheximide was added to a final concentration of 100 ug/ml and growth was continued for 2 min on a 30 C shaker. Cells were harvested by filtration onto 0.45 um pore size nitrocellulose filters.

The majority of the sample was resuspended in ice-cold polysome lysis buffer (20 mM Tris 8.0, 140 mM KCl, 1.5 mM $MgCl_2$, 100 ug/ml cycloheximide, 1% Triton) and dripped into liquid nitrogen. Frozen cells were pulverized for six cycles, each of 3 min, at 15 Hz on a Retsch mixer mill with the sample chamber chilled in liquid nitrogen. Pulverized cells were thawed and cell debris was clarified with a low-speed spin of 5 min, 3,000 g, 4 C. The supernatant was then spun 20 min, 20,000 g, 4 C and the soluble material beneath the buoyant membrane layer was recovered. Aliquots of this extract were flash-frozen in 1N2. Typical yields were 0.80 ml of extract with A260 of 400-500. A small amount of each sample was resuspended in ice-cold total RNA lysis buffer (10 mM EDTA, 50 mM NaOAc pH 5.5) and total RNA was purified by the standard hot phenol method. Typical yields were 1 mg of total RNA.

Ribosome Footprinting

An aliquot of 100 A260 units of extract was split into two equal parts. 750 U of *E. coli* RNase I was added to one, while 40 U of SUPERASE•IN™ RNase inhibitor (Ambion) was added to the other. The samples were incubated 1 hour at room temperature with gentle mixing.

Monosome Isolation 10-50% (w/v) sucrose gradients were prepared in polysome gradient buffer (20 mM Tris 8.0, 140 mM KCl, 5 mM $MgCl_2$, 100 ug/ml cycloheximide, 0.5 mM DTT, 20 U/ml SUPERASE•IN™) in Sw41 ultracentrifuge tubes using a BioComp gradient station. The digested and control samples were loaded on the gradients, which were spun for 3 hours at 35,000 rpm, 4 C in an Sw40 rotor in an ultracentrifuge. Gradients were fractionated in the BioComp gradient station as well, using a BioRad Econo UV monitor to record A260 during the fractionation. The monosome fraction was collected for both samples.

Footprint Fragment Isolation

RNA was extracted from the purified monosomes by the hot phenol method. The extracted RNA was loaded onto a YM-100 microconcentrator (Amicon) and spun to recover the flow-through, containing small RNAs including the ribosome footprint fragments as well as digested rRNA fragments. The flow-through was precipitated by NaOAc/isopropanol precipitation with GLYCOBLUE™ (Ambion) as a coprecipitant.

Random mRNA Fragment Preparation mRNA was recovered from 50 ug total RNA using magnetic oligo-dT DYNABEADS® (Invitrogen) according to the manufacturer's instructions. The purified mRNA was recovered in 20 ul 10 mM Tris 8. This was mixed with an equal volume of 2× alkaline fragmentation solution (2 mM EDTA, 10 mM Na2CO3, 90 mM NaHCO3) and incubated 20 min at 95 C. This was then mixed with 0.56 ml ice-cold stop/precipitation solution (300 mM NaOAc with GLYCOBLUE™ coprecipitant), followed by 0.60 ml ice-cold isopropanol. The RNA was precipitated by the standard technique, with final resuspension in 8.0 ul 10 mM Tris 8.

RNA Fragment Capture

RNA fragments derived from footprinting or from random mRNA fragmentation were dephosphorylated in a reaction with 1× T4 polynucleotide kinase buffer w/o ATP, 1 U SUPERASE•IN™, and 10 U T4 polynucleotide kinase (NEB). Dephosphorylation was carried out for 1 hour at 37 C, followed by heat inactivation for 10 min at 75 C. The dephosphorylation reactions were run on a denaturing 15% polyacrylamide TBE-urea gel (Invitrogen) and the 28 nt region was excised. The gel slices were physically disrupted and RNA was eluted by soaking overnight in gel elution buffer (300 mM NaOAc, 1 mM EDTA, 0.1 U/ul SUPERASE•IN™). The eluate was recovered and RNA was precipitated by the addition of isopropanol.

The recovered RNA was quantified using the Small RNA BioAnalyzer system (Agilent). A 20 pmol aliquot of RNA was briefly denatured, then used for poly-(A) tailing in 1× Poly(A) polymerase buffer, 0.8 U/ul SUPERASE•IN™, 120 uM ATP, with 5 U E. coli poly-(A) polymerase (NEB). The tailing reaction was carried out for 30 min at 37 C, at which point the ATP was exhausted.

Reverse transcription reactions were set up with 5 ul tailing reaction plus 570 nmol Tris 8, 8.2 nmol each dNTP, and 50 µmol T20VN anchoring primer in a total volume of 14.25 ul. The reaction was briefly denatured at 75 C, then equilibrated at 48 C, and 82 nmol DTT, 10 U SUPERASE•IN™, and 164 U SUPERSCRIPT® III (Invitrogen) were added. Reverse transcription was carried out for 30 min at 48 C. RNA was subsequently removed by addition of 1.8 ul of 1M NaOH and incubation at 98 C for 20 min. The reaction was neutralized with 1.8 ul of 1M HCl. The reactions were run on a denaturing 10% polyacrylamide TBE-urea gel. Extended first-strand cDNA products were excised, taking care to avoid unextended primer. The gel slices were physically disrupted and DNA was eluted by soaking overnight in gel elution buffer (300 mM NaCl, 1 mM EDTA). The eluate was recovered and DNA was precipitated by the addition of isopropanol.

Linker Addition by Circularization

Single-strand DNA was circularized in a 5 ul reaction with 1× CIRCLIGASE™ buffer, 50 mM ATP, and 2.5 mM MnCl2 along with 50 U CIRCLIGASE™ (Epicentre). Circularization was carried out for 1 hour at 60 C, followed by heat inactivation for 10 min at 80 C.

Circularized single-strand DNA was relinearized at an abasic site by supplementing the 5.0 ul circularization reaction with 6.25 ul relinearization supplement (50 mM KCl, 1 mM DTT) and 12.5 U APE 1 (NEB). The relinearization was carried out for 1 hour at 37 C. Relinearized products were gel purified in the same manner as reverse transcription products.

Relinearized ssDNA was used as a template for PCR using PHUSION® (NEB) according to the manufacturer's instructions. Reactions with 8 to 14 cycles were conducted and the products were run on a non-denaturing 8% polyacrylamide TBE gel. Amplification reactions were selected based on a high yield of the desired product with remaining oligos indicating that they had not reached saturation. DNA products of the appropriate size were excised from the gel and extracted as described above.

Ribosomal RNA Subtraction

Antisense, biotinylated DNA oligodeoxynucleotides ("oligos") can be used to pull out ribosomal RNA (rRNA) fragments. Such oligos useful in the methods described herein include, but are not limited to, those having the sequences provided herein. Such oligos can be stored in 100 µM stocks in RNase-free 10 mM Tris 7.0. Such oligos have a 5' biotin modification with the standard linker included from IDT (C6) and can be HPLC purified.

The first two subtraction oligos were designed based on preliminary experiments in human tissue culture cells, but the orthologous portion of the mouse rRNA has the same sequence. See Table 2.

TABLE 2

Subtraction antisense, biotinylated DNA oligodeoxynucleotides

| Entry | Description/sequence |
|---|---|
| 1 | oNTI269: NR_003287.1 @ 4103 to 4084 for subtraction<br>5'-/5Biosg/TGGCGCCAGAAGCGAGAGCC<br>(SEQ ID NO: 1) |
| 2 | oNTI270: NR_003285.2 @ 144 to 125 for subtraction<br>5'-/5Biosg/AGACAGGCGTAGCCCCGGGA<br>(SEQ ID NO: 2) |

The next four subtraction oligos were designed specifically for samples from mouse tissue culture cells based on preliminary experiments in which only oNTI269 and oNTI270 were used for subtraction. See Table 3.

TABLE 3

Additional subtraction antisense, biotinylated DNA oligodeoxynucleotides

| Entry | Description/sequence |
|---|---|
| 3 | oNTI291: NR_003279.1 @ 209 to 186<br>/5Biosg/GAT CAG AAG GAC TTG GGC CCC CCA<br>(SEQ ID NO: 3) |
| 4 | oNTI292: NR_003278.1 @ 316 to 287<br>/5Biosg/CGA TCG GCC CGA GGT TAT CTA GAG TCA CCA<br>(SEQ ID NO: 4) |
| 5 | oNTI293: NR_003278.1 @ 869 to 480<br>/5Biosg/TCC ATT ATT CCT AGC TGC GGT ATC CAG GCG<br>(SEQ ID NO: 5) |
| 6 | oNTI294: NR_003278.1 @ 752 to 734<br>/5Biosg/CCG AGA GGC AAG GGG CGG G<br>(SEQ ID NO: 6) |

The protocol is optimized for footprint mixtures containing up to 20 pmoles of RNA fragments of ~30 nt each (~150 ng). For this scale, experiments in yeast suggest that the subtraction removes 97-98% of three distinct rRNA targets with maximum background pulldown of ~5% (likely less). Sequencing of subtracted versus unsubtracted mRNA fragments revealed no discernable nonspecific pulldown or sample bias as a result of subtraction.

Without wishing to be bound by any theory, it is believed that subtracted samples cannot undergo poly-A-tailing.

Indeed, no clean-up protocol tested (e.g., precipitation, gel purification, phenol extraction or dialysis) was able to remove the inhibitory effect of this subtraction protocol on poly-A-tailing. Even mock subtracted RNA oligo showed the inhibition, and preliminary experiments indicate that the inhibition can act in trans, based on the observation that pure oligo spiked post-subtraction into a subtracted mixture tails poorly. Based on these observations, subtraction can be performed after poly-A-tailing, but before reverse transcription (RT). No inhibition of RT reactions was seen in subtracted samples, and sequencing results indicate that efficiency of subtraction was comparable at this step to what was seen in preliminary experiments in non-tailed fragments.

Reagents useful for oligo subtraction include the reagents provided in Table 4.

TABLE 4

Reagents useful for oligo subtraction.

| Entry | Description |
|---|---|
| A | Equimolar mix of subtraction oligos (final concentration 17 μM each) |
| B | MYONE ™ C1 dynabead B&W buffer 2X + 0.01% Tween<br>i. 10 mM Tris-HCl (pH 7.5)<br>ii. 1 mM EDTA<br>iii. 2M NaCl<br>iv. 0.01% Tween |
| C | MYONE ™ C1 dynabead B&W buffer 1X + 0.01% Tween<br>i. 5 mM Tris-HCl (pH 7.5)<br>ii. 500 M EDTA<br>iii. 1M NaCl<br>iv. 0.01% Tween |
| D | MYONE ™ C1 dynabead Solution A<br>i. 0.1 M NaOH<br>ii. 0.05 M NaCl |
| E | MYONE ™ C1 dynabead Solution B<br>i. 0.1 M NaCl |

A typical oligo subtraction protocol includes, but is not limited to, the following steps. See Table 5.

TABLE 5

Typical oligo subtraction protocol.

| Step | Description |
|---|---|
| 1 | Begin with 25 μl poly-(A) tailing reaction stopped with EDTA |
| 2 | Add:<br>a. 3.2 μl 20X SSC (saline sodium citrate, RNase-free)<br>b. 3.0 μl subtraction oligo mixture |
| 3 | Incubate 3 minutes at 70° C. |
| 4 | Transfer rapidly to 37° C., add 1 μl SUPERASE•IN ™, and incubate 30 minutes |
| 5 | Prepare MYONE ™ Streptavidin C1 dynabeads as follows in a non-stick tube:<br>a. Vortex MYONE ™ C1 streptavidin dynabeads<br>b. Take 150 μl beads per sample to subtract<br>c. Wash 3x in 150 μl B&W buffer 1x + 0.01% Tween<br>d. Wash 2x in 150 μl Solution A<br>e. Wash 2x in 150 μl Solution B<br>f. Resuspend in 32 μl B&W buffer 2X + 0.01% Tween<br>g. Equilibrate beads at 37° C. in Eppendorf ThermoMixer ® |
| 6 | Add RNA sample to dynabeads |
| 7 | Incubate at RT 15 minutes with low shaking (~400 rpm in Eppendorf ThermoMixer) |
| 8 | Place tube on magnet, wait 30 s, and remove supernatant (~65 l to a new non-stick tube) |
| 9 | Add:<br>a. 8 μl 3M Sodium Acetate pH 5.5<br>b. 1 μl GLYCOBLUE ™ |
| 10 | Mix, then add 100 μl isopropanol |
| 11 | Place at −20° C. for at least 30 minutes |
| 12 | Spin at 4° C. 20000 xG for 30 minutes |

TABLE 5-continued

Typical oligo subtraction protocol.

| Step | Description |
|---|---|
| 13 | Remove supernatant with pipette |
| 14 | Pulse spin to collect residual liquid and remove all liquid |
| 15 | Remove supernatant carefully and air dry pellet for 5-10 minutes |

Mammalian Footprinting

This protocol describes the process of generating ribosome footprints from mammalian tissue culture cells, as opposed to yeast. After nuclease digestion, monosomes are purified by pelleting through a sucrose cushion rather than by sucrose density gradient fractionation. This purification could be used in yeast samples as well. It also describes treatment of cells with harringtonine in order to footprint translation initiation rather than translation elongation. Harringtonine, as known in the art, is an alkaloid from Cephalotaxus which inhibits proteins biosynthesis. Without wishing to be bound by any theory, it is believed that harringtonine inhibits initiation of protein synthesis.

Buffers

Mammalian Polysome Buffer. This buffer is adapted taken from Johannes G et al., *Proc Natl Acad Sci USA* 96:13118 (1999). It contains higher salt and higher magnesium than the yeast polysome buffer. See Table 6.

TABLE 6

Mammalian polysome buffer.

| Buffer | for 40 mL |
|---|---|
| 20 mM Tris pH 7.4 | 400 uL 1 M Tris pH 7.0 |
|  | 400 uL 1 M Tris pH 8.0 |
| 250 mM NaCl | 2000 uL 5M NaCl |
| 15 mM MgCl$_2$ | 600 uL 1 M MgCl$_2$ |
| 100 ug/mL cycloheximide | 80 uL 50 mg/mL cycloheximide in EtOH |
| 1 mM DTT | 40 uL 1M DTT |
|  | 36.5 mL DEPC-treated water |

Lysis Buffer. 250 ul 20% Triton and 4.75 ml polysome buffer.

Sucrose Cushion. 1.7 g sucrose dissolved in 3.9 mL polysome buffer, to a final volume of 5.0 ml. Add 25 ul SUPERASE•IN™ at 20 U/uL.

Lysate Preparation

Each sample requires on 150 mm dish, corresponding to roughly 6_107 cells, with 25 ml media.

Drug Treatment

A drug treatment protocol useful for mammalian footprinting is provided in Table 7 following.

TABLE 7

Drug treatment protocol for mammalian footprinting.

| Step | Description |
|---|---|
| 1 | To footprint translation initiation, add harringtonine to a final concentration of 1 uM (from a 1 mg/ml stock in DMSO). Swirl to mix and return the dish to 37° C. for 10 minutes. |
| 2 | Add cycloheximide to a final concentration of 100 ug/mL (from a 500 x, 50 mg/mL stock in EtOH). |
| 3 | Swirl to mix and return the dish to 37° C. for 1 minute. |

Lysate Preparation

Preparation of Lysate for Mammalian Footprint can be Conducted by the Protocol provided in Table 8 following.

TABLE 8

Protocol for lysate preparation for mammalian footprinting.

| Step | Description |
|---|---|
| 1 | Remove dish from incubator, aspirate all media, and place on ice at a slight angle. |
| 2 | Drip on 10 ml ice-cold 1x PBS + cycloheximide (100 ug/mL), swirl to rinse, and aspirate all PBS from the lower corner of the dish. |
| 3 | Repeat the PBS + cycloheximide wash, taking extra time to allow all residual liquid to collect and tipping the dish. |
| 4 | Drip on 0.80 mL lysis buffer, ensuring that the entire dish is covered. |
| 5 | Agitate gently, then scrape cells and lysis buffer to the lower corner of the dish. Pipette lysis buffer from the bottom of the dish back to the top and re-scrape if needed. |
| 6 | Trituate cells in lysis buffer by pipetting up and down many times, then remove all liquid to a 1.5 ml microfuge tube on ice. This is typically 1.2 to 1.4 ml. |
| 7 | Incubate 10 min on a 4° C. roller. |
| 8 | Spin 10 min at 20,000 x G, 4° C. to clarify the lysate. |
| 9 | Remove the supernatant, avoiding both the pellet and any buoyant membrane debris, to a new 1.5 ml microfuge tube on ice. |

Footprinting

Footprinting of mammalian sample can be conducted using the protocol provided in Table 9 following.

TABLE 9

Protocol for mammalian footprinting.

| Step | Description |
|---|---|
| 1 | Take 500 ul lysate with 12.5 uL RNase I at 100 U/muL. |
| 2 | Incubate 45 min on room temperature roller. |
| 3 | Quench digestion by adding 25 ul SUPERASE•IN ™ (20 U/uL) and placing on ice. |
| 4 | Add 1.0 mL sucrose cushion to a 13 mm x 56 mm thick-wall polycarbonate ultracentrifuge tube. |
| 5 | Layer on footprinting digestion. |
| 6 | Spin 4 hours at 70,000 rpm, 4° C. in a TLA-110 ultracentrifuge rotor. |
| 7 | Mark the top of each tube at the point distal from the center of the rotor, where the pellet will form. |
| 8 | Remove all supernatant, leaving behind a glassy ribosome pellet. |
| 9 | Resuspend the pellet in 600 uL 10 mM Tris 7 by persistent pipetting and physical disruption of the pellet. |

Quantifying Translation by Deep Sequencing

Figure 7:
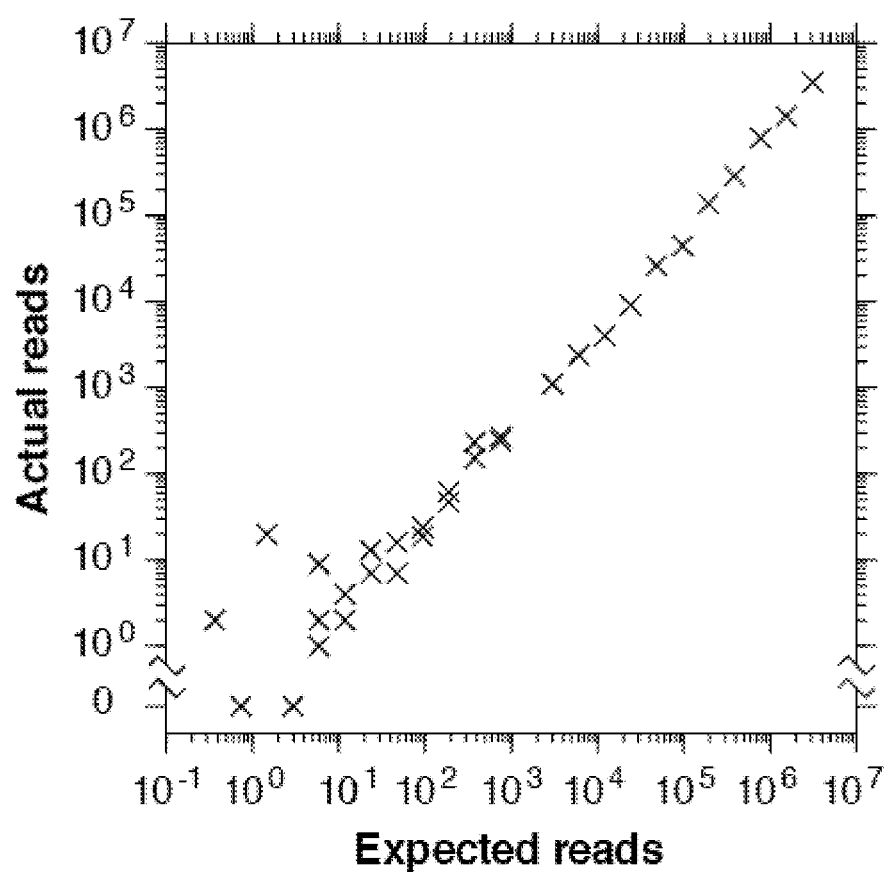
FIG. 7. Quantifying sequences by deep sequencing. Deep sequencing reads from a serial dilution series of synthetic DNA templates. The number of deep sequencing reads corresponds well to the concentration of the DNA template within the limits of statistical counting error for low-abundance templates.

In order to quantify translation, we set out to isolate ribosome footprints whose sequence would indicate the position of an active ribosome on an mRNA molecule, convert these RNA footprints into a library of DNA molecules, and measure the abundance of different footprints in this library by deep sequencing. We began by showing that deep sequencing can quantify the abundance of different nucleotide sequences in a complex mixture. We prepared a sequencing sample with synthetic DNA oligonucleotides whose relative abundances spanned more than seven orders of magnitude. When we analyzed this mixture by deep sequencing, the relative frequency of sequencing reads corresponded well to the relative abundance of the template in the mixture (FIG. 7).

We next developed a protocol for converting small RNAs into a sequenceable DNA library. It was important to capture different RNA sequences with similar efficiency, as sequence preferences would distort the observed frequency of different sequences. We also wished to retain strand information from the single-stranded RNA sample. In order to assess how uniformly we captured different sequences, we wanted a sample with many small RNAs of known relative abundance. To this end, we randomly fragmented budding yeast mRNA by high temperature alkaline hydrolysis, reasoning that the abundance of different fragments of the same mRNA should be equal. Additionally, quantifying these mRNA fragments would allow us to measure mRNA abundance. Deep sequencing reads and ribosome footprint fragments are roughly 30 nt long, so we prepared mRNA fragments of the same size. These fragments are too short for random priming of cDNA synthesis. Many protocols for capturing small RNAs such as microRNAs use single-stranded RNA ligases to attach linker oligonucleotides to the 3' terminus of target RNA molecules. However, these enzymes have strong sequence specificities that distort the abundance of ligation products relative to the input RNA pool. We instead added a homopolymer sequence to the 3' terminus using E. coli poly-(A) polymerase and used it as a primer site for first-strand cDNA synthesis. The second linker needed for PCR and sequencing was attached by circularizing the single-stranded DNA (FIG. 1A).

Figure 1B:
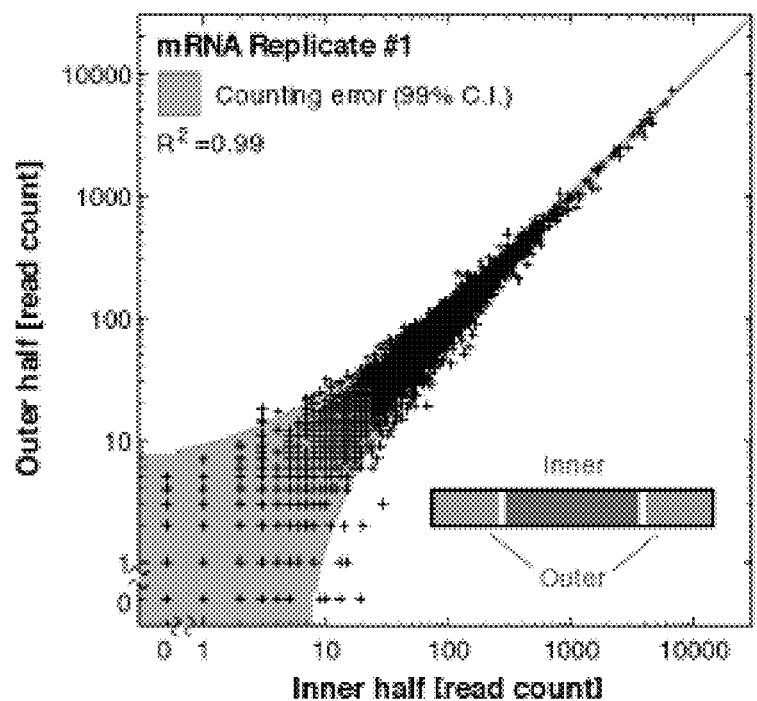
Figure 1C:
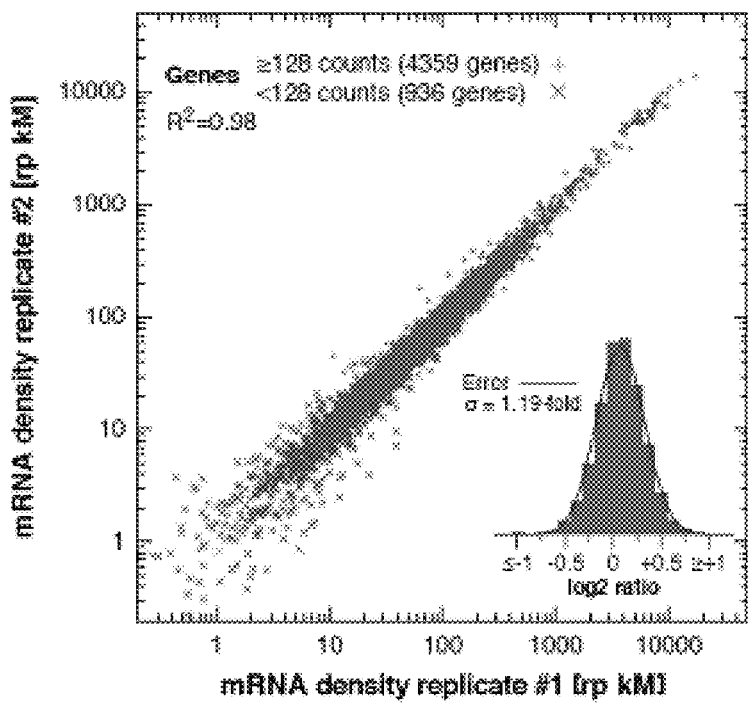
Figure 8A:
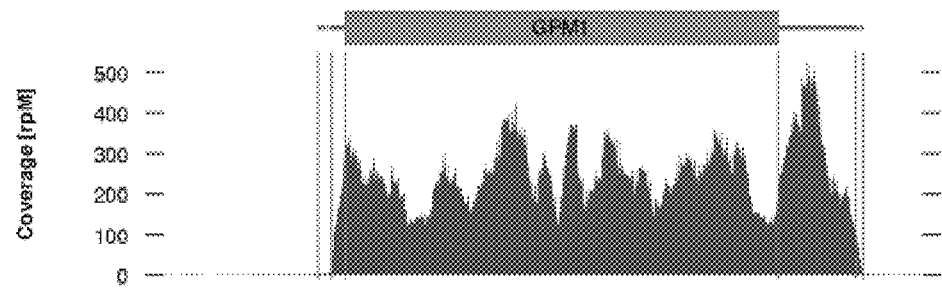
FIGS. 8A-E. Quantifying mRNA abundance by deep sequencing.
Figure 8B:
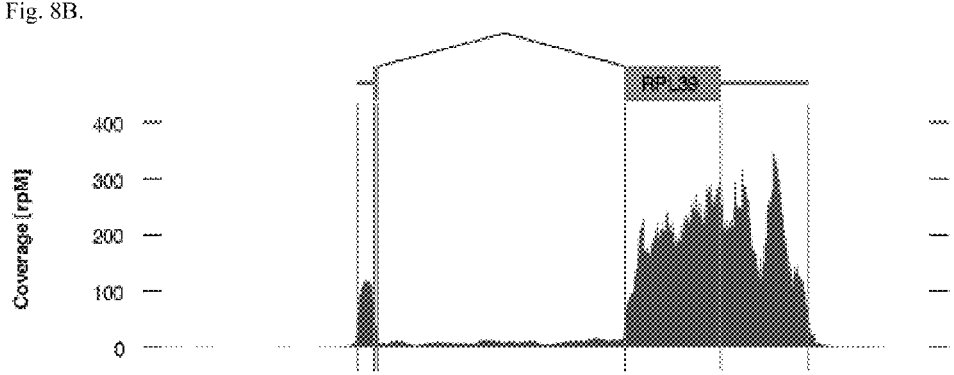
Figure 8C:
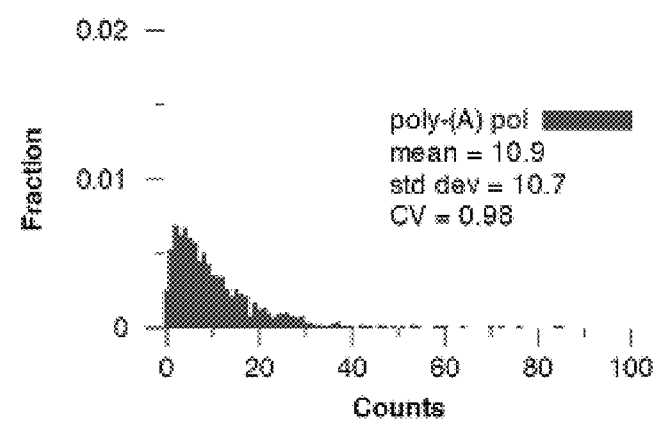
Figure 8D:
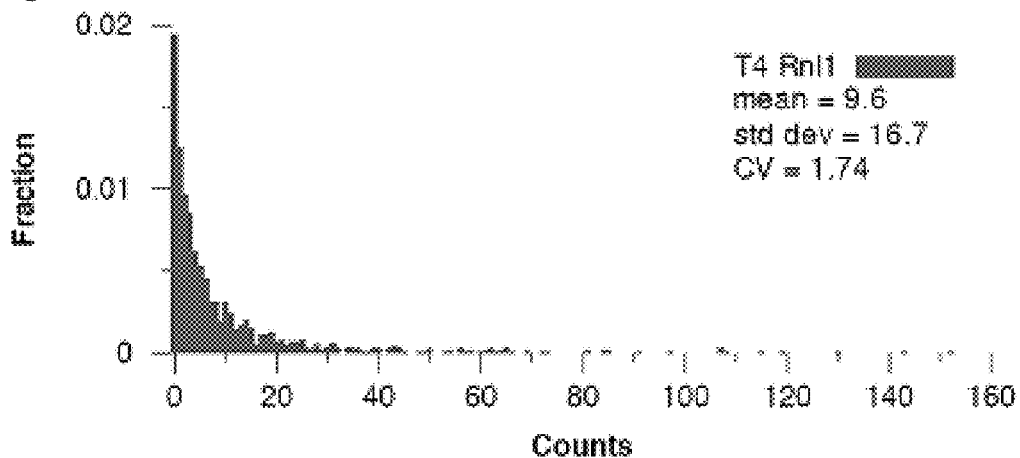
Figure 8E:
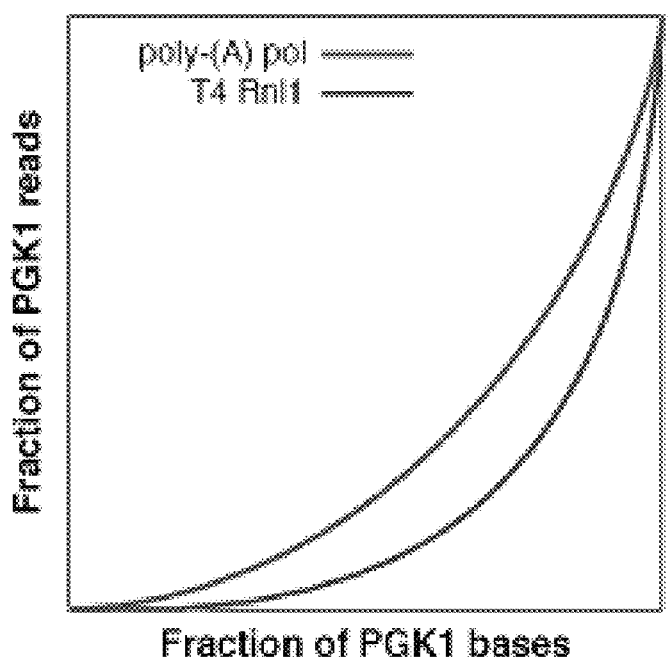
Figure 9A:
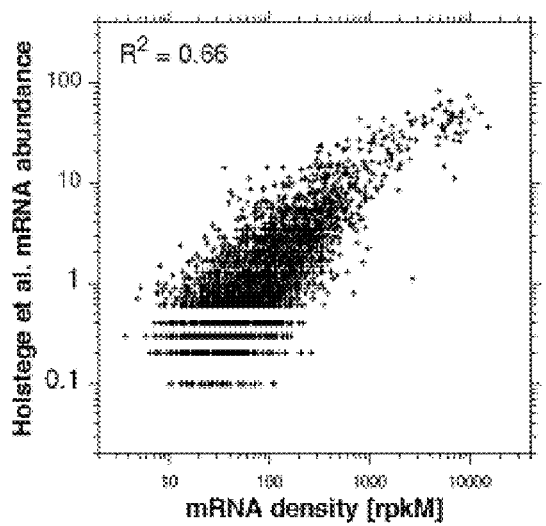
FIGS. 9A-C. Correlation between various genome-wide mRNA abundance measurements.
Figure 9B:
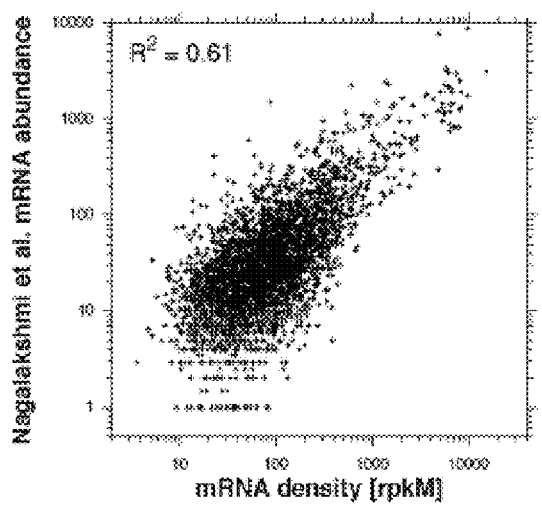
Figure 9C:
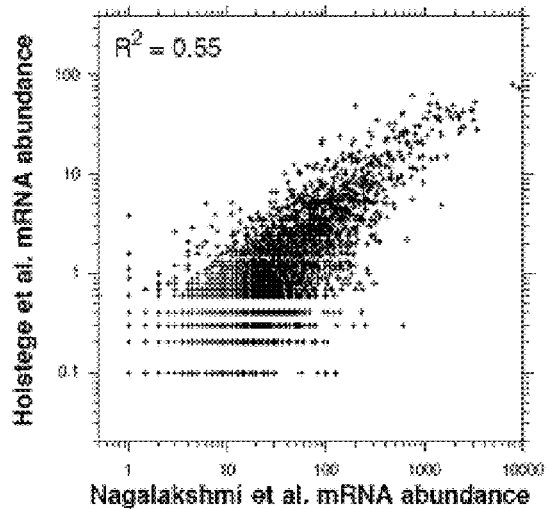

We performed deep sequencing on a library generated from small mRNA fragments reads, we found that 98.2% of the remaining sequences could be aligned to the yeast genome, and an additional 0.2% could be aligned to spliced mRNAs (Table 1 set forth below). Even in yeast, not all reads can be assigned uniquely to a single gene. We found that 420 of 5715 (7.3%) yeast protein-coding genes had a significant fraction (>20%) of reads that were non-unique, either because they aligned to multiple sites in the genome or because of overlapping transcribed features. We excluded these genes from further analysis. We used reads that aligned to the remaining 5285 genes to determine the technical reproducibility of RNA abundance measurements by deep sequencing. We conceptually divided each protein-coding sequence into two regions of equal length. The number of reads aligning to these two regions should represent independent measurements of the abundance of the full-length mRNA before fragmentation. We found that these two counts were in very good agreement ($R^2$=0.99, FIG. 1B). We also looked in detail at the coverage of sequencing reads across highly-expressed genes. We found that coverage varied less than 4-fold across the abundant GPM1 and RPL39 mRNAs, including the UTRs defined by cDNA sequencing, but was much lower in the intron of the spliced RPL39 gene (FIG. 8A, FIG. 8B). We also found a more homogeneous distribution of sequencing read starts across the PGK1 coding sequence in a sample prepared by poly-(A) tailing than in a sample prepared with the T4 Rnl1 single-strand RNA ligase (FIG. 8C to FIG. 8E). We next asked how well we could quantify mRNA abundance by deep sequencing of very short fragments. Because the number of small fragments derived from an mRNA is proportional to its length, we normalized read counts for each gene by the length of its coding sequence. We also normalized by the total number of CDS-aligned reads to arrive at an mRNA abundance measurement in reads per kilobase per million (rpkM), as described by Mortazavi et al. We quantified mRNA abundance in two fully independent biological replicates of yeast in log-phase growth in YEPD. The mRNA density measurements agreed very well between our biological replicates ($R^2=0.98$, FIG. 1C). The standard deviation in log ratio between biological replicates corresponds to a 1.19-fold change, suggesting that we can reliably detect small changes in mRNA abundance. This level of reproducibility compares favorably with microarray measurements. Our mRNA abundance measurements also agreed well with genome-wide measurements of mRNA abundance by microarray ($R^2=0.66$, FIG. 9A) and by deep sequencing of unfragmented RNA ($R^2=0.61$, FIG. 9B, FIG. 9C) (Holstege et al., "Dissecting the regulatory circuitry of a eukaryotic genome." *Cell* 95: 717 (1998); Wang et al., "Precision and functional specificity in mRNA decay." *Proc Natl Acad Sci USA* 99:5860 (2002); Nagalakshmi et al., "The transcriptional landscape of the yeast genome defined by RNA sequencing." *Science* 320: 1344 (2008)).

high RNase concentrations the protected fragments decreased in abundance rather than further decreasing in size. We then analyzed a ribosome footprinting sample by deep sequencing and found that 15.2% of the good reads aligned to yeast coding sequences, while 83.6% were derived from rRNA (see Table 1). As the mass of rRNA in each monosome is nearly 200 times the mass of the mRNA footprint, the presence of a six-fold excess of rRNA in the size-selected sample is unsurprising. Fortunately, a large fraction of this contaminating rRNA is derived from a few specific sites; in future experiments, it should be easily removable by subtractive hybridization prior to sequencing. It was not always possible to determine the exact length of footprint fragments—a terminal A may be derived either from the RNA fragment or from the homopolymer linker we added. When the exact length of the RNA fragment could be unambiguously determined, we found that ribosome footprints had a characteristic size—more than half were 28 or 29 nt long—while both copurified rRNA fragments, and random mRNA fragments subject to size selection in parallel, had a different

TABLE 1

| Alignment | mrna rich1 | % | mrna noaa1 | % | mrna rich2 | % | mrna noaa2 | % |
|---|---|---|---|---|---|---|---|---|
| Total | 4700324 | | 4135727 | | 13018070 | | 10659366 | |
| Culled | 2398225.1 | | 314000 | 7.6 | 133668 | 1.0 | 51956 | 0.5 |
| Unculled | 4460502 | 94.9 | 3821727 | 92.4 | 12884402 | 99.0 | 10607410 | 99.5 |
| Unculled | 4460502 | | 3821727 | | 12884402 | | 10607410 | |
| rRNA | 1925728 | 43.2 | 2172947 | 56.9 | 4978873 | 38.6 | 5387823 | 50.8 |
| No rRNA | 2534774 | 56.8 | 1648780 | 43.1 | 7905529 | 61.4 | 5219587 | 49.2 |
| Genomic | 2454964 | 55.0 | 1572289 | 41.1 | 5721013 | 44.4 | 3502836 | 33.0 |
| No rRNA | 2534774 | | 1648780 | | 7905529 | | 5219587 | |
| Genomic | 2454964 | 96.9 | 1572289 | 95.4 | 5721013 | 72.4 | 3502836 | 67.1 |
| No genomic | 79810 | 3.1 | 76491 | 4.6 | 2184516 | 27.6 | 1716751 | 32.9 |
| CDSes + 100 bp | 2266754 | 89.4 | 1462372 | 88.7 | 5210137 | 65.9 | 3229889 | 61.9 |
| Splices | 7259 | 0.3 | 3188 | 0.2 | 23631 | 0.3 | 7758 | 0.1 |
| Genomic | 2454964 | | 1572289 | | 5721013 | | 3502836 | |
| CDSes + 100 bp | 2266754 | 92.3 | 1462372 | 93.0 | 5210137 | 91.1 | 3229889 | 92.2 |
| Splices | 7259 | 0.3 | 3188 | 0.2 | 23631 | 0.4 | 7758 | 0.2 |

| Alignment | fp rich1 | | fp noaa1 | | fp rich2 | | fp noaa2 | |
|---|---|---|---|---|---|---|---|---|
| Total | 13561039 | | 9073940 | | 28616240 | | 18841676 | |
| Culled | 467489 | 3.4 | 467281 | 5.1 | 256924 | 0.9 | 70898 | 0.4 |
| Unculled | 13093550 | 96.6 | 8606659 | 94.9 | 28359178 | 99.1 | 18770778 | 99.6 |
| Unculled | 13093550 | | 8606659 | | 28359178 | | 18770778 | |
| rRNA | 10952914 | 83.7 | 7531522 | 87.5 | 17828899 | 62.9 | 14023989 | 74.7 |
| No rRNA | 2140636 | 16.3 | 1075137 | 12.5 | 10530279 | 37.1 | 4746789 | 25.3 |
| Genomic | 2000107 | 15.3 | 986611 | 11.5 | 5138796 | 18.1 | 2671653 | 14.2 |
| No rRNA | 2140636 | | 1075137 | | 10530279 | | 4746789 | |
| Genomic | 2000107 | 93.4 | 986611 | 91.8 | 5138796 | 48.8 | 2671653 | 56.3 |
| No genomic | 140529 | 6.6 | 88526 | 8.2 | 5391483 | 51.2 | 2075136 | 43.7 |
| CDSes + 100 bp | 1926044 | 90.0 | 930091 | 86.5 | 5031093 | 47.8 | 2568616 | 54.1 |
| Splices | 19047 | 0.9 | 5516 | 0.5 | 52025 | 0.5 | 14493 | 0.3 |
| Genomic | 2000107 | | 986611 | | 5138796 | | 2671653 | |
| CDSes + 100 bp | 1926044 | 96.3 | 930091 | 94.3 | 5031093 | 97.9 | 2568616 | 96.1 |
| Splices | 19047 | 1.0 | 5516 | 0.6 | 52025 | 1.0 | 14493 | 0.5 |

Figure 10A:
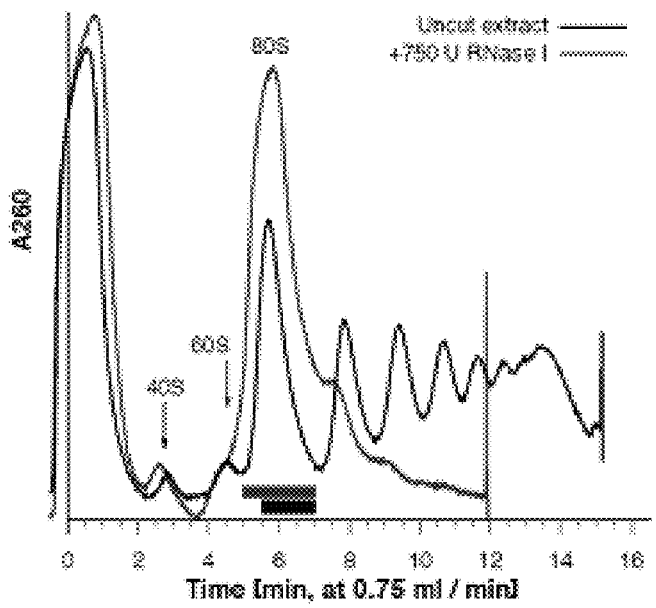
FIGS. 10A-C. Footprinting translating ribosomes on mRNA.
Figure 10B:
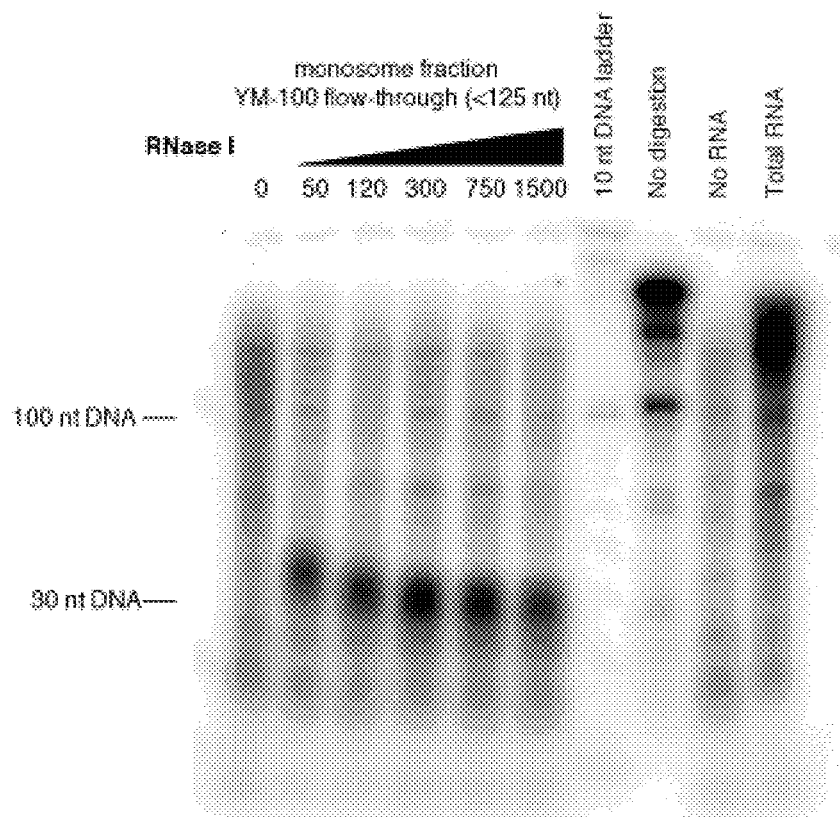
Figure 10C:
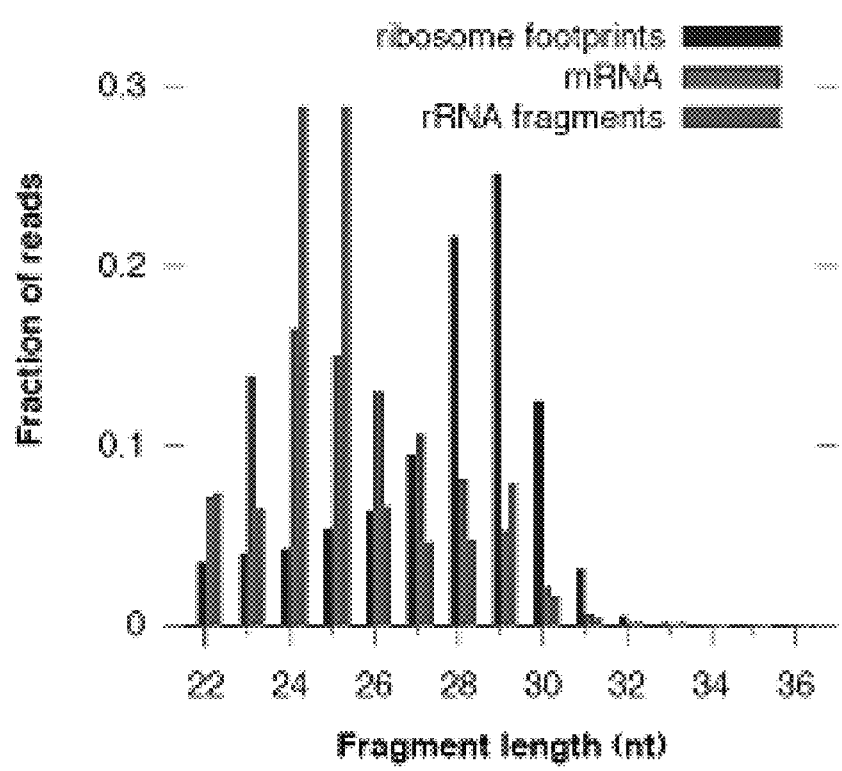

Finally, we set out to establish nuclease footprinting of translating ribosomes on mRNA. We treated cells with the translation elongation inhibitor cycloheximide to immobilize ribosomes and prepared cell extracts containing polysomes. We then treated extracts with *E. coli* RNase I, a non-specific endoribonuclease, to digest the mRNA. Digestion of polysomes with RNase released individual 80S ribosomes (FIG. 10A). We tested these monosomes for residual protected mRNA footprints with a nuclease protection assay for the abundant TDH2/TDH3 mRNA and found digestion-dependent fragments roughly 30 nt long (FIG. 10B). At low RNase concentrations the mRNA fragments were somewhat longer, presumably because the mRNA was not fully digested, but at length distribution (see FIG. 10C). The 28-29 nt sequence length agrees well with the size of the TDH2 mRNA fragments we observed.

Figure 2A:
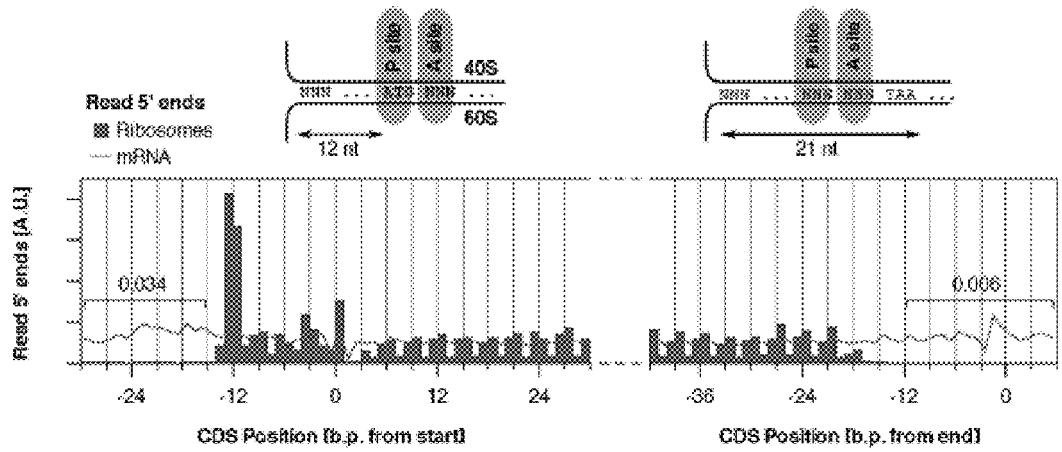
FIGS. 2A-B. Ribosome footprints provide a codon-specific measurement of translation.

Ribosome footprinting reveals the position of the ribosome with single-nucleotide precision. We counted ribosome footprints starting at positions around the 5' end of coding sequences and found that footprints started abruptly 13 bp upstream of the start codon (FIG. 2A). There were a particularly large number of ribosome footprint counts just at the −13 and −12 positions, followed by a more uniform density through the coding sequence showing a clear periodicity corresponding to the triplet genetic code (FIG. 2A). We calibrated the position of the ribosome relative to the position of the footprint using the fact that the initiator codon occupies the P site of the initiating ribosome to conclude that footprints generally start 12 or 13 nucleotides upstream of the first nucleotide of the P site (FIG. 2A). Footprints then extend 16 to 17 nucleotides downstream of the P site codon. The 3' end of the ribosome is known to block primer extension and create a toeprint 16 to 18 nucleotides downstream of the P site as well. Around the stop codon, we see normal footprint density 21 nucleotides upstream of the end of the coding sequence, when the last sense codon occupies the A site. There is reduced density when the stop codon occupies the A site 18 nucleotides before the end of the gene, and very few footprints beyond that point. Ribosomal footprint density aligns very well with the boundaries of translated sequences.

Figure 2B:
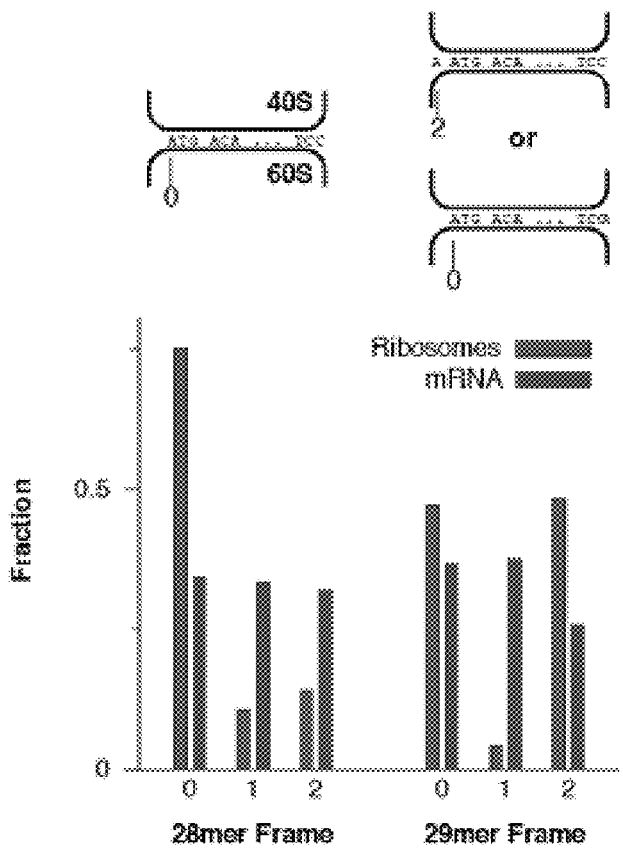

The triplet periodicity in the location of ribosome footprints led us to further investigate how footprints correspond to reading frame. The variability in footprint length indicates some combination of variation at the 5' or 3' end of the footprint, which could blur the underlying periodicity of the genetic code. We looked specifically at footprints whose length could be unambiguously determined and found that the 28mers had the strongest bias for a specific reading frame, with 75% starting on the first nucleotide of a codon (FIG. 2B). The unambiguous 29mer reads were extended with roughly equal probability either from the 3' end, leaving the 5' end unchanged, or from the 5' end, in which case they started on the third nucleotide of the preceding codon. Combined with our earlier observations, this shows that 28mer ribosome footprints start 12 nucleotides upstream of the P site codon, while 29mer ribosome footprints start either 12 or 13 nucleotides upstream. Ribosome footprinting is clearly reporting on the process of translation, and provides sub-codon precision that shows the boundaries of the coding sequence and the reading frame being translated.

Genome-wide Measurements of Translation

Figure 3A:
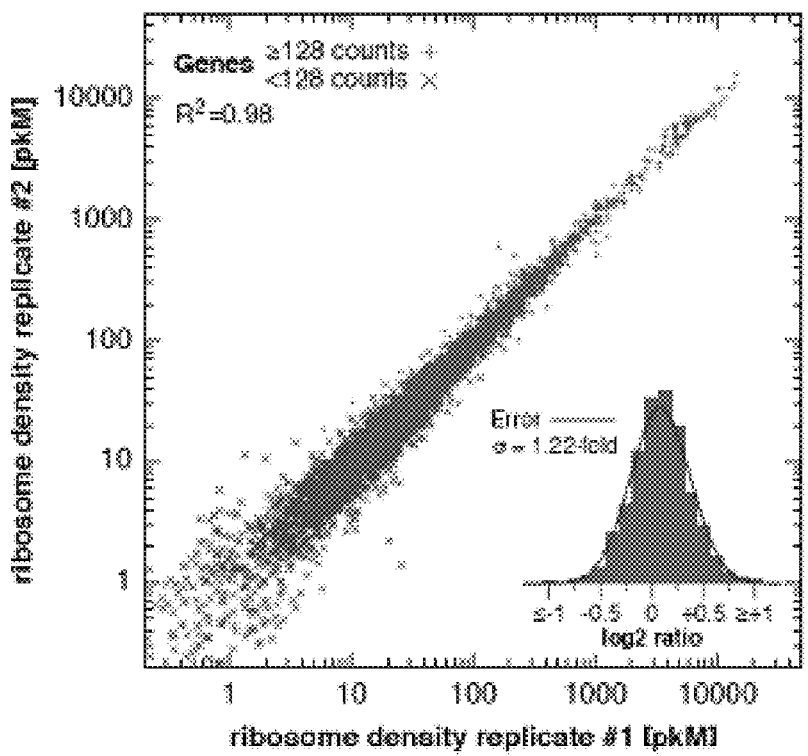
FIGS. 3A-D. Quantifying translation by ribosome footprinting.
Figure 11A:
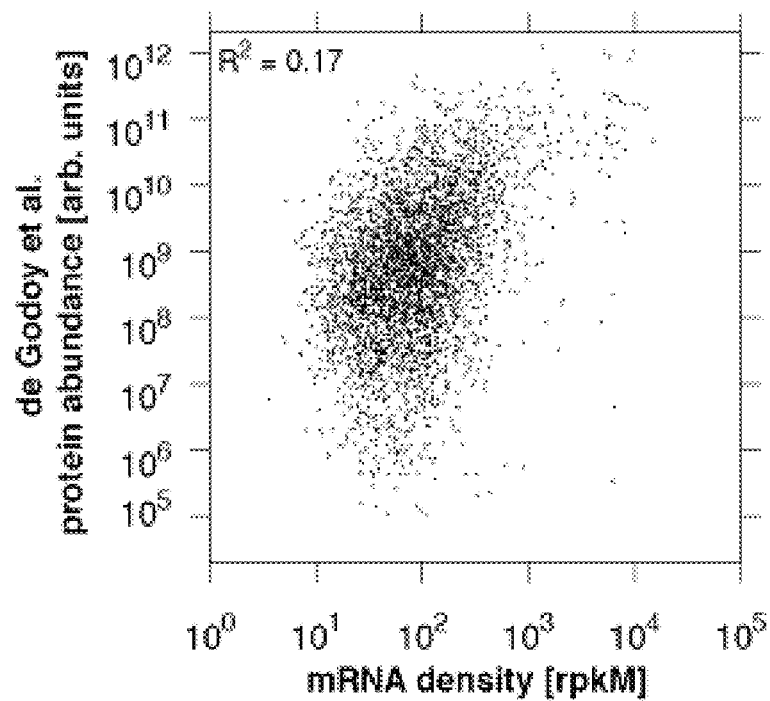
FIGS. 11A-D. Correlation between protein abundance and gene expression measurements.
Figure 11B:
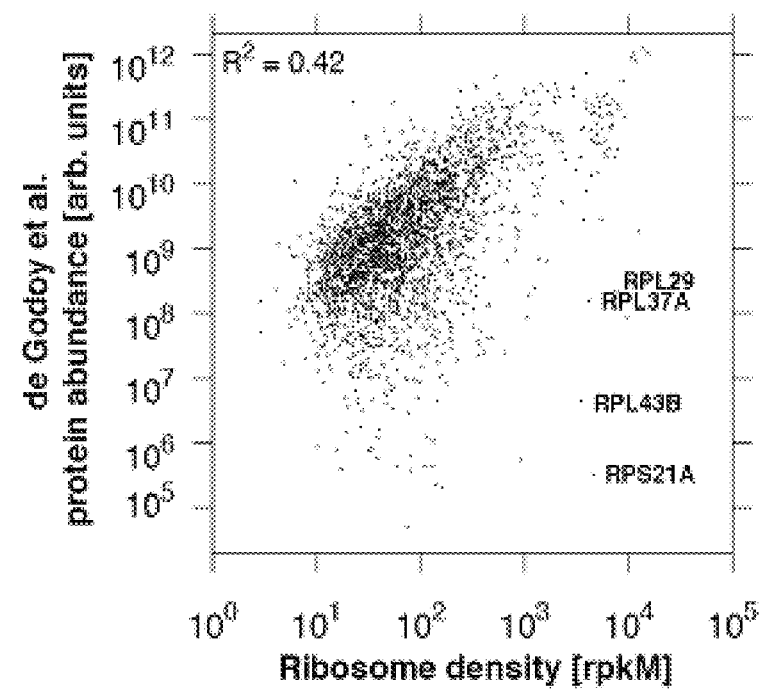
Figure 11C:
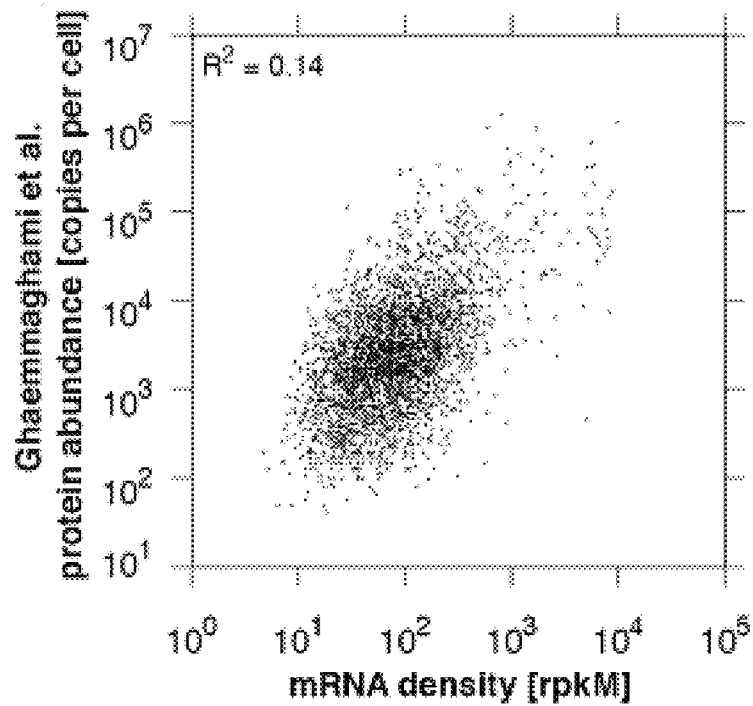
Figure 11D:
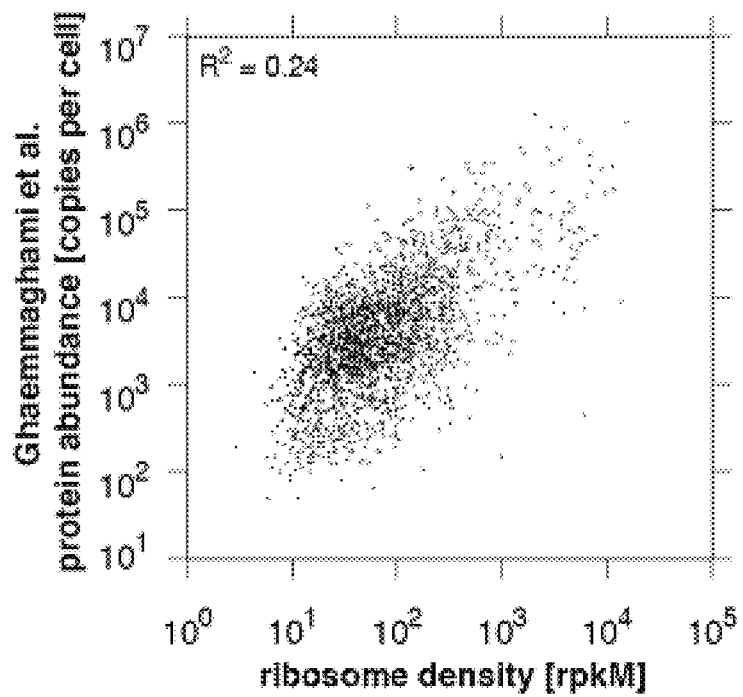

Protein synthesis rate should be a better measure of the expression of protein-coding genes than mRNA abundance, as it is more proximal to the production of functional protein. Ribosome footprint density provides a genome-wide measurement of protein synthesis, assuming that ribosomes translate proteins at a roughly constant rate. We found that ribosome footprint density is almost as reproducible between full biological replicates as mRNA fragment density ($R^2=0.98$, FIG. 3A). The inter-replicate error was again small, corresponding to a 1.22-fold change, indicating that we could confidently quantify even small translational changes. Furthermore, we found that genome-wide measurements of protein abundance correlate better with ribosome footprint density than with mRNA fragment density ($R^2=0.25$ vs. $R^2=0.14$, FIG. 11A, FIG. 11B), suggesting that our approach could provide a better measure of gene expression than traditional approaches based on mRNA abundance.

Figure 3B:
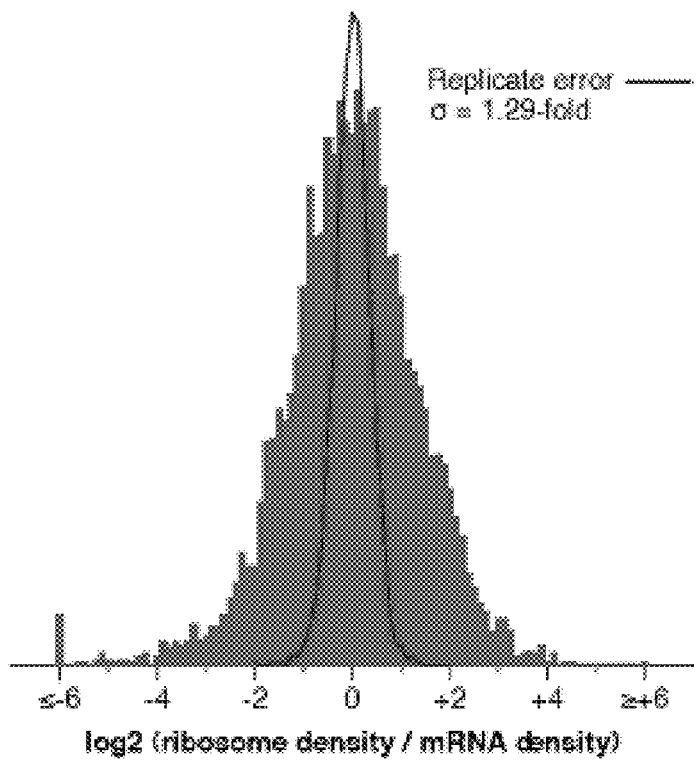
Figure 12A:
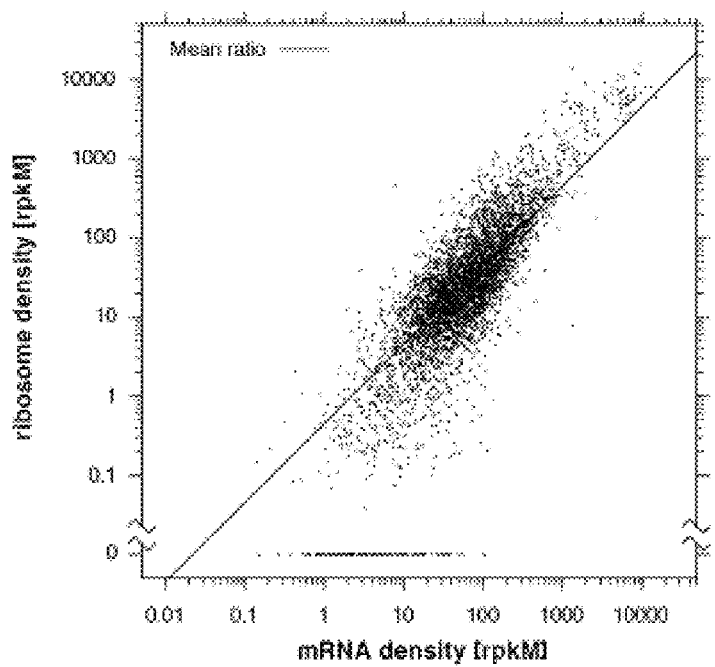
FIGS. 12A-B. Ribosome density as a measure of protein synthesis.

As protein synthesis does not correspond perfectly with mRNA abundance, there must be differences in the translational efficiencies of different mRNA species. We used measurements of mRNA fragment and ribosome footprint density to estimate these differences in translation (FIG. 3B, FIG. 12A). Some mRNAs are translated over 10-fold more highly than the median gene, while others are translationally inactive although they are present at moderate abundance. Translational effects that are invisible to mRNA abundance measurements contribute substantially to the dynamic range of gene expression. We noted that genes with high mRNA abundance often had a particularly high translational efficiency as well (FIG. 12A). Highly translated genes were enriched for functional categories such as glycolysis and other metabolic processes and cell wall components as well as for cytosolic proteins. These genes are probably under selection for high rates of protein production. Very poorly translated mRNAs showed fewer functional trends, though there was a significant enrichment of sporulation-related genes in the most poorly translated subset, which is consistent with the absence of sporulation under these growth conditions.

Figure 3C:
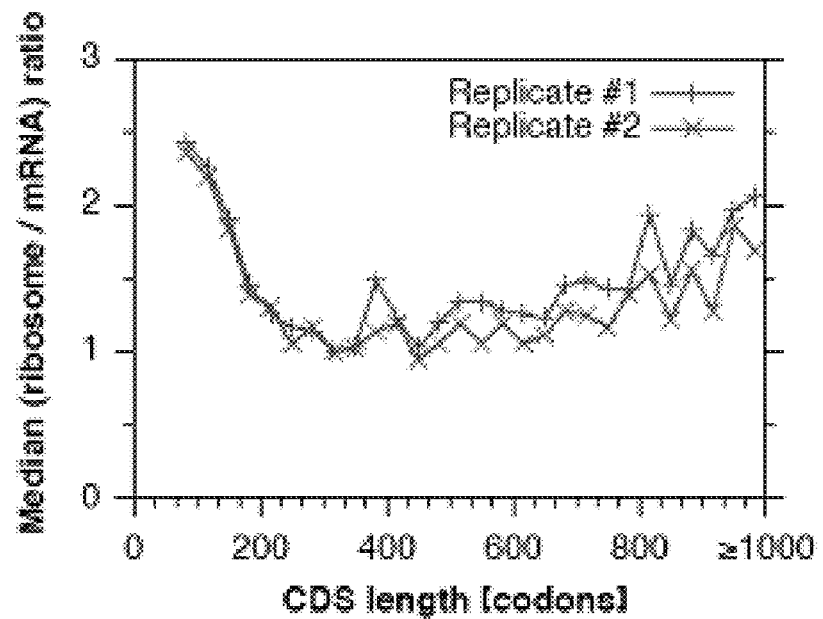
Figure 12B:
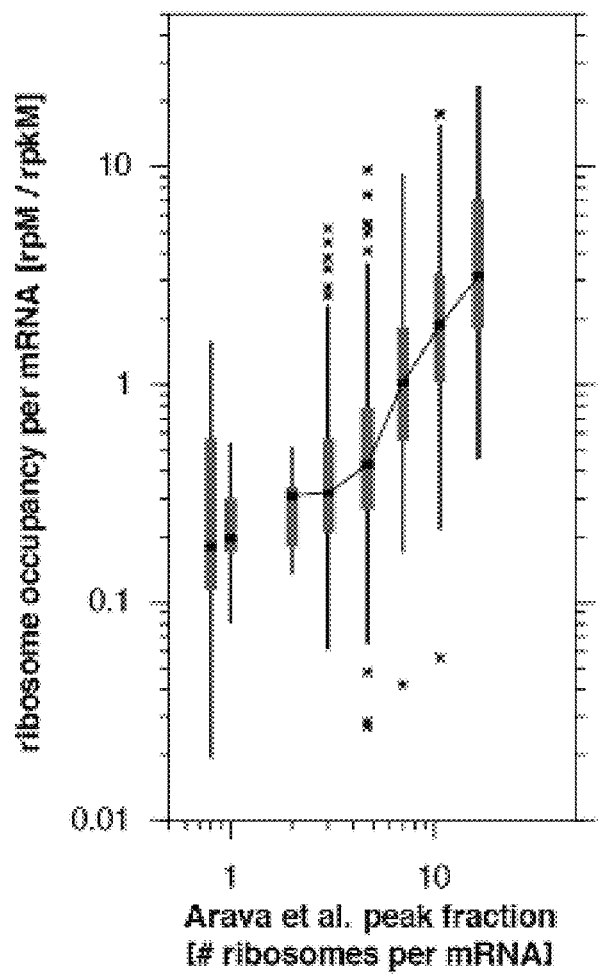

We compared our translation measurements to a previous genome-wide study of translation in yeast. Arava et al. measured the ribosome occupancy of mRNAs by analyzing different fractions of a polysome profile on microarrays. There was a clear trend of higher ribosome occupancy in our data set for mRNAs that had previously been found in larger polysomes (FIG. 12B). One notable observation from the earlier genome-wide study was an inverse relationship between CDS length and ribosome density. We see a similar, though weaker, tendency for short genes to have higher ribosome density per mRNA density (FIG. 3C). Arava et al. proposed several explanations for this trend, including a higher ribosome density in a region of constant length at the start of each gene, which would contribute a larger fraction of the total ribosome occupancy for a shorter gene. However, a subsequent study found no evidence for higher ribosome density at the 5' end of six individual mRNAs.

Figure 3D:
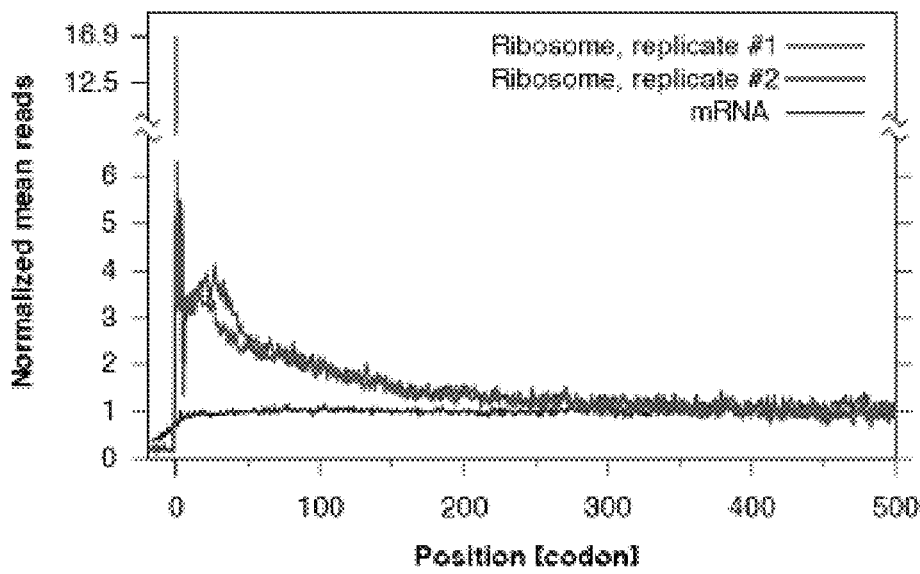
Figure 13A:
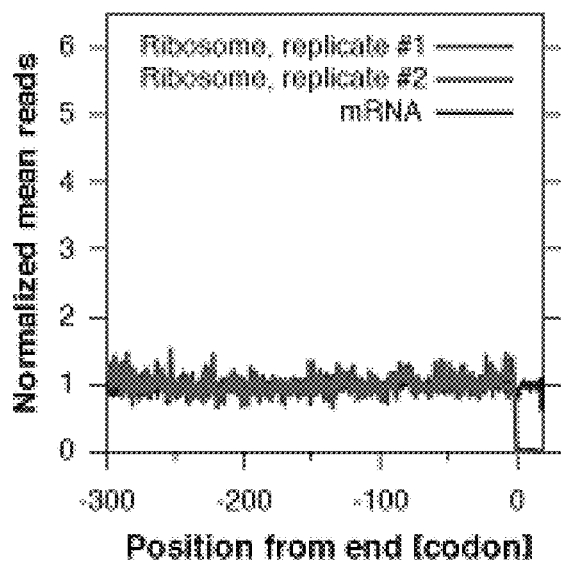
FIGS. 13A-D. Read density as a function of position for subsets of genes.
Figure 13B:
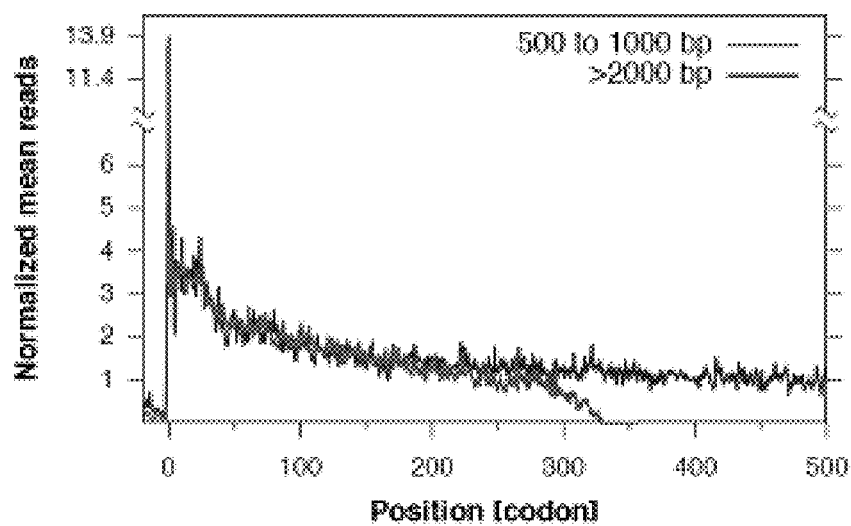
Figure 13C:
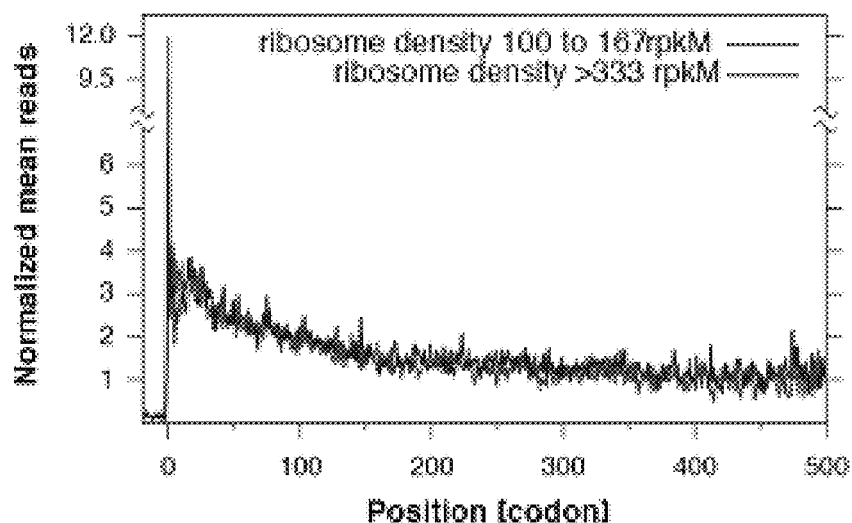
Figure 13D:
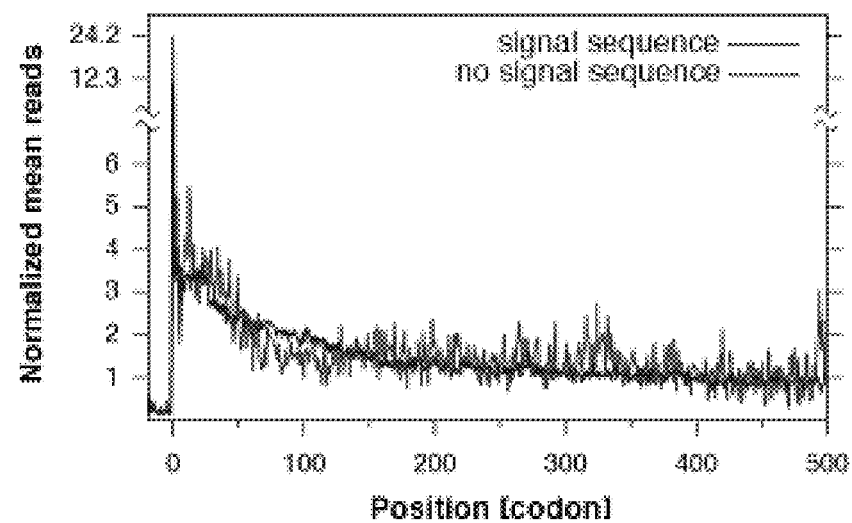

We revisited this model by averaging ribosome footprint counts at each position over well-translated yeast genes and found higher ribosome density at the 5' end of coding sequences (FIG. 3D). Ribosome density is uniform at the 3' end of the gene (FIG. 13A), and the higher 5' density is independent of the length of the coding sequence, of its expression level, and of the presence of an N-terminal signal sequence (FIG. 13B to FIG. 13D). Changes in ribosome density could reflect either changes in the rate of translation or premature termination of translation. The increase in ribosome density over codons 5-30 cannot be explained by premature termination, which can only cause a decrease ribosome density with increasing distance from the start of the coding sequence. However, both factors may play a role in the overall decline in ribosome density. The pattern of footprint density suggests that there are three phases of translation: an initiation phase spanning the first few codons, an early elongation phase which may extend 30-40 codons, and a late elongation phase. These phases may correspond to different functional states of the ribosome that affect its rate of elongation or processivity, much as RNA polymerase II shows different patterns of C-terminal domain phosphorylation at different stages of transcriptional elongation. It is not clear how the ribosome might differentiate between these states, but the end of the early elongation phase does correspond to the emergence of the nascent peptide from the ribosome. Interactions of the nascent peptide with the exit channel of the ribosome or with ribosome-associated protein chaperones might affect the rate of translational elongation. Furthermore, the length scale over which ribosome density approaches its long-term steady state level corresponds to the length of the shortest yeast protein-coding genes—more than 95% are over 100 codons. The altered ribosome density before 100 codons might relate to a mechanistic difference between translation of protein coding genes, where the ribosome reaches this steady-state phase of elongation, and translation of short upstream open reading frames, where it does not.

Codon-Specific Measurements of Translation

Figure 4A:
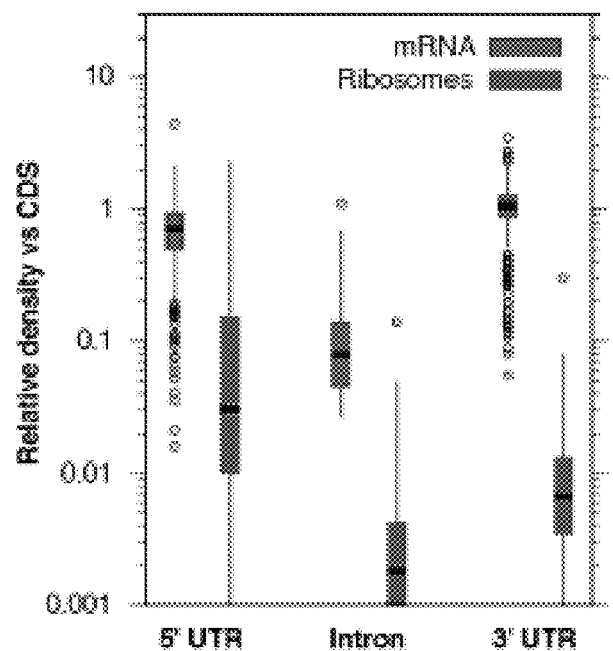
FIGS. 4A-G. Ribosome occupancy of upstream open reading frames and other sequences.
Figure 4B:
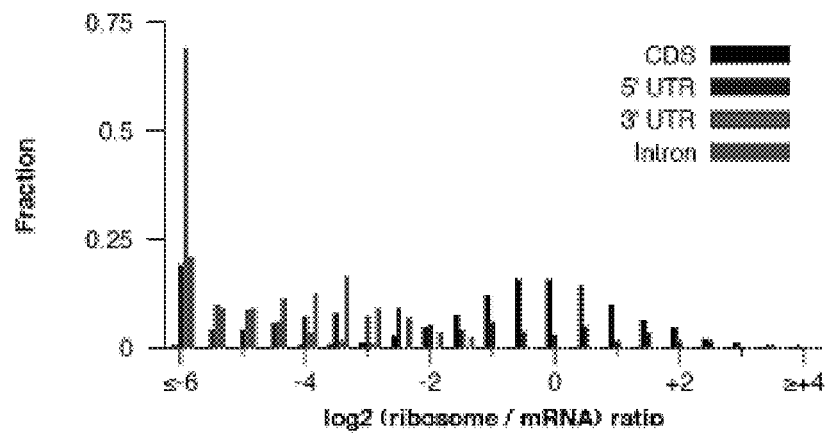
Figure 4C:
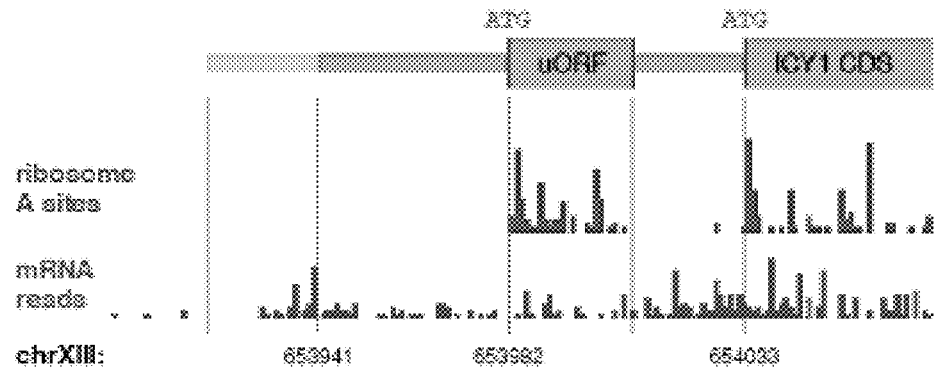
Figure 4D:
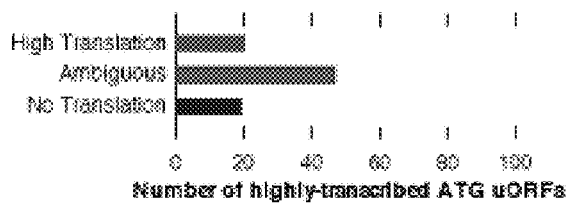

We quantified the relative density of mRNA fragments and ribosome footprints outside of protein-coding sequences. The mRNA density in annotated 5' and 3' UTRs are generally similar to the adjacent coding sequence (FIG. 4A), and outliers probably represent variability in transcription or annotation errors. Intron mRNA density is lower than the mRNA density in the surrounding exonic coding sequence, and the intronic mRNA sequences we observe probably represent splicing intermediates as well as mature but unspliced transcripts. The one high-confidence outlier is the non-spliceosomal intron of HAC1, which is retained under these growth conditions. However, ribosome footprint density is dramatically lower than mRNA density on all of these nominally untranslated sequences. Introns and 3' UTRs typically have less than 1% of the ribosome density of the associated gene, and are typically too poorly translated to reliably quantify. While 5' UTRs also have lower ribosome occupancy than coding sequences, the disparity is smaller and varies more between genes. We also directly quantified translation as the ratio of ribosome footprints to mRNA fragments for introns and UTRs (FIG. 4B). The same pattern appears here, with introns and 3' UTRs having overall very low ribosome occupancy, while 5' UTRs show a very wide distribution of relative ribosome density. One possible explanation is the presence of ribosomes on upstream open reading frames (uORFs) in 5' UTRs. We verified that some predicted uORFs, such as one in the ICY1 5' UTR, were translated (FIG. 4C). Others were not, although the mRNA density measurements confirmed the presence of a well-transcribed 5' UTR with an upstream ATG (FIG. 4D).

Figure 4E:
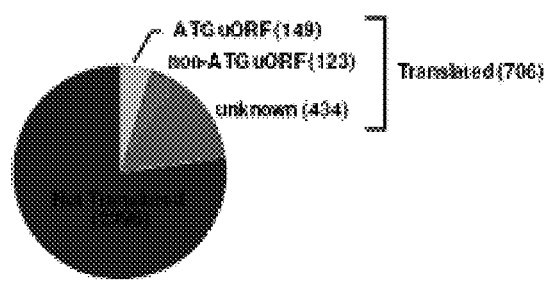
Figure 4F:
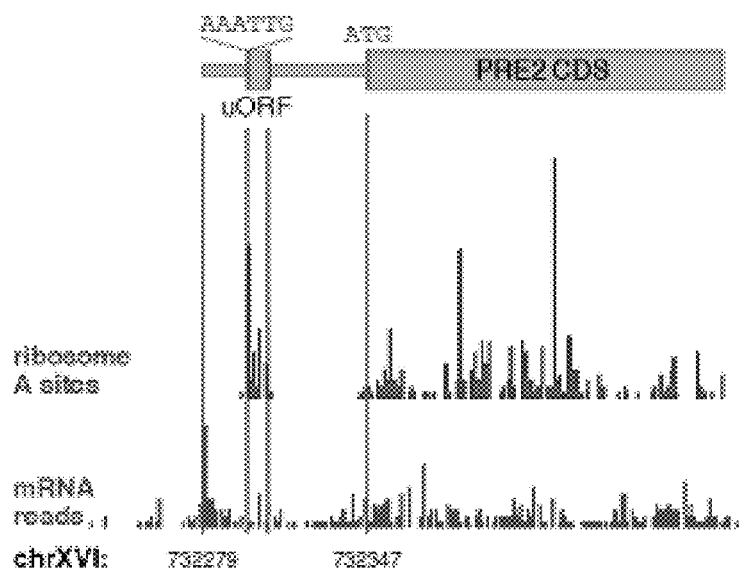
Figure 4G:
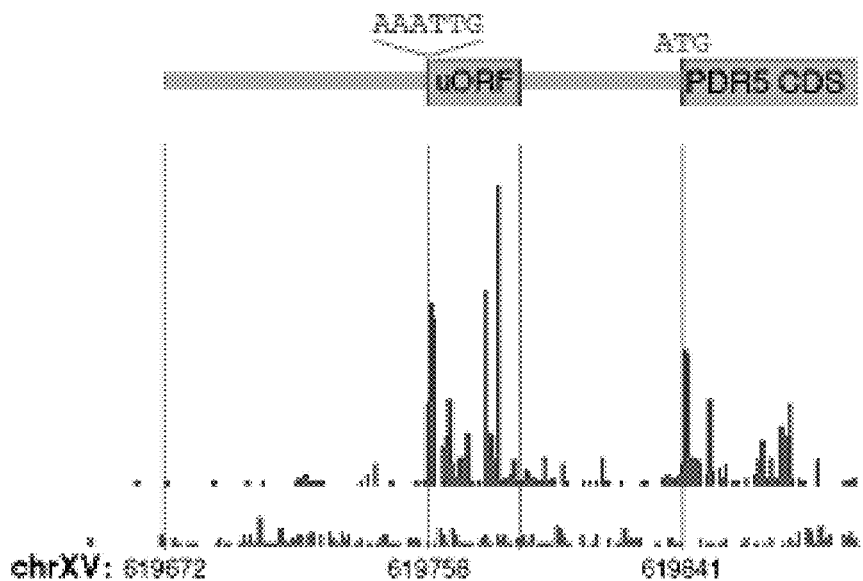

The presence of uORFs accounted for only a fraction of the total ribosome density on 5' UTRs (FIG. 4E). Some genes, such as PRE2, showed a discrete region of ribosome density terminated by a stop codon (FIG. 4F). Other genes, such as PDR5, had enough 5' UTR ribosome footprints that we could determine the reading frame as well (FIG. 4G). We confirmed that the actual 5' UTR sequences captured in our experiment had no ATG and found that in both of these cases the apparent start site was associated with a TTG. There are a handful of known examples in yeast where translation initiates at a TTG codon. Initiation at a TTG is strongly dependent on a favorable upstream sequence context, and both PRE2 and PDR5 have a favorable AAA sequence immediately upstream of the predicted initiation site.

Based on these examples, we predicted additional non-ATG uORFs by finding candidate initiation codons with a favorable initiation context and just 1 mismatch against ATG. In aggregate, predicted uORFs where the start codon had a mismatch at positions 1 or 3 had a much higher ratio of ribosome footprints to mRNA than other 5' UTR sequence, although it was not as high as true ATG uORFs. The bias in ribosome occupancy lends support to the idea that initiation at favorable non-ATG sites could account for the 5' UTR ribosome occupancy even if this particular set of uORFs does not fully account for the phenomenon (FIG. 4E). It is not always possible to predict which canonical ATG codons will lead to uORF translation (FIG. 4D), and initiation at non-ATG codons adds another layer of complexity. Genome-wide ribosome footprinting should provide the data needed to build new, quantitative models of start site selection and understand its impact on protein production.

Figure 14:
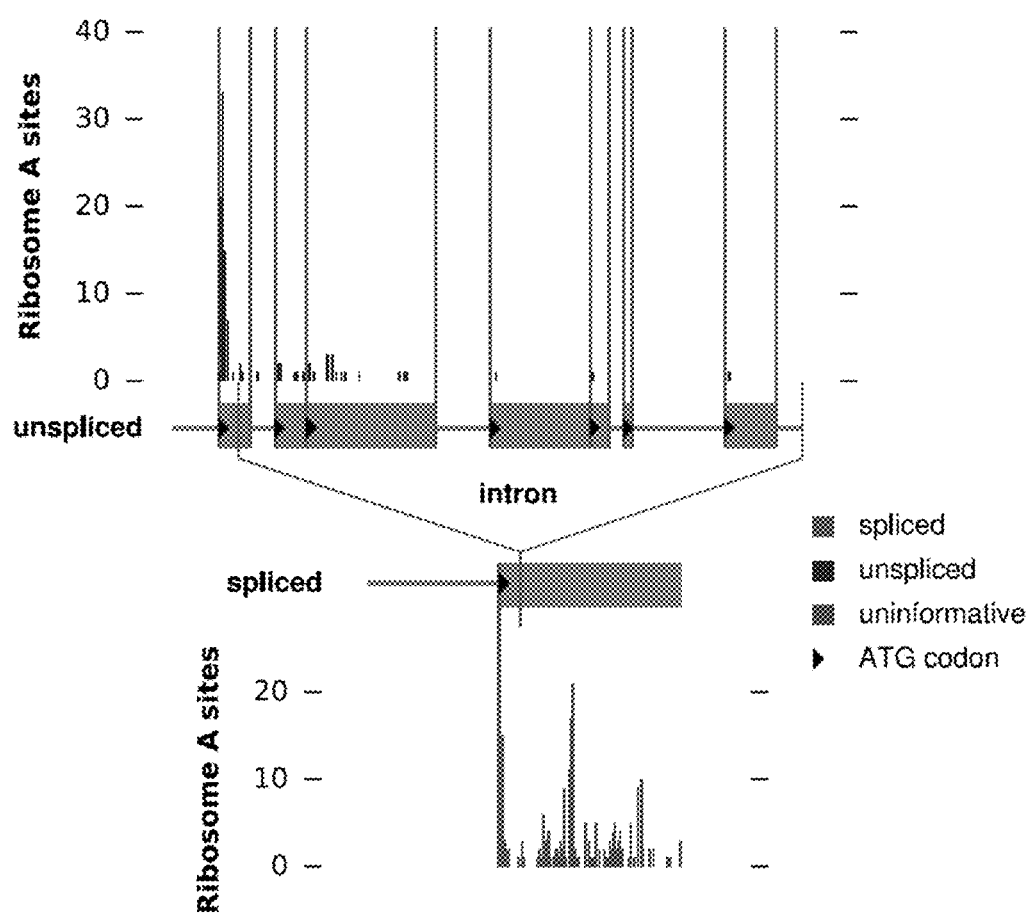
FIG. 14. Reads aligning to spliced and unspliced RPL22B. Translation of the intron can be explained by reinitiation or leaky scanning following the normal ATG, which starts a 7 codon ORF in the unspliced form. Almost all intronic ribosome footprints are derived from the next downstream ORF in the intron, with three remaining reads distributed exactly at the sites of three other ATG codons. Only reads that were at least 27 nucleotides long, with no more than one mismatch, were used. These restrictions allow us to assign reads beginning on the start codon to either the spliced or the unspliced form because the 5' splice site is only 12 nucleotides downstream of the beginning of the gene. The downstream ATGs in the intron sequence are indicated, along with the next in-frame stop. Whenever a second ATG occurs in an open reading frame, it is in-frame, so there are no overlapping reading frames.
Figure 15:
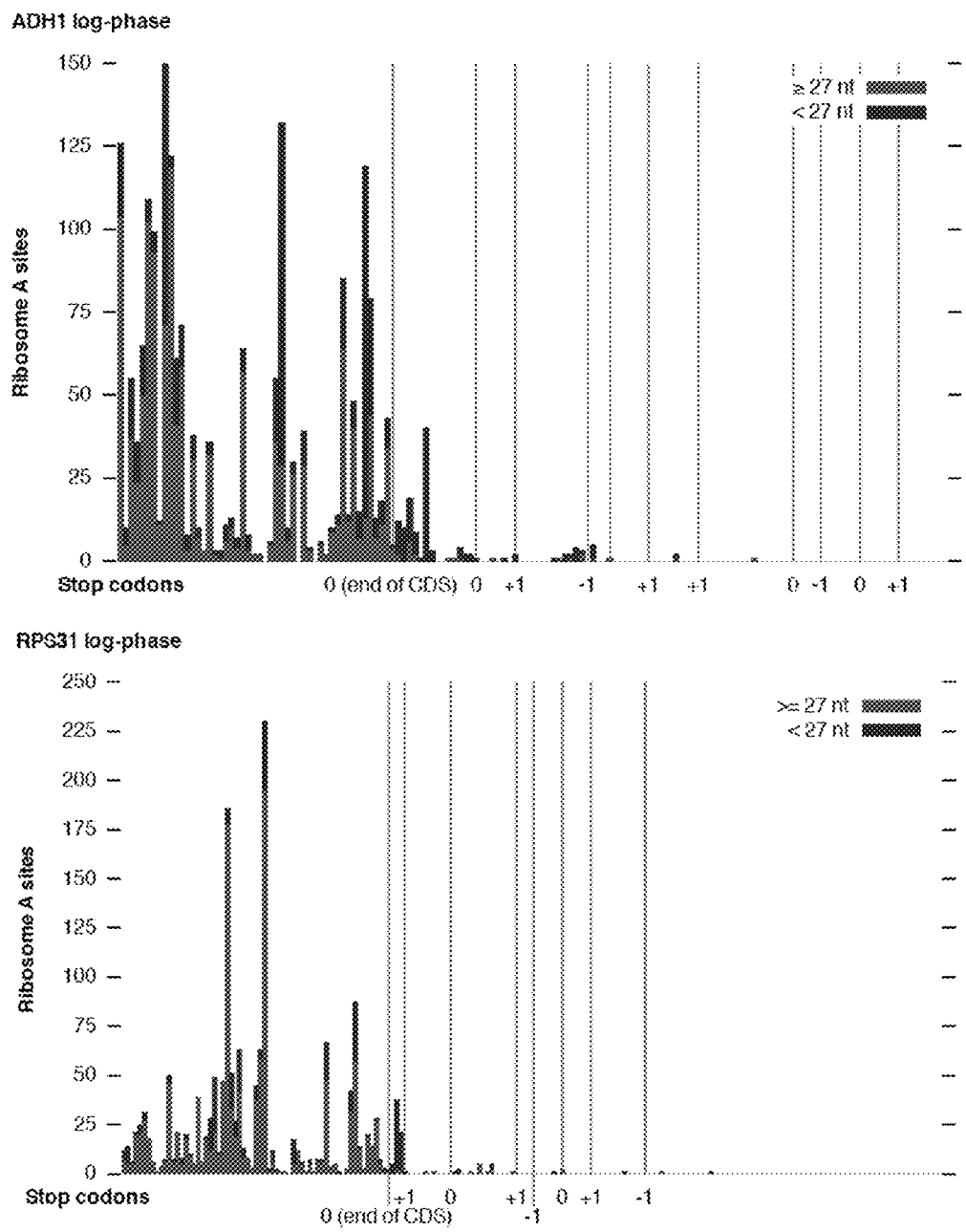
FIG. 15. Translational termination and ribosomes at the 3' end of highly-expressed genes. (A) Ribosome footprints aligned to the end of the highly-expressed ADH1 gene. All stop codons in the region are shown, along with their reading frame. Most of the reads the predicted A site of which lies just after the stop codon are shorter than 27 nt. These footprints might represent 5' truncations that would have been assigned to the coding sequence were they full-length, as we determined the A site from the 5' end of the read. Alternately, they may indicate an altered ribosome footprint at the stop codon. The footprints after the CDS stop are not bounded by the next stop codon in any particular reading frame. (B) Ribosome footprints aligned to the end of the highly-expressed RPS31 gene.

We also investigated the small number of ribosome footprints derived from other nominally untranslated sequences. We saw very low levels of intronic translation in general, but we were able to investigate the highly-expressed RPL22B gene due to its high level of intron retention (FIG. 14). In the unspliced RPL22B transcript, the canonical start codon begins a short, highly translated ORF. We also see evidence of translation from downstream ATG codons in the intron, resulting either from reinitiation after translation of the first short ORF or from leaky scanning past the canonical start codon. This pattern of translation is consistent with our understanding of initiation and the effects of uORFs. We also saw very little translation downstream of stop codons even in highly-expressed genes. In two cases we investigated, ADH1 and RPS31, the infrequent downstream ribosome footprints could not be easily explained by continued translation either in the original reading frame or in an altered reading frame, based on the location of further downstream stop codons (FIG. 15). Translation of these regions represents a very small fraction of total translation, however, and may mostly reflect noise in initiation and termination.

Translational Responses to Starvation

Figure 5A:
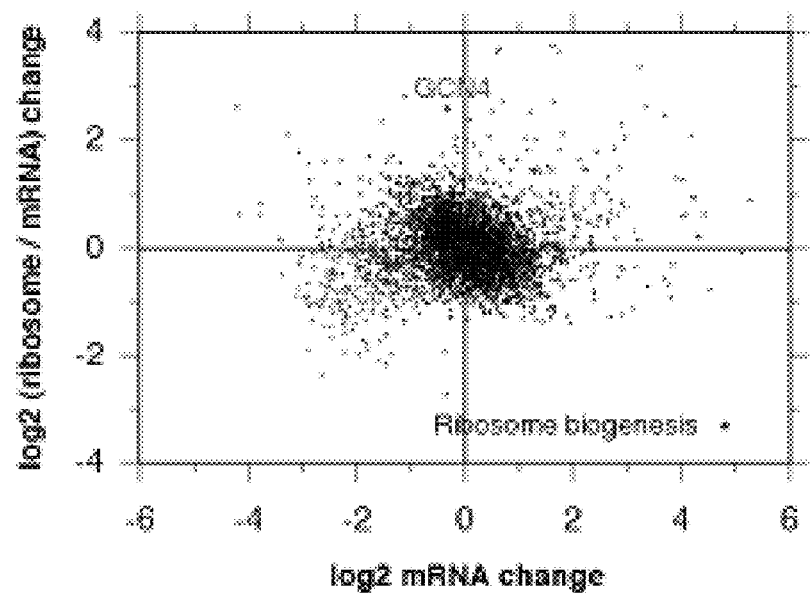
FIGS. 5A-B. Translational response to starvation.
Figure 5B:
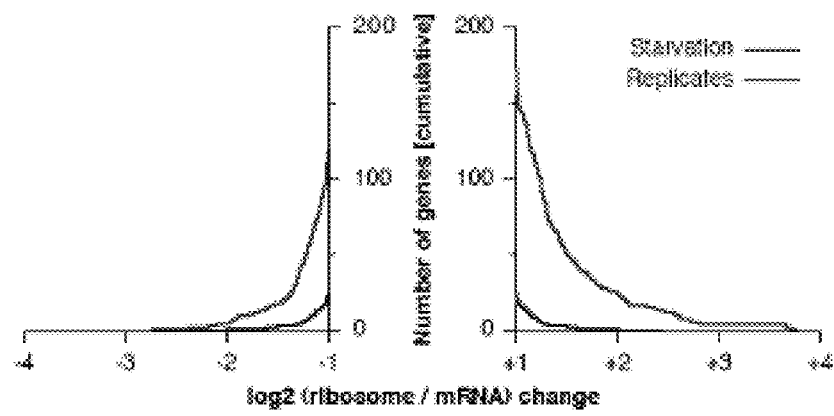
Figure 16A:
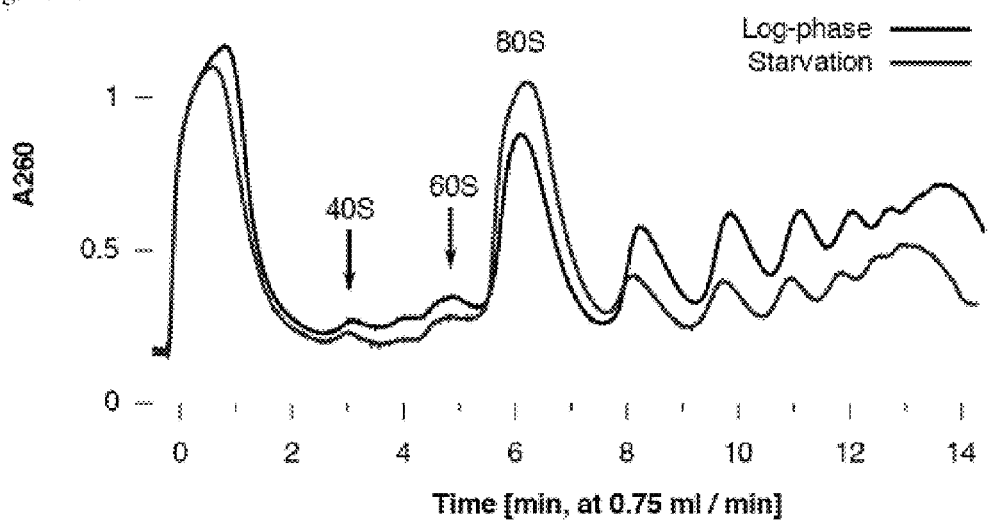
FIGS. 16A-C. Ribosome footprinting of cells subjected to acute amino acid starvation.
Figure 16B:
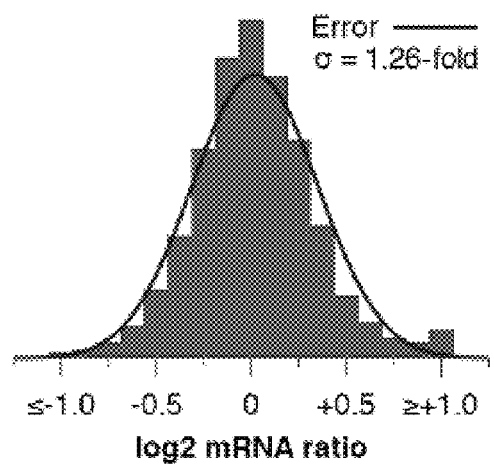
Figure 16C:
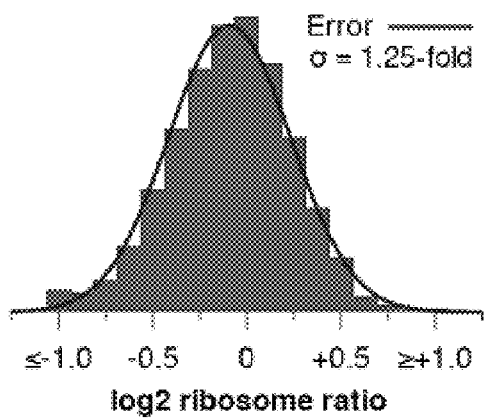
Figure 17:
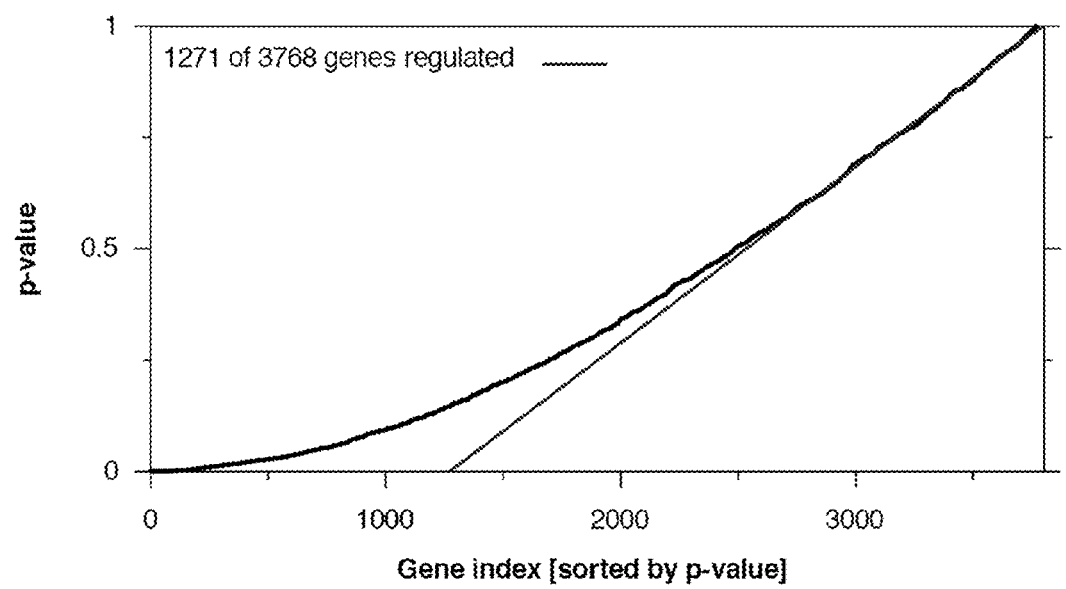
FIG. 17. Estimation of the number of translationally regulated genes. The distribution of p-values is fit by a model in which roughly one-third of reliably measured genes (1271 of 3768) are translationally regulated. The no-change null hypothesis p-value for each gene was estimated from the distribution of inter-replicate ratios of translation in biological replicates of the log-phase and starvation samples. The unchanged genes should have a uniform distribution of p values, whereas the translationally regulated genes will have p values skewed strongly towards 0. Thus, most large p values will be derived from the unregulated subset, and the distribution of p values at the high-p limit can be extrapolated down to p=0 to estimate the overall population of unregulated genes. The region of p>0.67 was used to fit p=0.000396 index −0.502, giving index (p=0)=1271.0.

Quantitation of ribosome footprints allows measurements of protein synthesis with a level of precision comparable to that of mRNA abundance measurements. We measured the response of yeast to acute amino acid starvation, a stress that is known to produce significant transcriptional and translational changes. After 20 minutes of amino acid deprivation we saw a substantial decrease in the fraction of ribosomes in polysomes, indicating an overall decrease in translation (FIG. 16A). Starvation globally decreases translational initiation via eIF2α phosphorylation, though certain messages are spared from this repressive effect. We quantified ribosome density and mRNA abundance in fully independent biological replicates of starvation conditions and again found very good inter-replicate agreement (FIG. 16B, FIG. 16C). We then combined data from these replicates to compare starvation with log-phase growth. There were large differences in ribosome density and in mRNA abundance between these two conditions (FIG. 5A). Many genes showed a significant change in ribosome density that could not be fully accounted for by a change in mRNA abundance, indicating translational regulation. We used differences between biological replicates to assess the error rate of our translation measurements and confirm that hundreds of genes show a two-fold or greater change in translation (FIG. 5B). We estimate that, in total, one third of measurable genes showed altered translation upon starvation (FIG. 17). A corrected false discovery rate of 10% for translationally regulated genes corresponds to a threshold of 2.0-fold change.

Figure 18:
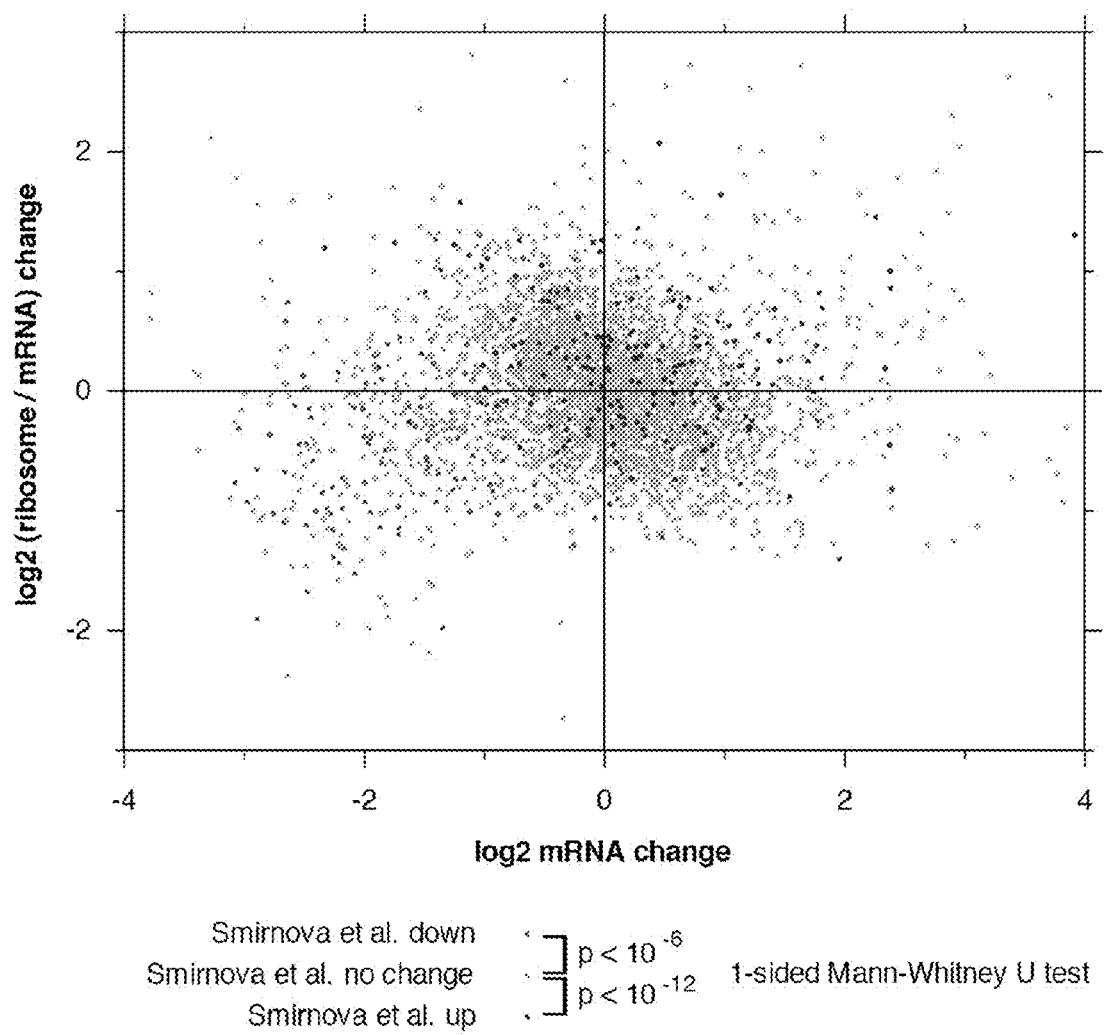
FIG. 18. Comparison of ribosome footprinting results with polysome fraction measurements by Smirnova et al. following amino acid starvation. Genes from FIG. 5 were re-plotted based on the change in translation status observed by Smirnova et al. The translation rate, as measured by ribosome density per mRNA abundance, was significantly different between these three groups by a 1-sided Mann-Whitney U test.

Many genes involved in ribosome biogenesis were translationally repressed in response to starvation (FIG. 5A), in agreement with data from a previous microarray study. This earlier work measured the fraction of mRNA associated with polysomes in order to determine the translational status of a gene. We found that the genes that they identified as translationally induced or repressed had a very significant positive or negative translational shift in response to starvation, respectively, relative to the overall distribution (FIG. 18). We also measured changes in translational efficiency for many other genes. Ribosome footprinting is able to detect small (<2.0-fold) quantitative changes in translation with high confidence. In contrast, measuring the fraction of polysome-associated RNAs may report only on complete translational inactivation.

Our observation of ribosome occupancy in 5' UTRs highlights how ribosome footprinting measures protein synthesis directly and distinguishes between translation of uORFs and coding sequences. For instance, we detect the 7-fold translational induction of GCN4, a well-studied, translationally regulated gene that fell below the level of statistical significance in the earlier polysome study. The regulation of GCN4 translation results from four uORFs in its 5' UTR. Extensive study of GCN4 has suggested that ribosomes always translate the first uORF, but that in log-phase growth they re-initiate at one of the subsequent uORFs, translate it as well, and then disengage entirely. During starvation, however, re-initiation bypasses the uORFs and reaches the main coding sequence, thereby relieving the translational repression imposed by uORFs 2-4. Ribosome density mapping experiments by Arava et al. showed that in log-phase growth, most GCN4 mRNAs have a single ribosome associated with the 5' UTR and no ribosomes associated with the coding sequence. Our ribosome footprinting data reveals a very high density of ribosomes specifically in the first GCN4} uORF, while the second through fourth uORFs have lower, but still significant, occupancy. In response to amino acid starvation, the ribosome density decreases in uORF 1 and essentially vanishes in uORFs 2-4 while increasing substantially in the coding sequence.

Our results are consistent with the standard model of GCN4 regulation, but we observe additional sites of translation in the 5' UTR. A fifth region of translation with a non-canonical AAAA TA initiation site is present even in log-phase growth, and is greatly enhanced under starvation. In contrast, ribosome occupancy of the first uORF, which was generally believed to be constitutive, appears somewhat reduced. Interestingly, an earlier study showed that when this novel upstream translated region was deleted, uORF 1 alone exerted a strong repressive effect on translation of the main coding sequence, in contrast to its normal mild effect (Grant & al. 1995). This was interpreted as evidence that the region is required to allow reinitiation following translation of uORF 1, and it was recently proposed based on genetic interactions that the translation initiation factor eIF3 might directly bind mRNA in this region. However, the starvation-induced translation we observe in this region may play a role in its effect on GCN4 regulation.

Figure 6A:
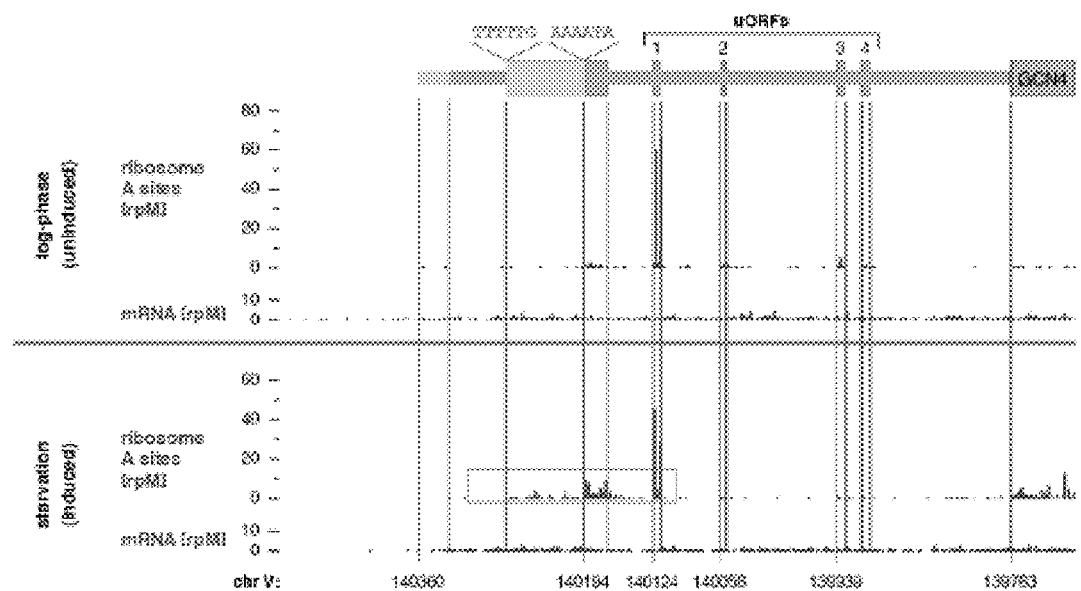
FIGS. 6A-D. Changes in 5' UTR translation during starvation.
Figure 6B:
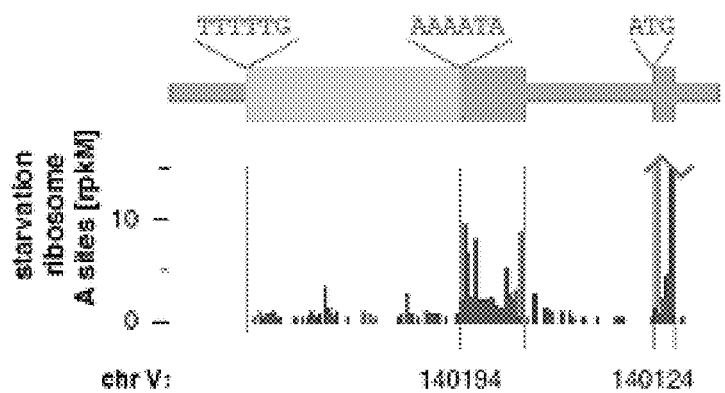
Figure 6C:
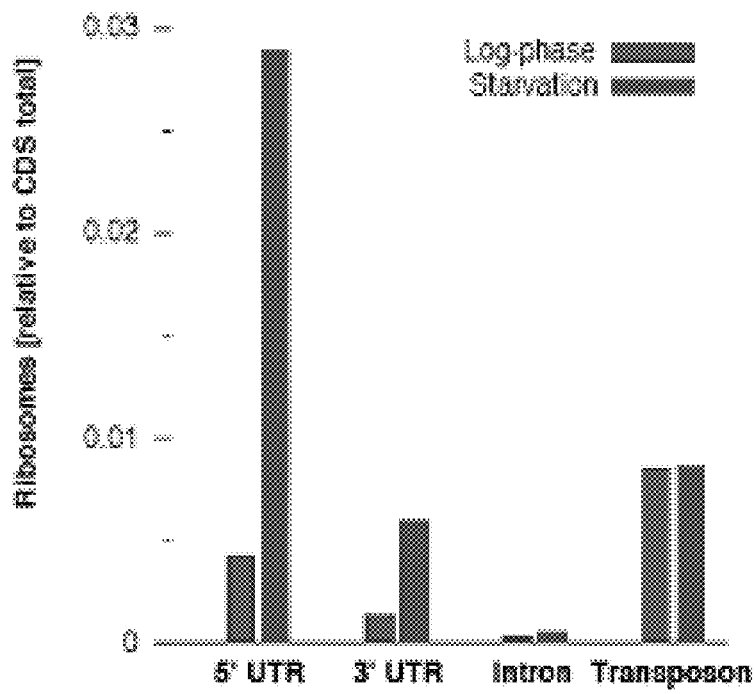
Figure 19A:
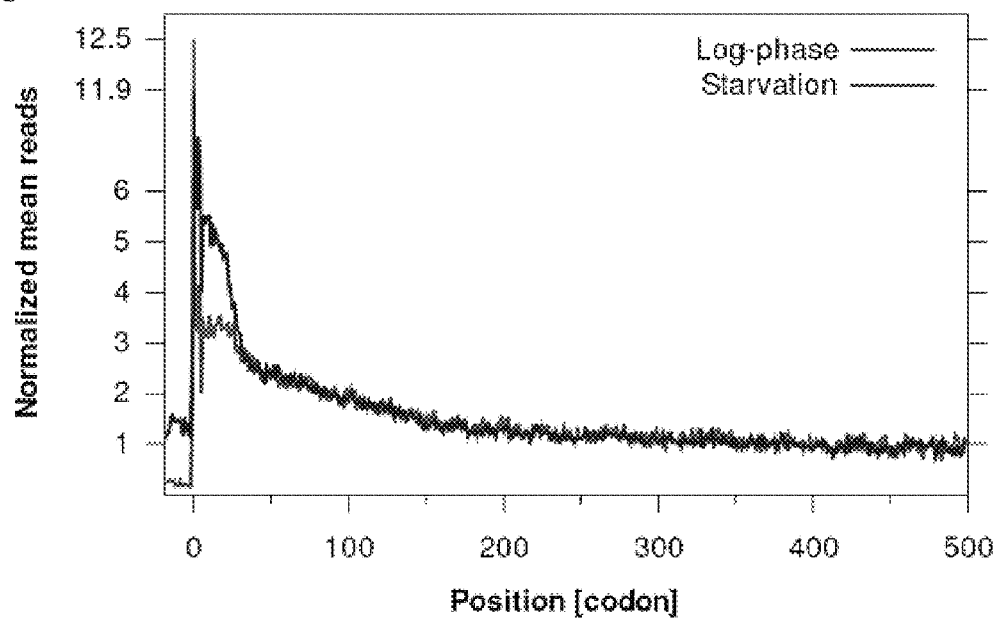
FIGS. 19A-B. Global effects of starvation on translation.
Figure 20:
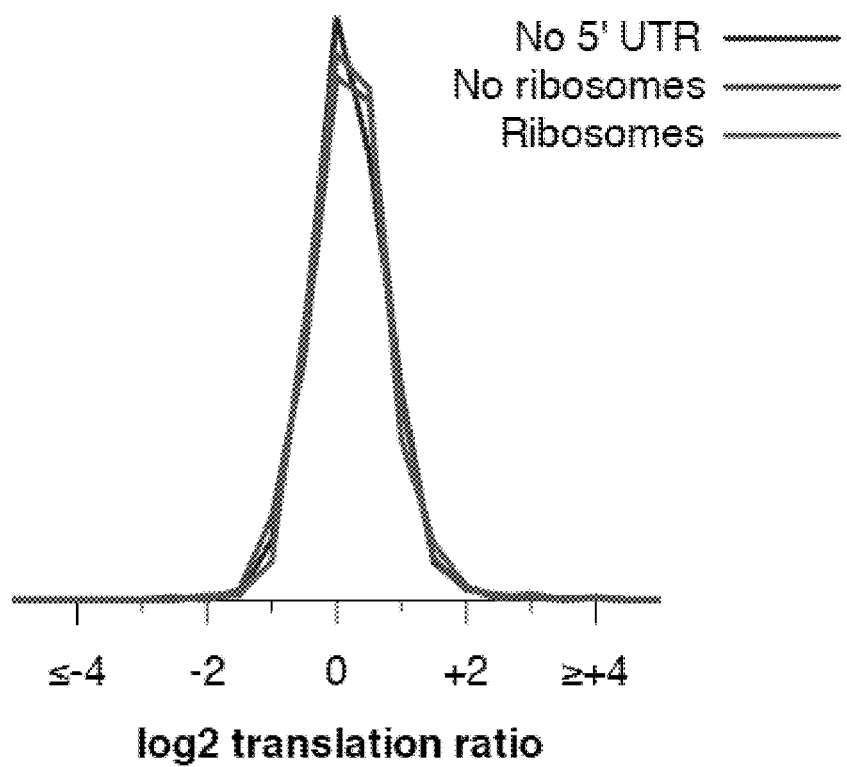
FIG. 20. Effect of 5'UTR on translational response to starvation. Genes were classified as having no annotated 5' UTR (or a 5' UTR shorter than a ribosome footprint), a 5' UTR with no ribosome footprints, or a 5' UTR with at least 4 ribosome footprints. The translational responses of these three populations to amino acid starvation were indistinguishable.
Figure 21:
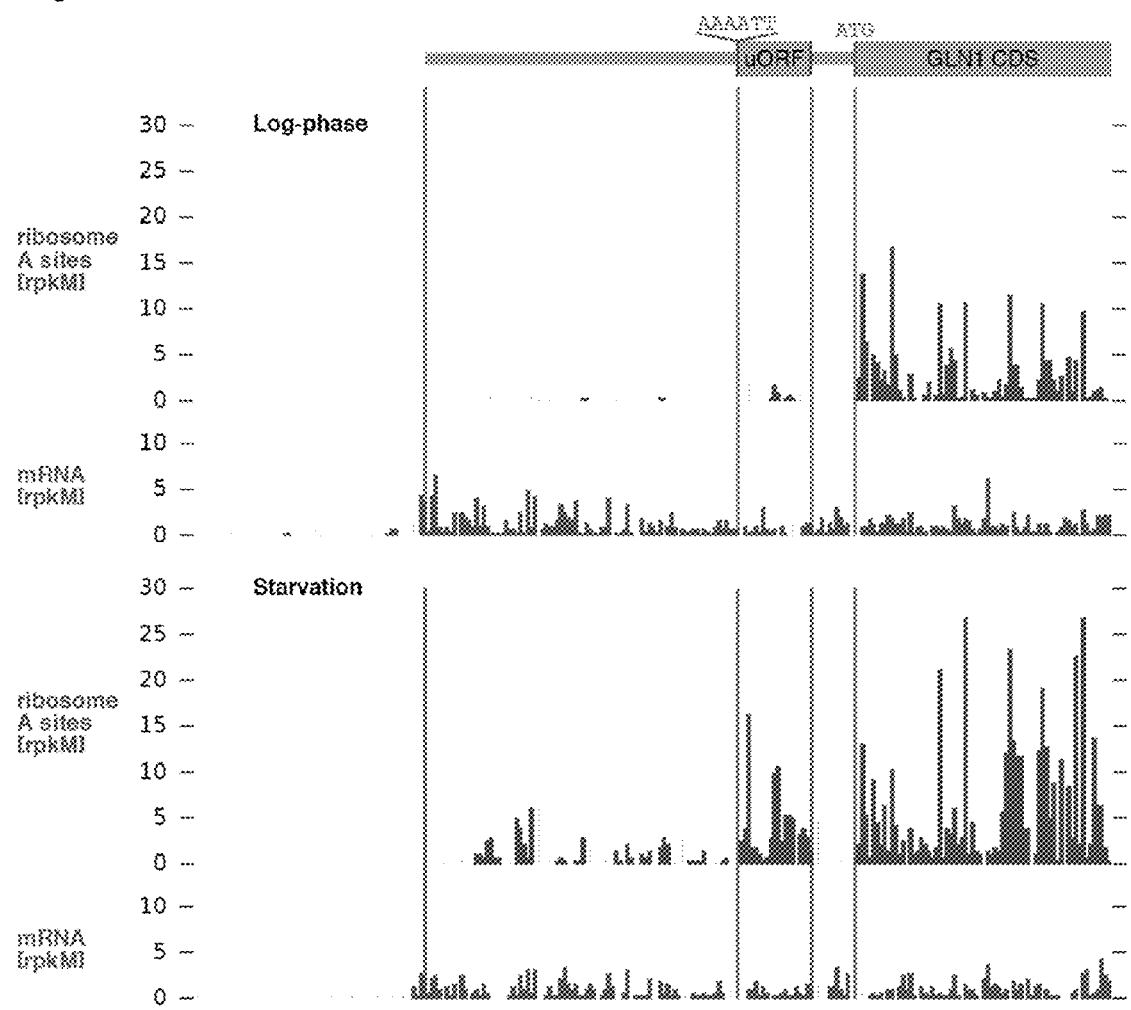
FIG. 21. Ribosome and mRNA density in the GLN1 5' UTR in log-phase growth and amino acid starvation. Ribosome density per mRNA in the GLN1 coding sequence increases 3.3-fold in response to amino acid starvation. There is also a dramatic increase in ribosome density on the 5' UTR. This increase is concentrated in the indicated non-ATG uORF, where some translation is detectable even in log-phase growth.
Figure 22:
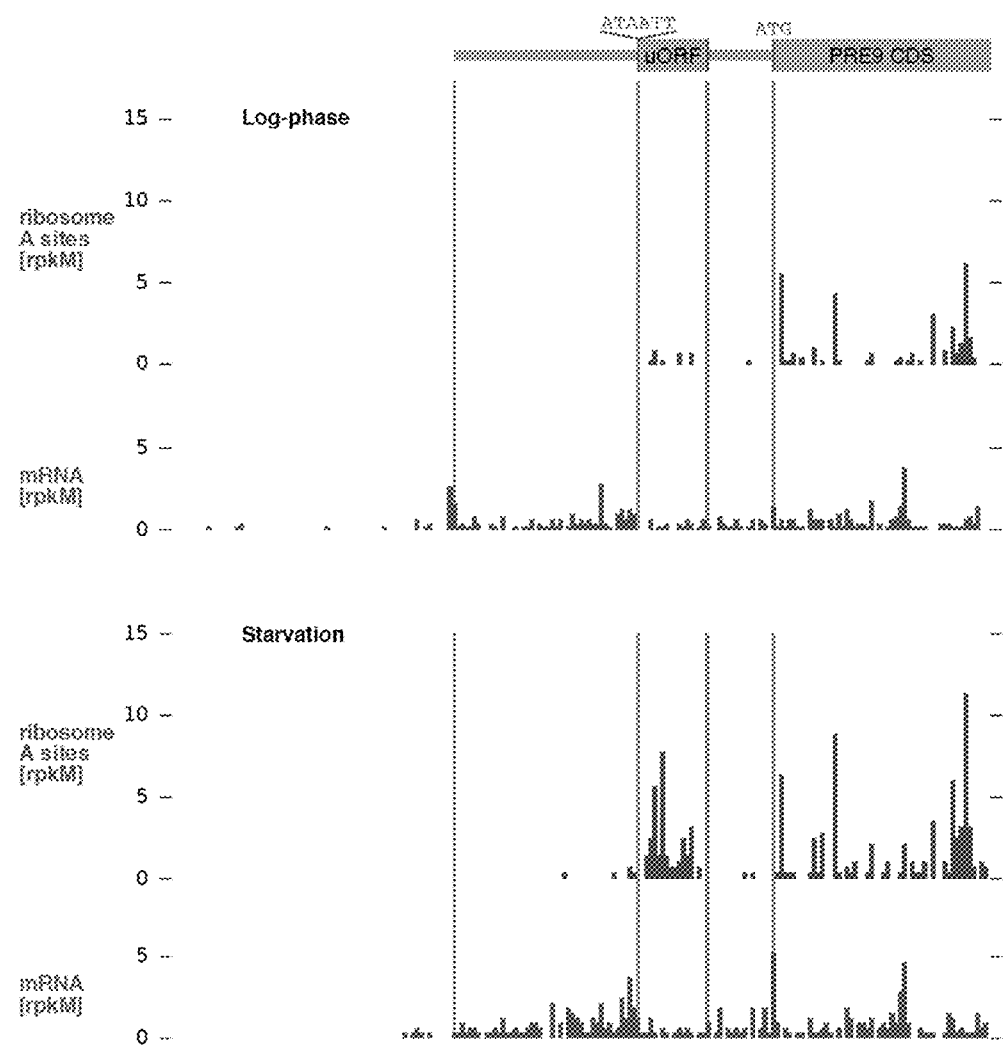
FIG. 22. Ribosome and mRNA density in the PRE9 5' UTR in log-phase growth and amino acid starvation. The mRNA abundance increases during starvation, but the translation rate is essentially unchanged. A non-ATG uORF in the 5' UTR shows some ribosome occupancy during log-phase growth, with a dramatic increase upon amino acid starvation.

We looked more broadly to determine the effect of starvation on translation of 5' UTRs. We found a roughly 6-fold increase in the fraction of ribosome footprints derived from 5' UTRs upon starvation (FIG. 6C). There was a smaller increase in ribosome occupancy of 3' UTRs, and little change in sequences such as introns or transposons. We also found that the ribosome density in the first 30 codons of protein-coding genes was even higher after starvation than in log-phase growth, though the rest of the distribution was unchanged (FIG. 19A). As uORFs are typically short, elevated 5' ribosome density will increase the ribosome occupancy of uORFs relative to full-length coding sequences. However, this effect is not large enough to account for the full 6-fold change we observe. We also tested whether 5' UTR translation was directly linked to translational regulation upon starvation. We no significant difference between the translational changes of genes with ribosome-occupied 5' UTRs, genes with unoccupied 5' UTRs, and genes with minimal 5' UTRs (FIG. 20).

Figure 6D:
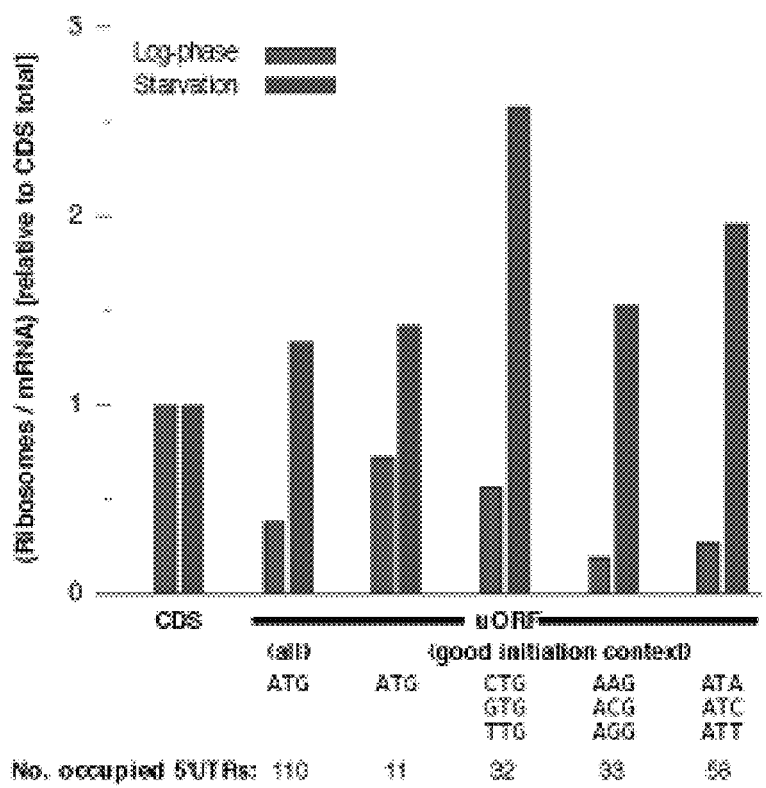
Figure 19B:
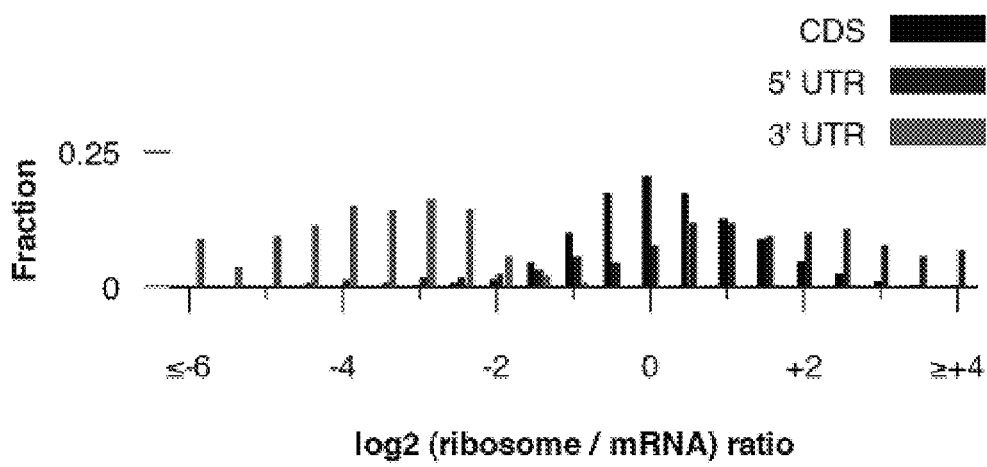

We then looked more specifically at candidate uORFs to determine how starvation affected their translation. The non-ATG uORFs we identified showed a particularly dramatic increase in ribosome occupancy during starvation (FIG. 6D). Examination of specific 5' UTRs such as GLN1} and PRE9 revealed non-ATG uORFs which were marginally translated during log-phase growth but had much higher ribosome density after starvation. However, even in the case of GLN1, it is clear that no single uORF can account for the entire distribution of ribosomes on the 5' UTR. Instead, the effect seems to result from a more general change in the stringency of initiation codon selection, which favors certain non-canonical start sites but has broader effects as well. Consistent with this, we find that the ratio of ribosomes to mRNA for 5' UTRs is generally increased upon starvation, rather than showing an effect specifically focused on a subset of genes with uORFs (FIG. 19B). The repression of translation upon starvation is mediated by phosphorylation of eIF2α, a translational initiation factor with a prominent role in initiator codon selection. Phosphorylation of eIF2α may also cause the altered stringency of initiation that we observe following amino acid starvation.

Perspective

Deep sequencing of ribosome footprints allows quantitative, genome-wide measurements of translation. We report translational data from budding yeast, but we foresee no technical barriers to applying our method in other eukaryotic systems, including mammals. Footprinting and ribosome purification are more involved than mRNA purification. However, ribosome footprinting does not require isolating intact, full-length mRNA. In future application, monosomes could be recovered by pelleting or by expression of epitope-tagged ribosomes, perhaps even in a tissue-specific manner, rather than by sucrose density gradient fractionation. Our measurements of mRNA abundance and of translation are highly reproducible, suggesting that deep sequencing can be used in place of microarrays to measure gene expression and that translation can be measured in place of or in addition to mRNA abundance. Position-specific ribosome density measurements revealed uORFs and distinguished ribosomes occupying them from ribosomes translating the associated coding sequence. Therefore it is possible to quantify phenomena such as frameshifting and read-through of stop codons. By monitoring ribosome density at different positions within coding sequences, we have defined different phases of translation that are characterized by different average ribosome densities. Gene-specific ribosome density profiles shows the rate of translation across individual genes, thereby allowing study of how RNA structure, codon usage, and peptide sequence affect translational elongation.

Ribosome Profiling in Mammalian Cells

Ribosome profiling has been conducted using the methods and reagents described herein on both human and mouse tissue culture cells. It has been demonstrated that the methods described herein are useful to measure protein synthesis in both human and mouse.

Simplified Protocols with Crude Ribosome Purification

It has been demonstrated that the technically challenging steps of ribosome purification by sucrose density gradient fractionation is not always necessary, and that a crude fractionation by size of ribosomes away from other cellular RNA can be sufficient for the methods described herein. In particular, ultracentrifugation to pellet ribosomes in a sucrose cushion can be employed.

Subtractive Hybridization of Contaminating RNAs

Figure 23:
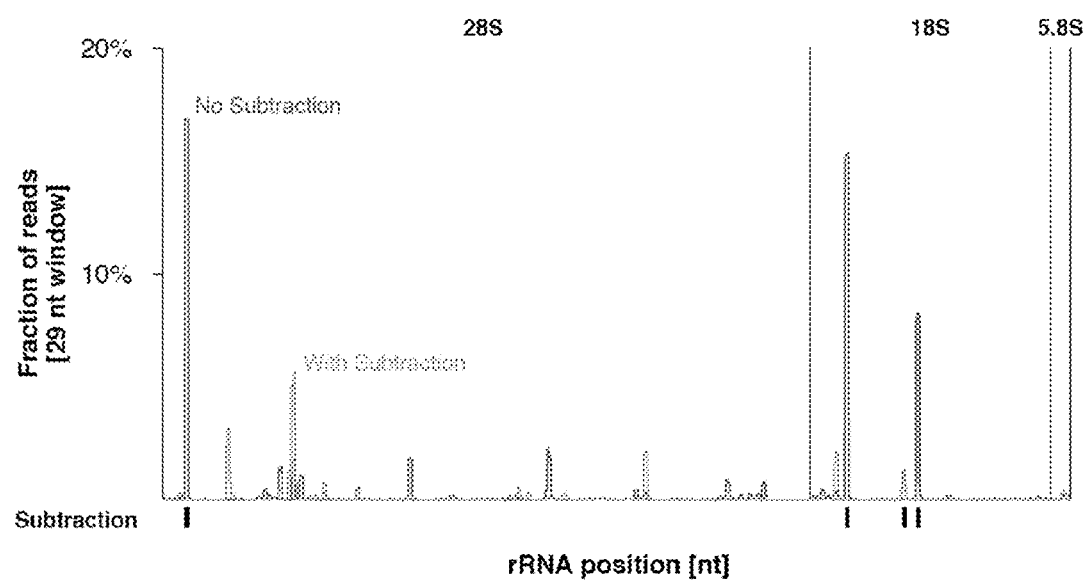
FIG. 23. This figure depicts the effectiveness of rRNA subtraction in ribosome footprinting samples prepared from mouse ES cells. In one preliminary experiment ("No subtraction"), only the two human-derived subtraction oligos were used to remove rRNA. The coverage of rRNA positions by sequencing reads, summed over a 29 nt sliding window, is plotted to show that a few specific sites account for as much as 15% each of all sequencing reads obtained in the sample. A subsequent sample was prepared in the same way, but subtraction employed the four mouse-specific subtraction oligos, target position of which in the rRNA is marked below the graph. Coverage of rRNA positions in this second sample ("With Subtraction") shows that the three abundant contaminating sequences in the preliminary sample are depleted well. This produced a decrease in the overall fraction of rRNA-derived sequences from 60% of all reads to 25% of all reads and a concomitant 75% increase in the yield of usable footprint sequences.

FIG. 23 depicts the effectiveness of rRNA subtraction in ribosome footprinting samples prepared from mouse ES cells. In one experiment ("No subtraction"), only the two human-derived subtraction oligos were used to remove rRNA. The coverage of rRNA positions by sequencing reads, summed over a 29 nt sliding window, is plotted to show that a few specific sites account for as much as 15% each of all sequencing reads obtained in the sample. A subsequent sample was prepared in the same way, but subtraction employed the four mouse-specific subtraction oligos, target position of which in the rRNA is marked below the graph. Coverage of rRNA positions in this second sample ("With Subtraction") shows that the three abundant contaminating sequences in the preliminary sample are depleted well. This produced a decrease in the overall fraction of rRNA-derived sequences from 60% of all reads to 25% of all reads and a concomitant 75% increase in the yield of usable footprint sequences.

Footprinting of Translation Initiation

Figure 24:
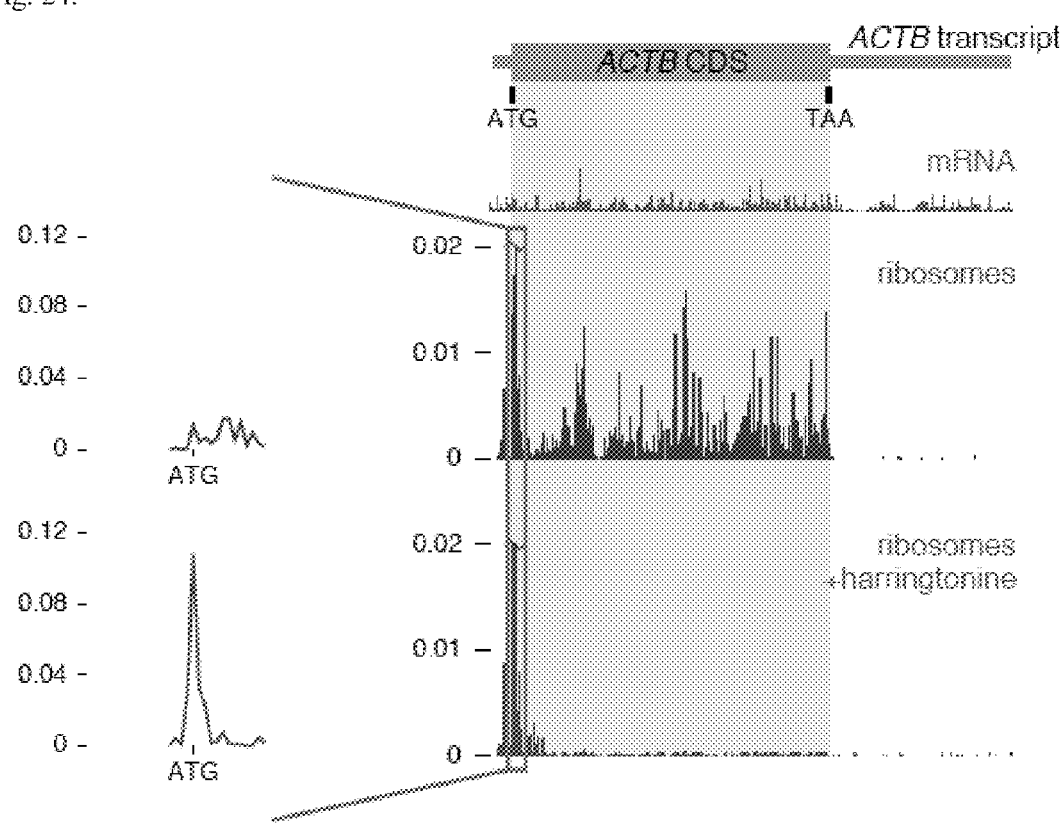
FIG. 24. This figure depicts ribosome footprinting of translation and translational initiation in mouse embryonic stem cells. Three sequencing experiments were performed using fragmented mRNA, ribosome footprints, and harringtonine-treated ribosome footprints from mouse embryonic stem cells. Sequencing reads were aligned to the transcripts in the UCSC known Gene database, as known in the art, and the number of reads aligning to each position on the highly-expressed ACTB transcript is plotted for each sample. There is uniform mRNA-Seq coverage across the entire transcript, but ribosome footprints are clearly restricted to the protein-coding gene, with a notable spike at the initiator AUG codon. Harringtonine treatment causes a dramatic enrichment of footprints from the start codon and a dramatic depletion of ribosome footprints across the rest of the gene. These indicate that ribosome footprinting can profile translation in mammalian cells and that harringtonine treatment can be used to specifically delineate sites of translation initiation.

FIG. 24 depicts ribosome footprinting of translation and translational initiation in mouse embryonic stem cells. Three sequencing experiments were performed using fragmented mRNA, ribosome footprints, and harringtonine-treated ribosome footprints from mouse embryonic stem cells. Sequencing reads were aligned to the transcripts in the UCSC known Gene database, as known in the art, and the number of reads aligning to each position on the highly-expressed ACTB transcript is plotted for each sample. There is uniform mRNA-Seq coverage across the entire transcript, but ribosome footprints are clearly restricted to the protein-coding gene, with a notable spike at the initiator AUG codon. Harringtonine treatment causes a dramatic enrichment of footprints from the start codon and a dramatic depletion of ribosome footprints across the rest of the gene. These indicate that ribosome footprinting can profile translation in mammalian cells and that harringtonine treatment can be used to specifically delineate sites of translation initiation.

---

What is claimed is:

1. A method for detecting a plurality of mRNA molecules bound to at least one ribosome, said method comprising:
   (i) contacting said plurality of mRNA molecules with an enzymatic degradant or a chemical degradant thereby forming a plurality of RNA fragments, wherein each RNA fragment comprises an RNA portion protected from said enzymatic degradant or said chemical degradant by a ribosome to which the RNA portion is bound;
   (ii) amplifying said RNA fragments comprising said RNA portions to form a detectable number of amplified nucleic acid fragments; and
   (iii) detecting said detectable number of amplified nucleic acid fragments, thereby detecting an amount of two or more of said RNA portions and correlating said amount of two or more of said RNA portions to a rate of translation of one or more of said plurality of mRNA molecules.

2. The method of claim 1, wherein said amount of two or more RNA portions are correlated to an amount of ribosomal activity on one or more of said plurality of mRNA molecules.

3. The method of claim 1, wherein said amount of two or more RNA portions are correlated to an amount of protein synthesis from one or more of said plurality of mRNA molecules.

4. The method of claim 1, wherein said amount of two or more RNA portions are correlated to locations for boundaries of translated sequences.

5. A method for detecting a plurality of mRNA molecules bound to at least one ribosome, said method comprising:
   (i) contacting said plurality of mRNA molecules with an enzymatic degradant or a chemical degradant thereby forming a plurality of RNA fragments, wherein each RNA fragment comprises an RNA portion protected from said enzymatic degradant or said chemical degradant by a ribosome to which the RNA portion is bound;
   (ii) amplifying said RNA fragments to form a detectable number of amplified nucleic acid fragments; and
   (iii) detecting said detectable number of amplified nucleic acid fragments, thereby detecting said plurality of mRNA molecules bound to at least one ribosome,
   wherein said amplifying and detecting comprises:
   (a) contacting said plurality of RNA fragments with a DNA polymerase and a DNA polymerase primer thereby forming a plurality of linear DNA molecules;
   (b) contacting said plurality of linear DNA molecules with a ligase thereby forming a plurality of circularized DNA molecules;
   (c) amplifying said plurality of circularized DNA thereby forming a detectable number of amplified DNA molecules; and
   (d) detecting said detectable number of amplified DNA molecules thereby detecting said plurality of mRNA molecules bound to at least one ribosome.

6. A method for detecting a plurality of mRNA molecules bound to at least one ribosome, said method comprising:
   (i) contacting said plurality of mRNA molecules with an enzymatic degradant or a chemical degradant thereby forming a plurality of RNA fragments, wherein each RNA fragment comprises an RNA portion protected from said enzymatic degradant or said chemical degradant by a ribosome to which the RNA portion is bound;

(ii) amplifying said RNA fragments to form a detectable number of amplified nucleic acid fragments; and
(iii) detecting said detectable number of amplified nucleic acid fragments, thereby detecting said plurality of mRNA molecules bound to at least one ribosome,
wherein said plurality of mRNA molecules comprise at least 1,000 different sequence species.

7. A method for determining translation activity for a plurality of mRNA molecules, comprising:
(i) treating a plurality of RNA-ribosome complexes, wherein each RNA-ribosome complex comprises an mRNA molecule having an RNA portion that is bound to a ribosome, under conditions sufficient produce a plurality of RNA fragments, wherein each RNA fragment comprises an RNA portion, and wherein each RNA fragment comprises a nucleotide sequence that is longer than the nucleotide sequence of said RNA portion;
(ii) sequencing the plurality of RNA fragments to determine the nucleotide sequences of the RNA portions; and
(iii) comparing the nucleotide sequences of the plurality of RNA portions to the nucleotide sequences of the mRNA molecules, thereby determining translation activity for the plurality of mRNA molecules,
wherein an amount of two or more RNA portions are correlated to a rate of translation of one or more mRNA molecules.

8. The method of claim 1, wherein said amplifying and detecting comprises:
(a) contacting said plurality of RNA fragments with a DNA polymerase and a DNA polymerase primer thereby forming a plurality of linear DNA molecules;
(b) contacting said plurality of linear DNA molecules with a ligase thereby forming a plurality of circularized DNA molecules;
(c) amplifying said plurality of circularized DNA thereby forming a detectable number of amplified DNA molecules; and
(d) detecting said detectable number of amplified DNA molecules thereby detecting said plurality of mRNA molecules bound to at least one ribosome.

9. The method according to claim 1, wherein said detecting comprises contacting said amplified nucleic acid fragments with a microarray.

10. The method according to claim 1, wherein said amplified nucleic acid fragments comprise a detectable label.

11. The method according to claim 9, wherein said microarray comprises a nucleic acid at least 90% complementary to at least one of the amplified DNA molecules.

12. The method according to claim 1, further comprising isolating the mRNA molecules from a cell.

13. The method of claim 12, wherein the plurality of mRNA molecules comprise at least 90% of the mRNA sequence species from the cell.

14. The method according to claim 1, wherein said plurality of mRNA molecules comprise at least 1,000 different sequence species.

15. The method according to claim 1, wherein each of the RNA fragments are partially sequenced using a sequencing-by-synthesis technique to determine the nucleotide sequences of the RNA portions.

16. A method for detecting an RNA molecule bound to at least one ribosome, said method comprising:
(i) contacting said RNA molecule with an enzymatic degradant or chemical degradant thereby forming an RNA fragment, wherein the RNA fragment comprises an RNA portion protected from said enzymatic degradant or said chemical degradant by a ribosome to which the RNA portion is bound;
(ii) contacting said RNA fragment with a DNA polymerase and a DNA polymerase primer thereby forming a linear DNA;
(iii) contacting said linear DNA with a ligase thereby forming a circularized DNA;
(iv) amplifying said circularized DNA thereby forming a detectable number of amplified DNA molecules; and
(v) detecting said detectable number of amplified DNA molecules thereby detecting said RNA molecule bound to at least one ribosome.

17. A method for determining translation activity for a plurality of mRNA molecules, comprising:
(i) treating a plurality of RNA-ribosome complexes, wherein each RNA-ribosome complex comprises an mRNA molecule having an RNA portion that is bound to a ribosome, under conditions sufficient produce a plurality of RNA fragments, wherein each RNA fragment comprises an RNA portion, and wherein each RNA fragment comprises a nucleotide sequence that is longer than the nucleotide sequence of said RNA portion;
(ii) sequencing the plurality of RNA fragments to determine the nucleotide sequences of the RNA portions; and
(iii) comparing the nucleotide sequences of the plurality of RNA portions to the nucleotide sequences of the mRNA molecules, thereby determining translation activity for the plurality of mRNA molecules.

18. The method of claim 17, wherein the plurality of RNA-ribosome complexes is isolated from a cell and comprises at least 90% of the mRNA species from the cell.

19. The method of claim 17, further comprising isolating the mRNA molecules from a cell.

20. The method of claim 17, further comprising isolating the RNA-ribosome complexes from a cell.

21. The method of claim 17, wherein the plurality of RNAs comprises at least 1,000 different sequence species.

22. The method of claim 17, further comprising quantifying the relative amounts of two or more of the RNA portions in the RNA-ribosome complexes.

23. The method of claim 17, wherein each of the RNA fragments are partially sequenced using a sequencing-by-synthesis technique to determine the nucleotide sequences of the RNA portions.

24. The method of claim 17, wherein the translation activity comprises a rate of translation for one or more RNA in the plurality of RNA-ribosome complexes.

25. The method of claim 17, wherein the translation activity comprises the locations for boundaries of translated sequences.

26. The method of claim 17, wherein the translation activity comprises the reading frame being translated.

27. The method according to claim 12, wherein said mRNA molecules are each bound to at least one ribosome prior to said isolating.

28. A method for detecting a plurality of RNA molecules bound to at least one ribosome, said method comprising:
(i) contacting said plurality of RNA molecules with an enzymatic degradant or a chemical degradant thereby forming a plurality of RNA fragments, wherein each RNA fragment comprises an RNA portion protected from said enzymatic degradant or said chemical degradant by a ribosome to which the RNA portion is bound;
(ii) amplifying said RNA fragments to form a detectable number of amplified nucleic acid fragments; and (iii) detecting said detectable number of amplified nucleic acid fragments, thereby detecting said plurality of RNA molecules bound to at least one ribosome;

wherein said amplifying and detecting comprises:

(a) contacting said plurality of RNA fragments with a DNA polymerase and a DNA polymerase primer thereby forming a plurality of linear DNA molecules;

(b) contacting said plurality of linear DNA molecules with a ligase thereby forming a plurality of circularized DNA molecules;

(c) amplifying said plurality of circularized DNA thereby forming a detectable number of amplified DNA molecules; and (d) detecting said detectable number of amplified DNA molecules thereby detecting said plurality of RNA molecules bound to at least one ribosome.

* * * * *

UNITED STATES PATENT AND TRADEMARK OFFICE
CERTIFICATE OF CORRECTION

| | | |
|---|---|---|
| PATENT NO. | : 8,486,865 B2 | Page 1 of 1 |
| APPLICATION NO. | : 12/611817 | |
| DATED | : July 16, 2013 | |
| INVENTOR(S) | : Jonathan Weissman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Tenth Day of March, 2015

Michelle K. Lee
*Deputy Director of the United States Patent and Trademark Office*